US007622557B2

(12) United States Patent
Sorrentino et al.

(10) Patent No.: US 7,622,557 B2
(45) Date of Patent: Nov. 24, 2009

(54) ANTIBODIES HAVING BINDING SPECIFICITY FOR THE EXTRACELLULAR DOMAIN OF A BREAST CANCER RESISTANCE PROTEIN (BCRP)

(75) Inventors: Brian Sorrentino, Memphis, TN (US); John Schuetz, Memphis, TN (US)

(73) Assignee: St. Jude Children's Research Hospital, Memphis, TN (US)

( * ) Notice: Subject to any disclaimer, the term of this patent is extended or adjusted under 35 U.S.C. 154(b) by 297 days.

(21) Appl. No.: 09/866,866

(22) Filed: May 29, 2001

(65) Prior Publication Data
US 2002/0102244 A1    Aug. 1, 2002

Related U.S. Application Data

(63) Continuation-in-part of application No. 09/584,586, filed on May 31, 2000, now Pat. No. 6,933,150, which is a continuation-in-part of application No. PCT/US99/11825, filed on May 27, 1999.

(60) Provisional application No. 60/086,988, filed on May 28, 1998.

(51) Int. Cl.
C07K 16/00    (2006.01)
(52) U.S. Cl. .................................. 530/387.9
(58) Field of Classification Search .............. 530/387.1, 530/395
See application file for complete search history.

(56) References Cited

U.S. PATENT DOCUMENTS

| 4,281,061 | A * | 7/1981 | Zuk et al. ............... 435/7.9 |
| 5,563,247 | A * | 10/1996 | Niman et al. ............ 530/387.7 |
| 5,571,687 | A * | 11/1996 | Casey et al. ............... 435/29 |
| 5,994,088 | A * | 11/1999 | Mechetner et al. ........ 530/387.1 |
| 6,313,277 | B1 * | 11/2001 | Ross et al. ................. 536/23.1 |
| 6,485,933 | B1 * | 11/2002 | Bandman et al. .......... 435/69.1 |
| 6,528,623 | B2 * | 3/2003 | Godfrey et al. .......... 530/387.1 |

FOREIGN PATENT DOCUMENTS

| WO | WO 93/24613 | 12/1993 |
| WO | WO 97/16535 | 5/1997 |
| WO | WO 98/12304 | 3/1998 |
| WO | WO 99/40110 | 8/1998 |
| WO | WO 99/61589 | 12/1999 |

OTHER PUBLICATIONS

Scheffer et al, Proc Am Assoc Cancer Res Mar. 2000;41:p. 803.*
Kohler et al, Eur J. Immunol 1976;6511-9.*
Datasheet for clone 4E3 antibody, DAKO Corp. 2004.*
Arcesi et al, Cancer Res. 1993;53:310-7.*
Owens et al., J of Immunological methods, 1994, vol. 168, pp. 149-165.*
U.S. Appl. No. 60/086,988, filed May 28, 1998, Provisional.
Allen et al., Cancer Res., 59: 4237-41, 1999.
Allikmets et al., Hum. Mol. Genet., 5: 1649-55, 1996.
Bhatia et al., Nat Med.,, 4: 1038-45, 1998.
Bhatia et al., J Exp. Med., 186: 619-624, 1997.
Brangi et al., Cancer Research, 59:5938-5946, 1999.
Bunting et al., Blood, 92(7): 2269-79, 1998.
Chaudhary and Roninson, Cell, 66: 85-94, 1991.
Doyle et al., Proc. Natl. Acad. Sci. USA, 95: 15665-15670,1998.
Galipeau et al., Human Gene Therapy, 8: 1773-83, 1997.
Giles et al., Cancer, 86: 805-813, 1999.
Glimm and Eaves, Blood, 94: 2161-68, 1999.
Goodell et al., J Exp Med., 183: 1797-1806, 1996.
Goodell et al., Nat. Med., 3: 1337-45, 1997.
Gruol and Bourgeois, Biochem. Cell. Biol., 72: 561-71, 1994.
Gussoni et al, Nature, 401: 390-4, 1999.
Hanania et al., Cancer Gene Therapy, 1(1): 21-25, 1994.
Hanania et al., Gene Ther., 2: 279-84, 1995.
Hrycyna et al., Biochemistry, 37: 13660-73, 1998.
Jackson et al., PNAS USA, 96: 14482-86, 1999.
Johnstone et al., Blood, 93: 1075-85, 1999.
Leith et al., Blood, 94: 1086-99, 1999.
Maliepard et al., Cancer Res., 59: 4559-63, 1999.
Michieli et al., Br. J. Haematol., 104: 328-335, 1999.
Miyake et al., Cancer Res., 59: 8-13, 1999.
Nakayama et al., Blood, 92: 4296-4307, 1998.
Osawa et al., Science, 273: 242-45, 1996.
Persons et al., Blood, 90(5):1777-1786, 1997.
Podda et al., PNAS USA, 89: 9676-80, 1992.
Robinson et al., Biochemistry, 36: 11169-78, 1997.
Ross et al., Blood, 96(1):365-368, 2000.
Schinkel et al., PNAS USA, 94: 4028-33, 1997.
Shimizu et al., Blood, 91: 3688-92, 1998.
Smyth et al., PNAS USA, 95: 7024-29, 1998.
Sorrentino et al., Science, 257: 99-103, 1992.
Sorrentino et al., Blood, 86: 491-501, 1995.
Spencer et al., Blood, 87: 2579-87, 1996.
Tisdale et al., Blood, 92: 1131-41, 1998.
Traycoff et al., Exp. Hemotol., 26: 53-62, 1998.
Zandstra et al., Proc. Natl. Acad. Sci. USA, 94:4698-4703, 1997.
Zanjani et al., Exp. Hematol., 26: 353-60, 1998.
Ziegler et al., Science, 285: 1553-8, 1999.

(Continued)

Primary Examiner—Michail A Belyavskyi
(74) Attorney, Agent, or Firm—Darby & Darby P.C.

(57) ABSTRACT

The present invention includes methods of identifying and/or isolating stem cells based on expression of BCRP. The present invention also describes methods of obtaining and/or using cell populations enriched for stem cells. In addition, methods are provided for diagnosing and/or prognosing leukemia, particularly human acute myelogenous leukemia (AML), through assaying for BCRP expression in leukemic cells.

10 Claims, 1 Drawing Sheet

OTHER PUBLICATIONS

Bunting K.D., "ABC Transporters as Phenotypic Markers and Functional Regulators of Stem Cells", Stem Cells 2002 20:11-20.

Wall et al., "The BCRP Gene Product Transports the Stem Cell Marker Hoechst 33342 and Function Depends upon the Amount of Protein and an Intact Walker A Motif", Proceedings of the American Association for Cancer Research Annual, vol. 42 Mar. 2001, p. 281 XP001093958.

Zhou et al., "The ABC transporter Bcrpl/ABCG2 is expressed in a wide variety of stem cells and is a molecular determinant of the side-population phenotype" Nature Medicine 2001 7(9) : 1028-1034.

Zhou et al., "Expression of the Breast Cancer Resistance Protein (BCRP) in Side Population (SP) Stem Cells, Natural Killer (NK) Lymphocytes, and Erythroid Progenitor Cells", Blood 2000 96(11) :820a.

Ozvegy-Laeka, et al.; Function-dependent conformational changes of the ABCG2 multi-drug transporter modify its interaction with a monoclonal antibody on the cell surface; *J. Biol. Chem.* 2005; 280(6): 4219-4227.

Diestra J.E., et al.; Frequent expression of the multi-drug resistance-associated protein BCRP/MXR/ABCP/ABCG2 in human tumours detected by the BXP-21 monoclonal antibody in paraffin-embedded material; *J. Pathol.* Oct. 2002 198(2):213-219.

Maliepaard, M., et al.; Subcellular localization and distribution of the breast cancer resistance protein transporter in normal human tissues; *Cancer Res.* Apr. 15, 2001; 61(8):3458-3464.

Scheffer G.L., et al.; Breast cancer resistance protein is localized at the plasma membrane in mitoxantrone- and topotecan-resistant cell lines; *Cancer Res.* May 15, 2000; 60(10): 2589-2593.

* cited by examiner

SEQUENCE LISTING

<160> NUMBER OF SEQ ID NOS: 27

<210> SEQ ID NO 1
<211> LENGTH: 3860
<212> TYPE: DNA
<213> ORGANISM: Homo sapiens

<400> SEQUENCE: 1

```
atggatcttg aaggggaccg caatggagga gcaaagaaga agaacttttt taaactgaac      60
aataaaagtg aaaaagataa gaaggaaaag aaaccaactg tcagtgtatt ttcaatgttt     120
cgctattcaa attggcttga caagttgtat atggtggtgg gaactttggc tgccatcatc     180
catggggctg gacttcctct catgatgctg gtgtttggag aaatgacaga tatctttgca     240
aatgcaggaa atttagaaga tctgatgtca aacatcacta atagaagtga tatcaatgat     300
acagggttct tcatgaatct ggaggaagac atgaccagat atgcctatta ttacagtgga     360
attggtgctg gggtgctggt tgctgcttac attcaggttt cattttggtg cctggcagct     420
ggaagacaaa tacacaaaat tagaaaacag tttttttcatg ctataatgcg acaggagata     480
ggctggtttg atgtgcacga tgttggggag cttaacaccc gacttacaga tgatgtctct     540
aagattaatg aaggtattgg tgacaaaatt ggaatgttct ttcagtcaat ggcaacattt     600
ttcactgggt ttatagtagg atttacacgt ggttggaagc taaccttgt gattttggcc     660 atcagtcctg ttcttggact gtcagctgct gtctgggcaa agatactatc ttcatttact     720
```

-continued

```
gataaagaac tcttagcgta tgcaaaagct ggagcagtag ctgaagaggt cttggcagca      780
attagaactg tgattgcatt tggaggacaa aagaaagaac ttgaaaggta caacaaaaat      840
ttagaagaag ctaaaagaat tgggataaag aaagctatta cagccaatat ttctataggt      900
gctgctttcc tgctgatcta tgcatcttat gctctggcct tctggtatgg gaccaccttg      960
gtcctctcag gggaatattc tattggacaa gtactcactg tattcttttc tgtattaatt     1020
ggggctttta gtgttggaca ggcatctcca agcattgaag catttgcaaa tgcaaggaga     1080
gcagcttatg aaatcttcaa gataattgat aataagccaa gtattgacag ctattcgaag     1140
agtgggcaca aaccagataa tattaaggga aatttggaat tcagaaatgt tcacttcagt     1200
tacccatctc gaaagaagt taagatcttg aagggcctga acctgaaggt gcagagtggg     1260
cagacggtgg ccctggttgg aaacagtggc tgtgggaaga cacaacagt ccagctgatg      1320
cagaggctct atgaccccac agaggggatg gtcagtgttg atggacagga tattaggacc     1380
ataaatgtaa ggtttctacg ggaaatcatt ggtgtggtga tcaggaacc tgtattgttt      1440
gccaccacga tagctgaaaa cattcgctat ggccgtgaaa atgtcaccat ggatgagatt     1500
gagaaagctg tcaaggaagc caatgcctat gactttatca tgaaactgcc tcataaattt     1560
gacaccctgg ttggagagag aggggcccag ttgagtggtg ggcagaagca gaggatcgcc     1620
attgcacgtg ccctggttcg caaccccaag atcctcctgc tggatgaggc cacgtcagcc     1680
ttggacacag aaagcgaagc agtggttcag gtggctctgg ataaggccag aaaaggtcgg     1740
accaccattg tgatagctca tcgtttgtct acagttcgta atgctgacgt catcgctggt     1800
ttcgatgatg gagtcattgt ggagaaagga atcatgatg aactcatgaa agagaaaggc      1860
atttacttca aacttgtcac aatgcagaca gcaggaaatg aagttgaatt agaaaatgca     1920
gctgatgaat ccaaaagtga aattgatgcc ttggaaatgt cttcaaatga ttcaagatcc     1980
agtctaataa gaaaagatc aactcgtagg agtgtccgtg gatcacaagc ccaagacaga     2040
aagcttagta ccaaagaggc tctggatgaa agtatacctc cagtttcctt tggaggatt     2100
atgaagctaa atttaactga atggcctat tttgttgttg gtgtattttg tgccattata     2160
aatggaggcc tgcaaccagc atttgcaata atatttttcaa agattatagg ggttttaca    2220
agaattgatg atcctgaaac aaaacgacag aatagtaact tgttttcact attgtttcta    2280
gcccttggaa ttatttcttt tattacattt ttccttcaag gtttcacatt tggcaaagct    2340
ggagagatcc tcaccaagcg gctccgatac atggttttcc gatccatgct cagacaggat    2400
gtgagttggt ttgatgaccc taaaaacacc actggagcat tgactaccag gctcgccaat    2460
gatgctgctc aagttaaagg ggctataggt tccaggcttg ctgtaattac ccagaatata    2520
gcaaatcttg gacaggaat aattatatcc ttcatctatg gttggcaact aacactgtta    2580
ctcttagcaa ttgtacccat cattgcaata gcaggagttg ttgaaatgaa atgttgtct    2640
ggacaagcac tgaagataa gaaagaacta gaaggtgctg ggaagatcgc tactgaagca    2700
atagaaaact tccgaaccgt tgtttctttg actcaggagc agaagtttga acatatgtat    2760
gctcagagtt tgcaggtacc atacagaaac tctttgagga agcacacat ctttggaatt    2820
acatttttcct tcacccaggc aatgatgtat ttttcctatg ctggatgttt ccggtttgga    2880
gcctacttgg tggcacataa actcatgagc tttgaggatg ttctgttagt attttcagct    2940
gttgtctttg gtgccatggc cgtgggcaa gtcagttcat tgctcctga ctatgccaaa    3000
gccaaaatat cagcagccca catcatcatg atcattgaaa aaacccctt gattgacagc    3060
tacagcacgg aaggcctaat gccgaacaca ttggaaggaa atgtcacatt tggtgaagtt    3120
```

-continued

```
gtattcaact atcccacccg accggacatc ccagtgcttc agggactgag cctggaggtg    3180
aagaagggcc agacgctggc tctggtgggc agcagtggct gtgggaagag cacagtggtc    3240
cagctcctgg agcggttcta cgacccttg gcagggaaag tgctgcttga tggcaaagaa     3300
ataaagcgac tgaatgttca gtggctccga gcacacctgg gcatcgtgtc ccaggagccc    3360
atcctgtttg actgcagcat tgctgagaac attgcctatg gagacaacag ccgggtggtg    3420
tcacaggaag agatcgtgag ggcagcaaag gaggccaaca tacatgcctt catcgagtca    3480
ctgcctaata aatatagcac taaagtagga gacaaaggaa ctcagctctc tggtggccag    3540
aaacaacgca ttgccatagc tcgtgcccct tgttagacagc ctcatatttt gcttttggat   3600
gaagccacgt cagctctgga tacagaaagt gaaaaggttg tccaagaagc cctggacaaa    3660
gccagagaag ccgcacctg cattgtgatt gctcaccgcc tgtccaccat ccagaatgca     3720
gacttaatag tggtgtttca gaatggcaga gtcaaggagc atggcacgca tcagcagctg    3780
ctggcacaga aaggcatcta ttttcaatg gtcagtgtcc aggctggaac aaagcgccag     3840
tgaactctgg ttaactccac                                                3860
```

```
<210> SEQ ID NO 2
<211> LENGTH: 1280
<212> TYPE: PRT
<213> ORGANISM: Homo sapiens

<400> SEQUENCE: 2
```

Met Asp Leu Glu Gly Asp Arg Asn Gly Gly Ala Lys Lys Lys Asn Phe
1               5                   10                  15

Phe Lys Leu Asn Asn Lys Ser Glu Lys Asp Lys Glu Lys Lys Pro
        20                  25                  30

Thr Val Ser Val Phe Ser Met Phe Arg Tyr Ser Asn Trp Leu Asp Lys
        35                  40                  45

Leu Tyr Met Val Val Gly Thr Leu Ala Ala Ile His Gly Ala Gly
    50                  55                  60

Leu Pro Leu Met Met Leu Val Phe Gly Glu Met Thr Asp Ile Phe Ala
65              70                  75                  80

Asn Ala Gly Asn Leu Glu Asp Leu Met Ser Asn Ile Thr Asn Arg Ser
                85                  90                  95

Asp Ile Asn Asp Thr Gly Phe Phe Met Asn Leu Glu Glu Asp Met Thr
            100                 105                 110

Arg Tyr Ala Tyr Tyr Tyr Ser Gly Ile Gly Ala Gly Val Leu Val Ala
        115                 120                 125

Ala Tyr Ile Gln Val Ser Phe Trp Cys Leu Ala Ala Gly Arg Gln Ile
    130                 135                 140

His Lys Ile Arg Lys Gln Phe Phe His Ala Ile Met Arg Gln Glu Ile
145                 150                 155                 160

Gly Trp Phe Asp Val His Asp Val Gly Glu Leu Asn Thr Arg Leu Thr
                165                 170                 175

Asp Asp Val Ser Lys Ile Asn Glu Gly Ile Gly Asp Lys Ile Gly Met
            180                 185                 190

Phe Phe Gln Ser Met Ala Thr Phe Phe Thr Gly Phe Ile Val Gly Phe
        195                 200                 205

Thr Arg Gly Trp Lys Leu Thr Leu Val Ile Leu Ala Ile Ser Pro Val
    210                 215                 220

Leu Gly Leu Ser Ala Ala Val Trp Ala Lys Ile Leu Ser Ser Phe Thr
225                 230                 235                 240

```
Asp Lys Glu Leu Leu Ala Tyr Ala Lys Ala Gly Ala Val Ala Glu Glu
                245                 250                 255

Val Leu Ala Ala Ile Arg Thr Val Ile Ala Phe Gly Gly Gln Lys Lys
            260                 265                 270

Glu Leu Glu Arg Tyr Asn Lys Asn Leu Glu Glu Ala Lys Arg Ile Gly
        275                 280                 285

Ile Lys Lys Ala Ile Thr Ala Asn Ile Ser Ile Gly Ala Ala Phe Leu
    290                 295                 300

Leu Ile Tyr Ala Ser Tyr Ala Leu Ala Phe Trp Tyr Gly Thr Thr Leu
305                 310                 315                 320

Val Leu Ser Gly Glu Tyr Ser Ile Gly Gln Val Leu Thr Val Phe Phe
            325                 330                 335

Ser Val Leu Ile Gly Ala Phe Ser Val Gly Gln Ala Ser Pro Ser Ile
        340                 345                 350

Glu Ala Phe Ala Asn Ala Arg Gly Ala Ala Tyr Glu Ile Phe Lys Ile
        355                 360                 365

Ile Asp Asn Lys Pro Ser Ile Asp Ser Tyr Ser Lys Ser Gly His Lys
    370                 375                 380

Pro Asp Asn Ile Lys Gly Asn Leu Glu Phe Arg Asn Val His Phe Ser
385                 390                 395                 400

Tyr Pro Ser Arg Lys Glu Val Lys Ile Leu Lys Gly Leu Asn Leu Lys
            405                 410                 415

Val Gln Ser Gly Gln Thr Val Ala Leu Val Gly Asn Ser Gly Cys Gly
        420                 425                 430

Lys Ser Thr Thr Val Gln Leu Met Gln Arg Leu Tyr Asp Pro Thr Glu
        435                 440                 445

Gly Met Val Ser Val Asp Gly Gln Asp Ile Arg Thr Ile Asn Val Arg
    450                 455                 460

Phe Leu Arg Glu Ile Ile Gly Val Val Ser Gln Glu Pro Val Leu Phe
465                 470                 475                 480

Ala Thr Thr Ile Ala Glu Asn Ile Arg Tyr Gly Arg Glu Asn Val Thr
            485                 490                 495

Met Asp Glu Ile Glu Lys Ala Val Lys Glu Ala Asn Ala Tyr Asp Phe
        500                 505                 510

Ile Met Lys Leu Pro His Lys Phe Asp Thr Leu Val Gly Glu Arg Gly
        515                 520                 525

Ala Gln Leu Ser Gly Gly Gln Lys Gln Arg Ile Ala Ile Ala Arg Ala
    530                 535                 540

Leu Val Arg Asn Pro Lys Ile Leu Leu Leu Asp Glu Ala Thr Ser Ala
545                 550                 555                 560

Leu Asp Thr Glu Ser Glu Ala Val Val Gln Val Ala Leu Asp Lys Ala
            565                 570                 575

Arg Lys Gly Arg Thr Thr Ile Val Ile Ala His Arg Leu Ser Thr Val
        580                 585                 590

Arg Asn Ala Asp Val Ile Ala Gly Phe Asp Asp Gly Val Ile Val Glu
    595                 600                 605

Lys Gly Asn His Asp Glu Leu Met Lys Glu Lys Gly Ile Tyr Phe Lys
    610                 615                 620

Leu Val Thr Met Gln Thr Ala Gly Asn Glu Val Glu Leu Glu Asn Ala
625                 630                 635                 640

Ala Asp Glu Ser Lys Ser Glu Ile Asp Ala Leu Glu Met Ser Ser Asn
            645                 650                 655
```

-continued

```
Asp Ser Arg Ser Ser Leu Ile Arg Lys Arg Ser Thr Arg Arg Ser Val
            660                 665                 670

Arg Gly Ser Gln Ala Gln Asp Arg Lys Leu Ser Thr Lys Glu Ala Leu
            675                 680                 685

Asp Glu Ser Ile Pro Pro Val Ser Phe Trp Arg Ile Met Lys Leu Asn
            690                 695                 700

Leu Thr Glu Trp Pro Tyr Phe Val Val Gly Val Phe Cys Ala Ile Ile
705                 710                 715                 720

Asn Gly Gly Leu Gln Pro Ala Phe Ala Ile Ile Phe Ser Lys Ile Ile
                725                 730                 735

Gly Val Phe Thr Arg Ile Asp Asp Pro Glu Thr Lys Arg Gln Asn Ser
            740                 745                 750

Asn Leu Phe Ser Leu Leu Phe Leu Ala Leu Gly Ile Ile Ser Phe Ile
            755                 760                 765

Thr Phe Phe Leu Gln Gly Phe Thr Phe Gly Lys Ala Gly Glu Ile Leu
    770                 775                 780

Thr Lys Arg Leu Arg Tyr Met Val Phe Arg Ser Met Leu Arg Gln Asp
785                 790                 795                 800

Val Ser Trp Phe Asp Asp Pro Lys Asn Thr Thr Gly Ala Leu Thr Thr
            805                 810                 815

Arg Leu Ala Asn Asp Ala Ala Gln Val Lys Gly Ala Ile Gly Ser Arg
            820                 825                 830

Leu Ala Val Ile Thr Gln Asn Ile Ala Asn Leu Gly Thr Gly Ile Ile
            835                 840                 845

Ile Ser Phe Ile Tyr Gly Trp Gln Leu Thr Leu Leu Leu Leu Ala Ile
    850                 855                 860

Val Pro Ile Ile Ala Ile Ala Gly Val Val Glu Met Lys Met Leu Ser
865                 870                 875                 880

Gly Gln Ala Leu Lys Asp Lys Lys Glu Leu Glu Gly Ala Gly Lys Ile
            885                 890                 895

Ala Thr Glu Ala Ile Glu Asn Phe Arg Thr Val Val Ser Leu Thr Gln
            900                 905                 910

Glu Gln Lys Phe Glu His Met Tyr Ala Gln Ser Leu Gln Val Pro Tyr
            915                 920                 925

Arg Asn Ser Leu Arg Lys Ala His Ile Phe Gly Ile Thr Phe Ser Phe
            930                 935                 940

Thr Gln Ala Met Met Tyr Phe Ser Tyr Ala Gly Cys Phe Arg Phe Gly
945                 950                 955                 960

Ala Tyr Leu Val Ala His Lys Leu Met Ser Phe Glu Asp Val Leu Leu
                965                 970                 975

Val Phe Ser Ala Val Val Phe Gly Ala Met Ala Val Gly Gln Val Ser
            980                 985                 990

Ser Phe Ala Pro Asp Tyr Ala Lys Ala Lys Ile Ser Ala Ala His Ile
            995                1000                1005

Ile Met Ile Ile Glu Lys Thr Pro Leu Ile Asp Ser Tyr Ser Thr
    1010                1015                1020

Glu Gly Leu Met Pro Asn Thr Leu Glu Gly Asn Val Thr Phe Gly
    1025                1030                1035

Glu Val Val Phe Asn Tyr Pro Thr Arg Pro Asp Ile Pro Val Leu
    1040                1045                1050

Gln Gly Leu Ser Leu Glu Val Lys Lys Gly Gln Thr Leu Ala Leu
    1055                1060                1065

Val Gly Ser Ser Gly Cys Gly Lys Ser Thr Val Val Gln Leu Leu
```

-continued

```
          1070                1075                1080
Glu Arg Phe Tyr Asp Pro Leu Ala Gly Lys Val Leu Leu Asp Gly
     1085                1090                1095

Lys Glu Ile Lys Arg Leu Asn Val Gln Trp Leu Arg Ala His Leu
     1100                1105                1110

Gly Ile Val Ser Gln Glu Pro Ile Leu Phe Asp Cys Ser Ile Ala
     1115                1120                1125

Glu Asn Ile Ala Tyr Gly Asp Asn Ser Arg Val Val Ser Gln Glu
     1130                1135                1140

Glu Ile Val Arg Ala Ala Lys Glu Ala Asn Ile His Ala Phe Ile
     1145                1150                1155

Glu Ser Leu Pro Asn Lys Tyr Ser Thr Lys Val Gly Asp Lys Gly
     1160                1165                1170

Thr Gln Leu Ser Gly Gly Gln Lys Gln Arg Ile Ala Ile Ala Arg
     1175                1180                1185

Ala Leu Val Arg Gln Pro His Ile Leu Leu Leu Asp Glu Ala Thr
     1190                1195                1200

Ser Ala Leu Asp Thr Glu Ser Glu Lys Val Val Gln Glu Ala Leu
     1205                1210                1215

Asp Lys Ala Arg Glu Gly Arg Thr Cys Ile Val Ile Ala His Arg
     1220                1225                1230

Leu Ser Thr Ile Gln Asn Ala Asp Leu Ile Val Val Phe Gln Asn
     1235                1240                1245

Gly Arg Val Lys Glu His Gly Thr His Gln Gln Leu Leu Ala Gln
     1250                1255                1260

Lys Gly Ile Tyr Phe Ser Met Val Ser Val Gln Ala Gly Thr Lys
     1265                1270                1275

Arg Gln
     1280

<210> SEQ ID NO 3
<211> LENGTH: 3860
<212> TYPE: DNA
<213> ORGANISM: homo sapiens

<400> SEQUENCE: 3
atggatcttg aaggggaccg caatggagga gcaaagaaga agaactttt taaactgaac      60 aataaaagtg aaaagataa gaaggaaag aaaccaactg tcagtgtatt ttcaatgttt     120
cgctattcaa attggcttga caagttgtat atggtggtgg aactttggc tgccatcatc     180 catgggctg gacttcctct catgatgctg tgtttggag aaatgacaga tatctttgca     240
aatgcaggaa atttagaaga tctgatgtca acatcacta atagaagtga tatcaatgat     300
acagggttct tcatgaatct ggaggaagac atgaccagat atgcctatta ttacagtgga     360
attggtgctg gggtgctggt tgctgcttac attcaggttt cattttggtg cctggcagct     420
ggaagacaaa tacacaaaat tagaaaacag ttttttcatg ctataatgcg acaggagata     480
ggctggtttg atgtgcacga tgttggggag cttaacaccc gacttacaga tgatgtctct     540
aagattaatg aagttattgg tgacaaaatt ggaatgttct ttcagtcaat ggcaacattt     600
ttcactgggt ttatagtagg atttacacgt ggttggaagc taccettgt gattttggcc     660 atcagtcctg ttcttggact gtcagctgct gtctgggcaa agatactatc ttcatttact     720
gataaagaac tctagcgta tgcaaaagct ggagcagtag ctgaagaggt cttggcagca     780 attgaactg tgattgcatt tggaggacaa aagaagaac ttgaaaggta caacaaaaat     840
```

```
ttagaagaag ctaaaagaat tgggataaag aaagctatta cagccaatat ttctataggt    900
gctgctttcc tgctgatcta tgcatcttat gctctggcct tctggtatgg gaccaccttg    960
gtcctctcag gggaatattc tattggacaa gtactcactg tattcttttc tgtattaatt   1020
ggggctttta gtgttggaca ggcatctcca agcattgaag catttgcaaa tgcaagagga   1080
gcagcttatg aaatcttcaa gataattgat aataagccaa gtattgacag ctattcgaag   1140
agtgggcaca aaccagataa tattaaggga aatttggaat tcagaaatgt tcacttcagt   1200
tacccatctc gaaaagaagt taagatcttg aagggcctga acctgaaggt gcagagtggg   1260
cagacggtgg ccctggttgg aaacagtggc tgtgggaaga gcacaacagt ccagctgatg   1320
cagaggctct atgaccccac agaggggatg gtcagtgttg atggacagga tattaggacc   1380
ataaatgtaa ggtttctacg ggaaatcatt ggtgtggtga gtcaggaacc tgtattgttt   1440
gccaccacga tagctgaaaa cattcgctat ggccgtgaaa atgtcaccat ggatgagatt   1500
gagaaagctg tcaaggaagc caatgcctat gactttatca tgaaactgcc tcataaattt   1560
gacaccctgg ttggagagag aggggcccag ttgagtggtg gcagaagca gaggatcgcc   1620
attgcacgtg ccctggttcg caaccccaag atcctcctgc tggatgaggc cacgtcagcc   1680
ttggacacag aaagcgaagc agtggttcag gtggctctgg ataaggccag aaaaggtcgg   1740
accaccattg tgatagctca tcgtttgtct acagttcgta atgctgacgt catcgctggt   1800
ttcgatgatg gagtcattgt ggagaaagga atcatgatg aactcatgaa agagaaaggc   1860
atttacttca aacttgtcac aatgcagaca gcaggaaatg aagttgaatt agaaaatgca   1920
gctgatgaat ccaaaagtga aattgatgcc ttgaaatgt cttcaaatga ttcaagatcc   1980
agtctaataa gaaaaagatc aactcgtagg agtgtccgtg gatcacaagc ccaagacaga   2040
aagcttagta ccaaagaggc tctggatgaa agtataccct cagtttcctt ttggaggatt   2100
atgaagctaa atttaactga atggcctat tttgttgttg gtgtatttg tgccattata   2160
aatggaggcc tgcaaccagc atttgcaata atattttcaa agattatagg gttttttaca   2220
agaattgatg atcctgaaac aaaacgacag aatagtaact tgttttcact attgtttcta   2280
gcccttggaa ttatttctt tattacattt ttccttcaag gtttcacatt tggcaaagct   2340
ggagagatcc tcaccaagcg gctccgatac atggttttcc gatccatgct cagacaggat   2400
gtgagttggt ttgatgaccc taaaaacacc actggagcat tgactaccag gctcgccaat   2460
gatgctgctc aagttaaagg ggctataggt tccaggcttg ctgtaattac ccagaatata   2520
gcaaatcttg gacaggaat aattatatcc ttcatctatg gttggcaact aacactgtta   2580
ctcttagcaa ttgtacccat cattgcaata gcaggagttg ttgaaatgaa atgttgtct   2640
ggacaagcac tgaaagataa gaaagaacta gaaggtgctg ggaagatcgc tactgaagca   2700
atagaaaact tccgaaccgt tgtttctttg actcaggagc agaagtttga acatatgtat   2760
gctcagagtt tgcaggtacc atacagaaac tctttgagga aagcacacat ctttggaatt   2820
acatttcct tcacccaggc aatgatgtat ttttcctatg ctggatgttt ccggtttgga   2880
gcctacttgg tggcacataa actcatgagc tttgaggatg ttctgttagt attttcagct   2940
gttgtctttg gtgccatggc cgtgggcaa gtcagttcat tgctcctga ctatgccaaa   3000
gccaaaatat cagcagccca catcatcatg atcattgaaa aaacccctt gattgacagc   3060
tacagcacgg aaggcctaat gccgaacaca ttggaaggaa atgtcacatt tggtgaagtt   3120
gtattcaact atcccacccg accggacatc ccagtgcttc agggactgag cctggaggtg   3180
```

-continued

```
aagaagggcc agacgctggc tctggtgggc agcagtggct gtgggaagag cacagtggtc   3240
cagctcctgg agcggttcta cgacccttg gcagggaaag tgctgcttga tgcaaagaa     3300 ataaagcgac tgaatgttca gtggctccga gcacacctgg gcatcgtgtc ccaggagccc   3360
atcctgtttg actgcagcat tgctgagaac attgcctatg agacaacag ccgggtggtg    3420 tcacaggaag agatcgtgag ggcagcaaag gaggccaaca tacatgcctt catcgagtca   3480
ctgcctaata aatatagcac taaagtagga gacaaaggaa ctcagctctc tggtggccag   3540
aaacaacgca ttgccatagc tcgtgccctt gttagacagc tcatatttt gcttttggat    3600 gaagccacgt cagctctgga tacagaaagt gaaaaggttg tccaagaagc cctgacaaa    3660 gccagagaag gccgcacctg cattgtgatt gctcaccgcc tgtccaccat ccagaatgca   3720
gacttaatag tggtgtttca gaatggcaga gtcaaggagc atggcacgca tcagcagctg   3780
ctggcacaga aaggcatcta tttttcaatg gtcagtgtcc aggctggaac aaagcgccag   3840
tgaactctgg ttaactccac                                                3860
```

<210> SEQ ID NO 4
<211> LENGTH: 1280
<212> TYPE: PRT
<213> ORGANISM: Homo sapiens

<400> SEQUENCE: 4

```
Met Asp Leu Glu Gly Asp Arg Asn Gly Gly Ala Lys Lys Lys Asn Phe
1               5                   10                  15

Phe Lys Leu Asn Asn Lys Ser Glu Lys Asp Lys Glu Lys Lys Pro
            20                  25                  30

Thr Val Ser Val Phe Ser Met Phe Arg Tyr Ser Asn Trp Leu Asp Lys
        35                  40                  45

Leu Tyr Met Val Val Gly Thr Leu Ala Ala Ile Ile His Gly Ala Gly
    50                  55                  60

Leu Pro Leu Met Met Leu Val Phe Gly Glu Met Thr Asp Ile Phe Ala
65                  70                  75                  80

Asn Ala Gly Asn Leu Glu Asp Leu Met Ser Asn Ile Thr Asn Arg Ser
                85                  90                  95

Asp Ile Asn Asp Thr Gly Phe Phe Met Asn Leu Glu Glu Asp Met Thr
            100                 105                 110

Arg Tyr Ala Tyr Tyr Tyr Ser Gly Ile Gly Ala Gly Val Leu Val Ala
        115                 120                 125

Ala Tyr Ile Gln Val Ser Phe Trp Cys Leu Ala Ala Gly Arg Gln Ile
    130                 135                 140

His Lys Ile Arg Lys Gln Phe His Ala Ile Met Arg Gln Glu Ile
145                 150                 155                 160

Gly Trp Phe Asp Val His Asp Val Gly Glu Leu Asn Thr Arg Leu Thr
                165                 170                 175

Asp Asp Val Ser Lys Ile Asn Glu Val Ile Gly Asp Lys Ile Gly Met
            180                 185                 190

Phe Phe Gln Ser Met Ala Thr Phe Phe Thr Gly Phe Ile Val Gly Phe
        195                 200                 205

Thr Arg Gly Trp Lys Leu Thr Leu Val Ile Leu Ala Ile Ser Pro Val
    210                 215                 220

Leu Gly Leu Ser Ala Ala Val Trp Ala Lys Ile Leu Ser Ser Phe Thr
225                 230                 235                 240

Asp Lys Glu Leu Leu Ala Tyr Ala Lys Ala Gly Ala Val Ala Glu Glu
                245                 250                 255
```

```
Val Leu Ala Ala Ile Arg Thr Val Ile Ala Phe Gly Gly Gln Lys Lys
            260                 265                 270

Glu Leu Glu Arg Tyr Asn Lys Asn Leu Glu Glu Ala Lys Arg Ile Gly
        275                 280                 285

Ile Lys Lys Ala Ile Thr Ala Asn Ile Ser Ile Gly Ala Ala Phe Leu
    290                 295                 300

Leu Ile Tyr Ala Ser Tyr Ala Leu Ala Phe Trp Tyr Gly Thr Thr Leu
305                 310                 315                 320

Val Leu Ser Gly Glu Tyr Ser Ile Gly Gln Val Leu Thr Val Phe Phe
                325                 330                 335

Ser Val Leu Ile Gly Ala Phe Ser Val Gly Gln Ala Ser Pro Ser Ile
            340                 345                 350

Glu Ala Phe Ala Asn Ala Arg Gly Ala Ala Tyr Glu Ile Phe Lys Ile
        355                 360                 365

Ile Asp Asn Lys Pro Ser Ile Asp Ser Tyr Ser Lys Ser Gly His Lys
    370                 375                 380

Pro Asp Asn Ile Lys Gly Asn Leu Glu Phe Arg Asn Val His Phe Ser
385                 390                 395                 400

Tyr Pro Ser Arg Lys Glu Val Lys Ile Leu Lys Gly Leu Asn Leu Lys
                405                 410                 415

Val Gln Ser Gly Gln Thr Val Ala Leu Val Gly Asn Ser Gly Cys Gly
            420                 425                 430

Lys Ser Thr Thr Val Gln Leu Met Gln Arg Leu Tyr Asp Pro Thr Glu
        435                 440                 445

Gly Met Val Ser Val Asp Gly Gln Asp Ile Arg Thr Ile Asn Val Arg
    450                 455                 460

Phe Leu Arg Glu Ile Ile Gly Val Val Ser Gln Glu Pro Val Leu Phe
465                 470                 475                 480

Ala Thr Thr Ile Ala Glu Asn Ile Arg Tyr Gly Arg Glu Asn Val Thr
                485                 490                 495

Met Asp Glu Ile Glu Lys Ala Val Lys Glu Ala Asn Ala Tyr Asp Phe
            500                 505                 510

Ile Met Lys Leu Pro His Lys Phe Asp Thr Leu Val Gly Glu Arg Gly
        515                 520                 525

Ala Gln Leu Ser Gly Gly Gln Lys Gln Arg Ile Ala Ile Ala Arg Ala
    530                 535                 540

Leu Val Arg Asn Pro Lys Ile Leu Leu Leu Asp Glu Ala Thr Ser Ala
545                 550                 555                 560

Leu Asp Thr Glu Ser Glu Ala Val Val Gln Val Ala Leu Asp Lys Ala
                565                 570                 575

Arg Lys Gly Arg Thr Thr Ile Val Ile Ala His Arg Leu Ser Thr Val
            580                 585                 590

Arg Asn Ala Asp Val Ile Ala Gly Phe Asp Asp Gly Val Ile Val Glu
        595                 600                 605

Lys Gly Asn His Asp Glu Leu Met Lys Glu Lys Gly Ile Tyr Phe Lys
    610                 615                 620

Leu Val Thr Met Gln Thr Ala Gly Asn Glu Val Glu Leu Glu Asn Ala
625                 630                 635                 640

Ala Asp Glu Ser Lys Ser Glu Ile Asp Ala Leu Glu Met Ser Ser Asn
                645                 650                 655

Asp Ser Arg Ser Ser Leu Ile Arg Lys Arg Ser Thr Arg Arg Ser Val
            660                 665                 670
```

-continued

```
Arg Gly Ser Gln Ala Gln Asp Arg Lys Leu Ser Thr Lys Glu Ala Leu
            675                 680                 685

Asp Glu Ser Ile Pro Pro Val Ser Phe Trp Arg Ile Met Lys Leu Asn
        690                 695                 700

Leu Thr Glu Trp Pro Tyr Phe Val Val Gly Val Phe Cys Ala Ile Ile
705                 710                 715                 720

Asn Gly Gly Leu Gln Pro Ala Phe Ala Ile Ile Phe Ser Lys Ile Ile
                725                 730                 735

Gly Val Phe Thr Arg Ile Asp Asp Pro Glu Thr Lys Arg Gln Asn Ser
            740                 745                 750

Asn Leu Phe Ser Leu Leu Phe Leu Ala Leu Gly Ile Ile Ser Phe Ile
        755                 760                 765

Thr Phe Phe Leu Gln Gly Phe Thr Phe Gly Lys Ala Gly Glu Ile Leu
770                 775                 780

Thr Lys Arg Leu Arg Tyr Met Val Phe Arg Ser Met Leu Arg Gln Asp
785                 790                 795                 800

Val Ser Trp Phe Asp Asp Pro Lys Asn Thr Thr Gly Ala Leu Thr Thr
                805                 810                 815

Arg Leu Ala Asn Asp Ala Ala Gln Val Lys Gly Ala Ile Gly Ser Arg
            820                 825                 830

Leu Ala Val Ile Thr Gln Asn Ile Ala Asn Leu Gly Thr Gly Ile Ile
        835                 840                 845

Ile Ser Phe Ile Tyr Gly Trp Gln Leu Thr Leu Leu Leu Leu Ala Ile
850                 855                 860

Val Pro Ile Ile Ala Ile Ala Gly Val Val Glu Met Lys Met Leu Ser
865                 870                 875                 880

Gly Gln Ala Leu Lys Asp Lys Lys Glu Leu Glu Gly Ala Gly Lys Ile
                885                 890                 895

Ala Thr Glu Ala Ile Glu Asn Phe Arg Thr Val Val Ser Leu Thr Gln
            900                 905                 910

Glu Gln Lys Phe Glu His Met Tyr Ala Gln Ser Leu Gln Val Pro Tyr
        915                 920                 925

Arg Asn Ser Leu Arg Lys Ala His Ile Phe Gly Ile Thr Phe Ser Phe
        930                 935                 940

Thr Gln Ala Met Met Tyr Phe Ser Tyr Ala Gly Cys Phe Arg Phe Gly
945                 950                 955                 960

Ala Tyr Leu Val Ala His Lys Leu Met Ser Phe Glu Asp Val Leu Leu
                965                 970                 975

Val Phe Ser Ala Val Val Phe Gly Ala Met Ala Val Gly Gln Val Ser
            980                 985                 990

Ser Phe Ala Pro Asp Tyr Ala Lys Ala Lys Ile Ser Ala Ala His Ile
        995                 1000                1005

Ile Met Ile Ile Glu Lys Thr Pro Leu Ile Asp Ser Tyr Ser Thr
        1010                1015                1020

Glu Gly Leu Met Pro Asn Thr Leu Glu Gly Asn Val Thr Phe Gly
        1025                1030                1035

Glu Val Phe Asn Tyr Pro Thr Arg Pro Asp Ile Pro Val Leu
        1040                1045                1050

Gln Gly Leu Ser Leu Glu Val Lys Lys Gly Gln Thr Leu Ala Leu
        1055                1060                1065

Val Gly Ser Ser Gly Cys Gly Lys Ser Thr Val Val Gln Leu Leu
        1070                1075                1080

Glu Arg Phe Tyr Asp Pro Leu Ala Gly Lys Val Leu Leu Asp Gly
```

-continued

```
         1085                1090                1095

Lys Glu Ile Lys Arg Leu Asn Val Gln Trp Leu Arg Ala His Leu
   1100                1105                1110

Gly Ile Val Ser Gln Glu Pro Ile Leu Phe Asp Cys Ser Ile Ala
   1115                1120                1125

Glu Asn Ile Ala Tyr Gly Asp Asn Ser Arg Val Val Ser Gln Glu
   1130                1135                1140

Glu Ile Val Arg Ala Ala Lys Glu Ala Asn Ile His Ala Phe Ile
   1145                1150                1155

Glu Ser Leu Pro Asn Lys Tyr Ser Thr Lys Val Gly Asp Lys Gly
   1160                1165                1170

Thr Gln Leu Ser Gly Gly Gln Lys Gln Arg Ile Ala Ile Ala Arg
   1175                1180                1185

Ala Leu Val Arg Gln Pro His Ile Leu Leu Leu Asp Glu Ala Thr
   1190                1195                1200

Ser Ala Leu Asp Thr Glu Ser Glu Lys Val Val Gln Glu Ala Leu
   1205                1210                1215

Asp Lys Ala Arg Glu Gly Arg Thr Cys Ile Val Ile Ala His Arg
   1220                1225                1230

Leu Ser Thr Ile Gln Asn Ala Asp Leu Ile Val Val Phe Gln Asn
   1235                1240                1245

Gly Arg Val Lys Glu His Gly Thr His Gln Gln Leu Leu Ala Gln
   1250                1255                1260

Lys Gly Ile Tyr Phe Ser Met Val Ser Val Gln Ala Gly Thr Lys
   1265                1270                1275

Arg Gln
   1280

<210> SEQ ID NO 5
<211> LENGTH: 4189
<212> TYPE: DNA
<213> ORGANISM: Mus musculus

<400> SEQUENCE: 5
atggagtttg aagagaacct aagggaaga gcagacaaga acttctcgaa gatgggcaaa      60
aagagtaaaa aggagaagaa agaaaagaaa cctgctgttg gcgtatttgg gatgtttcgc    120
tatgcagatt ggctggacaa gctgtgcatg attctgggaa ctctcgctgc tattatccat    180
ggaacattac ttcccctctt gatgctggtg tttggaaaca tgacagatag ttttacaaaa    240
gcagaagcca gtattctgcc aagcattact aatcaaagtg acccaacag tactctgatc     300 atcagcaaca gcagtctgga ggaagagatg gccatatacg cctactatta caccgggatt    360
ggtgctggtg tgctcatagt tgcctacatc caggtttcac tttggtgcct ggcagctgga    420
agacagatac acaagattag cagaagtttt ttccatgcta taatgaatca ggagataggc    480
tggtttgatg tgcatgatgt tgggagctc aacacccggc tcacagatga tgtctccaaa    540
attaatgacg gaattggtga caaaattggg atgtttttc agtccataac acatttttta    600 gccggttta tcataggatt tataagtggt tggaagctaa cccttgtcat tttggctgtc    660
agccctctta ttggattgtc atctgctttg tgggcaaagg tattgacttc atttactaat    720
aaggaactcc aggcttatgc aaaagctgga gcagttgctg aagaagtctt agcagccatc    780
agaactgtga ttgcctttgg aggacaacag aaggaacttg aaaggtacaa taaaaattta    840
gaagaagcta aaaatgttgg cataaagaaa gctatcacag ccagcatttc gataggcatt    900
```

```
gcctacctgt tggtctatgc atcatatgca ctggcattct ggtatgggac atccttggtc      960
ctctcaaatg aatattctat tggagaagtg cttactgtct tcttctctat tttgttgggg     1020
acttttagta ttggacactt ggccccaaac atagaagcct tgcaaacgc acaggggca       1080
gcctttgaaa tcttcaagat aattgataac gagccaagca ttgacagctt ctcaacaaag     1140
ggctacaaac cagacagtat aatgggaaac ttagagttta aaaatgttca cttcaactac     1200
ccatcgagaa gcgaagttca gatcttgaag ggcctcaatc tgaaggtgaa gagcggacag     1260
acggtggcct tggttggcaa cagtggctgt ggaaaaagca caactgtcca gctgatgcag     1320
aggctctacg acccctgga gggcgtggtc agtatcgacg acaagacat cagaaccatc       1380
aatgtgaggt atctgaggga gatcattggt gtggtgagtc aggaacctgt gctgtttgcc     1440
accacgatcg ccgagaacat tcgctatggc cgagaagatg tcaccatgga tgagattgag     1500
aaagctgtca aggaagccaa tgcctatgac ttcatcatga aactgcccca ccaatttgac     1560
accctggttg gtgagagagg ggcgcagctg agtgggggac agaaacagag aatcgccatt     1620
gcccgggccc tggtccgcaa tcccaagatc cttttgttgg acgaggccac ctcagccctg     1680
gatacagaaa gtgaagctgt ggtgcaggcc gcactggata aggctagaga aggccggacc     1740
accattgtga tagctcatcg cttgtctaca gttcgtaatg ctgacgtcat tgctggtttt     1800
gatggtggtg tcattgtgga gcaaggaaat catgatgagc tcatgagaga aagggcatt      1860
tacttcaaac ttgtcatgac acagactaga ggaaatgaaa ttgaaccagg aaataatgct     1920
tatggatccc agagtgacac tgatgcttct gaactgactt cagaagaatc caatcacct      1980
ttaataagga gatcaattta cagaagtgtc cacagaaagc aagaccaaga gagaagactt     2040
agtatgaaag aggctgtgga tgaagatgtg cctctggttt ccttttggcg gatcctaaat     2100
ctaaatctaa gtgaatggcc ttatttactt gttggcgtac tttgcgctgt tataaatggg     2160
tgcatacaac cagtgtttgc catagtattt tcaaggattg tagggggtttt ttcaagagat    2220
gatgaccatg aaactaaacg acagaattgt aatttgtttt ccctgttctt tctggttatg    2280
gggctgattt cttttgttac atatttcttt cagggcttca catttggcaa agccggagag    2340
atcctcacca agcgagtccg atacatggtt ttcaaatcca tgctgagaca ggatataagc    2400
tggttcgatg accataagaa cagcactggc tcactgacca ccaggctcgc cagtgatgct    2460
tctagtgtta aggggcgat gggcgccagg cttgctgtag ttacccagaa tgtagcaaac     2520
ctcgggacag gagtcatcct ctccttagtc tatggctggc agctgacact tctacttgta    2580
gtaattatac cgctcattgt attgggcgga attattgaaa tgaagctgtt gtctggccaa    2640
gccttgaagg acaagaaaca gcttgagatc tctgggaaga ttgctacaga agcaattgaa    2700
aacttccgca ctattgtctc tttgactcgg gagcagaagt ttgaaccat gtatgcccag     2760
agcttgcagg taccatacag aaatgcgatg aagaaagcac acgtgtttgg gatcacgttc    2820
tccttcaccc aggccatgat gtatttttct tatgctgctt gtttccggtt cggtgcctac    2880
ttggtggcac aacaactcat gactttgaa aatgttatgt tggtatttc tgctgttgtc     2940
tttggtgcca tggcagctgg gaatactagt tcatttgctc ctgactatgc gaaagccaaa    3000
gtatcagcat ctcatatcat caggatcatt gagaaaaccc ctgagattga cagctacagc    3060
acagagggct tgaagcctac tctgttagaa ggaaatgtaa aatttaatgg agtccagttt    3120
aactatccca cccgacccaa catcccagtg cttcagggc tgagcctcga ggtgaagaag    3180
ggccagacgt tggcccctgt gggcagcagt ggctgtggga agagcacagt ggtccagctg    3240
ctcgagcgct tctacgaccc catggctgga tcagtgtttc tagatggcaa agaaataaag    3300
```

```
caactgaatg tccagtggct ccgagctcac cttggcattg tgtcccagga gcccattctc   3360
tttgactgca gcattgcaga gaacatcgcc tatggagaca acagccgggc cgtgtctcat   3420
gaggagattg tgagggcagc caaggaggcc aacatccacc agttcatcga ctcactgcct   3480
gataaataca acaccagagt aggagacaaa ggcactcagc tgtcgggtgg cagaagcag    3540 cgcatcgcca tcgcacgtgc cctcgtcaga cagcctcaca ttttacttct ggacgaagca   3600
acatcagctc tggatacaga aagtgaaaag gttgtccagg aagcgctgga caaagccagg   3660
gaaggccgca cctgcattgt gatcgctcac cgcctgtcca ccatccagaa cgcggacttg   3720
atcgtggtga ttgagaacgg caaagtcaag gagcacggcc cccaccagca gctgctggcg   3780
cagaagggca tctacttctc aatggtccag gctggagcaa agcgctcatg agctgtgact   3840
atctgaggtg ctaagtattt ttaatattgg tgtttaaaca tggcaccaaa ccaaagttaa   3900
aaggcaaggg ctgttaaagg taactccatc aagatgagaa gccttccgag actttgtaat   3960
taaatgaacc aaaatcggaa acaaacaaac aaacaaacaa acaagccata gttaaacagg   4020
gccatgtttt taattgcatt acgtgattca taagagaaca tatagttttt taaaataaaa   4080
tgtataattt tgtttcagtt tttaatttct accctacttt cttaaatgat tataaagatt   4140
gtaaaaagca ctatttctta aattgcctat aaaaattaaa ttttcatat              4189
```

<210> SEQ ID NO 6
<211> LENGTH: 1276
<212> TYPE: PRT
<213> ORGANISM: Mus musculus

<400> SEQUENCE: 6

```
Met Glu Phe Glu Glu Asn Leu Lys Gly Arg Ala Asp Lys Asn Phe Ser
1               5                   10                  15

Lys Met Gly Lys Lys Ser Lys Lys Glu Lys Lys Glu Lys Lys Pro Ala
            20                  25                  30

Val Gly Val Phe Gly Met Phe Arg Tyr Ala Asp Trp Leu Asp Lys Leu
        35                  40                  45

Cys Met Ile Leu Gly Thr Leu Ala Ala Ile Ile His Gly Thr Leu Leu
    50                  55                  60

Pro Leu Leu Met Leu Val Phe Gly Asn Met Thr Asp Ser Phe Thr Lys
65                  70                  75                  80

Ala Glu Ala Ser Ile Leu Pro Ser Ile Thr Asn Gln Ser Gly Pro Asn
                85                  90                  95

Ser Thr Leu Ile Ile Ser Asn Ser Ser Leu Glu Glu Glu Met Ala Ile
            100                 105                 110

Tyr Ala Tyr Tyr Tyr Thr Gly Ile Gly Ala Gly Val Leu Ile Val Ala
        115                 120                 125

Tyr Ile Gln Val Ser Leu Trp Cys Leu Ala Ala Gly Arg Gln Ile His
    130                 135                 140

Lys Ile Arg Gln Lys Phe Phe His Ala Ile Met Asn Gln Glu Ile Gly
145                 150                 155                 160

Trp Phe Asp Val His Asp Val Gly Glu Leu Asn Thr Arg Leu Thr Asp
                165                 170                 175

Asp Val Ser Lys Ile Asn Asp Gly Ile Gly Asp Lys Ile Gly Met Phe
            180                 185                 190

Phe Gln Ser Ile Thr Thr Phe Leu Ala Gly Phe Ile Ile Gly Phe Ile
        195                 200                 205

Ser Gly Trp Lys Leu Thr Leu Val Ile Leu Ala Val Ser Pro Leu Ile
```

-continued

```
            210                 215                 220
Gly Leu Ser Ser Ala Leu Trp Ala Lys Val Leu Thr Ser Phe Thr Asn
225                 230                 235                 240

Lys Glu Leu Gln Ala Tyr Ala Lys Ala Gly Val Ala Glu Glu Val
                245                 250                 255

Leu Ala Ala Ile Arg Thr Val Ile Ala Phe Gly Gly Gln Gln Lys Glu
                260                 265                 270

Leu Glu Arg Tyr Asn Lys Asn Leu Glu Ala Lys Asn Val Gly Ile
            275                 280                 285

Lys Lys Ala Ile Thr Ala Ser Ile Ser Ile Gly Ile Ala Tyr Leu Leu
            290                 295                 300

Val Tyr Ala Ser Tyr Ala Leu Ala Phe Trp Tyr Gly Thr Ser Leu Val
305                 310                 315                 320

Leu Ser Asn Glu Tyr Ser Ile Gly Glu Val Leu Thr Val Phe Phe Ser
                325                 330                 335

Ile Leu Leu Gly Thr Phe Ser Ile Gly His Leu Ala Pro Asn Ile Glu
            340                 345                 350

Ala Phe Ala Asn Ala Arg Gly Ala Ala Phe Glu Ile Phe Lys Ile Ile
            355                 360                 365

Asp Asn Glu Pro Ser Ile Asp Ser Phe Ser Thr Lys Gly Tyr Lys Pro
370                 375                 380

Asp Ser Ile Met Gly Asn Leu Glu Phe Lys Asn Val His Phe Asn Tyr
385                 390                 395                 400

Pro Ser Arg Ser Glu Val Gln Ile Leu Lys Gly Leu Asn Leu Lys Val
                405                 410                 415

Lys Ser Gly Gln Thr Val Ala Leu Val Gly Asn Ser Gly Cys Gly Lys
                420                 425                 430

Ser Thr Thr Val Gln Leu Met Gln Arg Leu Tyr Asp Pro Leu Glu Gly
            435                 440                 445

Val Val Ser Ile Asp Gly Gln Asp Ile Arg Thr Ile Asn Val Arg Tyr
            450                 455                 460

Leu Arg Glu Ile Ile Gly Val Val Ser Gln Glu Pro Val Leu Phe Ala
465                 470                 475                 480

Thr Thr Ile Ala Glu Asn Ile Arg Tyr Gly Arg Glu Asp Val Thr Met
                485                 490                 495

Asp Glu Ile Glu Lys Ala Val Lys Glu Ala Asn Ala Tyr Asp Phe Ile
            500                 505                 510

Met Lys Leu Pro His Gln Phe Asp Thr Leu Val Gly Glu Arg Gly Ala
            515                 520                 525

Gln Leu Ser Gly Gly Gln Lys Gln Arg Ile Ala Ile Ala Arg Ala Leu
            530                 535                 540

Val Arg Asn Pro Lys Ile Leu Leu Leu Asp Glu Ala Thr Ser Ala Leu
545                 550                 555                 560

Asp Thr Glu Ser Glu Ala Val Val Gln Ala Leu Asp Lys Ala Arg
                565                 570                 575

Glu Gly Arg Thr Thr Ile Val Ile Ala His Arg Leu Ser Thr Val Arg
                580                 585                 590

Asn Ala Asp Val Ile Ala Gly Phe Asp Gly Gly Val Ile Val Glu Gln
            595                 600                 605

Gly Asn His Asp Glu Leu Met Arg Glu Lys Gly Ile Tyr Phe Lys Leu
            610                 615                 620

Val Met Thr Gln Thr Arg Gly Asn Glu Ile Glu Pro Gly Asn Asn Ala
625                 630                 635                 640
```

```
Tyr Gly Ser Gln Ser Asp Thr Asp Ala Ser Glu Leu Thr Ser Glu Glu
                645                 650                 655

Ser Lys Ser Pro Leu Ile Arg Arg Ser Ile Tyr Arg Ser Val His Arg
                660                 665                 670

Lys Gln Asp Gln Glu Arg Arg Leu Ser Met Lys Glu Ala Val Asp Glu
                675                 680                 685

Asp Val Pro Leu Val Ser Phe Trp Arg Ile Leu Asn Leu Asn Leu Ser
        690                 695                 700

Glu Trp Pro Tyr Leu Leu Val Gly Val Leu Cys Ala Val Ile Asn Gly
705                 710                 715                 720

Cys Ile Gln Pro Val Phe Ala Ile Val Phe Ser Arg Ile Val Gly Val
                725                 730                 735

Phe Ser Arg Asp Asp Asp His Glu Thr Lys Arg Gln Asn Cys Asn Leu
                740                 745                 750

Phe Ser Leu Phe Phe Leu Val Met Gly Leu Ile Ser Phe Val Thr Tyr
                755                 760                 765

Phe Phe Gln Gly Phe Thr Phe Gly Lys Ala Gly Glu Ile Leu Thr Lys
        770                 775                 780

Arg Val Arg Tyr Met Val Phe Lys Ser Met Leu Arg Gln Asp Ile Ser
785                 790                 795                 800

Trp Phe Asp Asp His Lys Asn Ser Thr Gly Ser Leu Thr Thr Arg Leu
                805                 810                 815

Ala Ser Asp Ala Ser Ser Val Lys Gly Ala Met Gly Ala Arg Leu Ala
                820                 825                 830

Val Val Thr Gln Asn Val Ala Asn Leu Gly Thr Gly Val Ile Leu Ser
        835                 840                 845

Leu Val Tyr Gly Trp Gln Leu Thr Leu Leu Leu Val Val Ile Ile Pro
        850                 855                 860

Leu Ile Val Leu Gly Gly Ile Glu Met Lys Leu Leu Ser Gly Gln
865                 870                 875                 880

Ala Leu Lys Asp Lys Lys Gln Leu Glu Ile Ser Gly Lys Ile Ala Thr
                885                 890                 895

Glu Ala Ile Glu Asn Phe Arg Thr Ile Val Ser Leu Thr Arg Glu Gln
                900                 905                 910

Lys Phe Glu Thr Met Tyr Ala Gln Ser Leu Gln Val Pro Tyr Arg Asn
                915                 920                 925

Ala Met Lys Lys Ala His Val Phe Gly Ile Thr Phe Ser Phe Thr Gln
                930                 935                 940

Ala Met Met Tyr Phe Ser Tyr Ala Ala Cys Phe Arg Phe Gly Ala Tyr
945                 950                 955                 960

Leu Val Ala Gln Gln Leu Met Thr Phe Glu Asn Val Met Leu Val Phe
                965                 970                 975

Ser Ala Val Val Phe Gly Ala Met Ala Ala Gly Asn Thr Ser Ser Phe
                980                 985                 990

Ala Pro Asp Tyr Ala Lys Ala Lys Val Ser Ala Ser His Ile Ile Arg
        995                 1000                1005

Ile Ile Glu Lys Thr Pro Glu Ile Asp Ser Tyr Ser Thr Glu Gly
        1010                1015                1020

Leu Lys Pro Thr Leu Leu Glu Gly Asn Val Lys Phe Asn Gly Val
        1025                1030                1035

Gln Phe Asn Tyr Pro Thr Arg Pro Asn Ile Pro Val Leu Gln Gly
        1040                1045                1050
```

```
Leu Ser Leu Glu Val Lys Lys Gly Gln Thr Leu Ala Leu Val Gly
    1055                1060                1065

Ser Ser Gly Cys Gly Lys Ser Thr Val Val Gln Leu Leu Glu Arg
    1070                1075                1080

Phe Tyr Asp Pro Met Ala Gly Ser Val Phe Leu Asp Gly Lys Glu
    1085                1090                1095

Ile Lys Gln Leu Asn Val Gln Trp Leu Arg Ala His Leu Gly Ile
    1100                1105                1110

Val Ser Gln Glu Pro Ile Leu Phe Asp Cys Ser Ile Ala Glu Asn
    1115                1120                1125

Ile Ala Tyr Gly Asp Asn Ser Arg Ala Val Ser His Glu Glu Ile
    1130                1135                1140

Val Arg Ala Ala Lys Glu Ala Asn Ile His Gln Phe Ile Asp Ser
    1145                1150                1155

Leu Pro Asp Lys Tyr Asn Thr Arg Val Gly Asp Lys Gly Thr Gln
    1160                1165                1170

Leu Ser Gly Gly Gln Lys Gln Arg Ile Ala Ile Ala Arg Ala Leu
    1175                1180                1185

Val Arg Gln Pro His Ile Leu Leu Leu Asp Glu Ala Thr Ser Ala
    1190                1195                1200

Leu Asp Thr Glu Ser Glu Lys Val Val Gln Glu Ala Leu Asp Lys
    1205                1210                1215

Ala Arg Glu Gly Arg Thr Cys Ile Val Ile Ala His Arg Leu Ser
    1220                1225                1230

Thr Ile Gln Asn Ala Asp Leu Ile Val Val Ile Glu Asn Gly Lys
    1235                1240                1245

Val Lys Glu His Gly Thr His Gln Gln Leu Leu Ala Gln Lys Gly
    1250                1255                1260

Ile Tyr Phe Ser Met Val Gln Ala Gly Ala Lys Arg Ser
    1265                1270                1275

<210> SEQ ID NO 7
<211> LENGTH: 4788
<212> TYPE: DNA
<213> ORGANISM: Mus musculus

<400> SEQUENCE: 7
atggaacttg aagaggacct aagggaaga gcagacaaga acttctcaaa gatgggcaaa       60
aagagtaaaa aggagaagaa agaaaagaaa ccagcagtca gtgtgcttac aatgtttcgt      120
tatgcaggtt ggctagacag gttgtacatg ctggtgggaa ctctggctgc tattatccat      180
ggagtggcgc tcccacttat gatgctgatc tttggtgaca tgacagatag ctttgcaagt     240
gtaggaaacg tctctaaaaa cagtactaat atgagtgagg ccgataaaag agccatgttt     300
gccaaactgg aggaagaaat gaccacgtac gcctactatt acaccgggat tggtgctggt     360
gtgctcatag ttgcctacat ccaggttcca ttttggtgcc tggcagctgg aagacagata     420
cacaagatca ggcagaagtt ttttcatgct ataatgaatc aggagatagg ctggtttgat     480
gtgcatgacg ttggggagct caacacccgg ctcacagatg atgtttccaa aattaatgaa     540
ggaattggtg acaaaatcgg aatgttcttc caggcaatgg caacattttt tggtggtttt     600
ataataggat ttacccgtgg ctggaagcta accccttgtga ttttgccat cagccctgtt     660 cttggactgt cagctggtat ttgggcaaag atattgtctt catttactga taaggaactc     720
catgcttatg caaaagctgg agcagttgct gaagaagtct tagcagccat cagaactgtg     780
```

-continued

```
attgcgtttg gaggacaaaa gaaggaactt gaaaggtaca ataacaactt ggaagaagct       840
aaaaggctgg ggataaagaa agctatcacg gccaacatct ccatgggtgc agcttttctc       900
cttatctatg catcatatgc tctggcattc tggtatggga cttccttggt catctccaaa       960
gaatactcta ttggacaagt gctcactgtc ttcttttccg tgttaattgg agcattcagt      1020
gttggacagg catctccaaa tattgaagcc ttcgccaatg cacgaggagc agcttatgaa      1080
gtcttcaaaa taattgataa taagcccagt atagacagct tctcaaagag tgggcacaaa      1140
ccagacaaca tacaaggaaa tctggaattt aagaatattc acttcagtta cccatctcga      1200
aaagaagttc agatcttgaa gggcctcaat ctgaaggtga agagcggaca gacggtggcc      1260
ctggttggca acagtggctg tggaaaaagc acaactgtcc agctgatgca aaggctctac      1320 gacccctag atggcatggt cagtatcgac ggacaggaca tcagaaccat caatgtgagg       1380
tatctgaggg agatcattgg tgtggtgagt caggaacctg tgctgtttgc caccacgatc      1440
gccgagaaca ttcgctatgg ccgagaagat gtcaccatgg atgagattga aaagctgtc       1500 aaggaagcca atgcctatga cttcatcatg aaactgcccc accaatttga caccctggtt      1560
ggtgagagag gggcgcacgt gagtggggga cagaaacaga gaatcgccat tgcccgggcc      1620
ctggtccgca atcccaagat cctttttgttg gacgaggcca cctcagccct ggatacagaa      1680
agtgaagctg tggttcaggc cgcactggat aaggctagag aaggccggac caccattgtg      1740
atagctcatc gcttgtctac cgttcgtaat gctgacgtca ttgctggttt tgatggtggt      1800
gtcattgtgg agcaaggaaa tcatgatgag ctcatgagag aaaagggcat ttacttcaaa      1860
cttgtcatga cacagacagc aggaaatgaa attgaattag gaaatgaagc ttgtaaatct      1920
aaggatgaaa ttgataattt agacatgtct tcaaaagatt caggatccag tctaataaga      1980
agaagatcaa ctcgcaaaag catctgtgga ccacatgacc aagacaggaa gcttagtacc      2040
aaagaggccc tggatgaaga tgtacctcca gcttccttttt ggcggatcct gaagttgaat      2100
tcaactgaat ggccttattt tgtggttggt atattctgtg ccataataaa tggaggctta      2160
cagccagcat tctccgtaat attttcaaaa gttgtagggg ttttttacaaa tggtggcccc      2220 cctgaaaccc agcggcagaa cagcaacttg ttttccttgt tgtttctgat ccttgggatc      2280
atttctttca ttacattttt tcttcagggc ttcacatttg gcaaagctgg agagatcctc      2340
accaagcgac tccgatacat ggttttcaaa tccatgctga acaggatgt gagctggttt       2400 gatgacccta aaacaccac cggagcactg accaccaggc tcgccaacga tgctgctcaa      2460
gtgaaagggg ctacagggtc taggcttgct gtgattttcc agaacatagc aaatcttggg      2520
acaggaatca tcatatccct aatctatggc tggcaactaa cactttttact cttagcaatt      2580 gtacccatca ttgcgatagc tggagtggtt gaaatgaaaa tgttgtctgg acaagcactg      2640
aaagataaga aggaactaga aggttctgga aagattgcta cggaagcaat tgaaaacttc      2700
cgcactgttg tctctttgac tcgggagcag aagtttgaaa ccatgtatgc ccagagcttg      2760
cagataccat acagaaatgc gatgaagaaa gcacacgtgt ttgggatcac gttctccttc      2820
acccaggcca tgatgtattt ttcttatgct gcttgtttcc ggttcggtgc ctacttggtg      2880
acacaacaac tcatgactttt tgaaaatgtt ctgttagtat tctcagctat tgtctttggt      2940
gccatggcag tggggcaggt cagttcattc gctcctgact atgcgaaagc aacagtgtca      3000
gcatcccaca tcatcaggat cattgagaaa accccccgaga ttgacagcta cagcacgcaa      3060
ggcctaaagc cgaatatgtt ggaaggaaat gtgcaattta tgtggagtcgt gttcaactat      3120 cccacccgac ccagcatccc agtgcttcag gggctgagcc ttgaggtgaa gaagggccag      3180
```

-continued

```
acgctggccc tggtgggcag cagtggctgc gggaagagca cagtggtcca gctgctcgag   3240
cgcttctacg accccatggc tggatcagtg tttctagatg gcaaagaaat aaagcaactg   3300
aatgtccagt ggctccgagc acagctgggc attgtgtccc aagagcccat tctctttgac   3360
tgcagcatcg cagagaacat tgcctacgga gacaacagcc gggtcgtgtc ttatgaggag   3420
attgtgaggg cagccaagga ggccaacatc caccagttca tcgactcgct acctgataaa   3480
tacaacacca gagtaggaga caaaggcact cagctgtcgg gtgggcagaa gcagcgcatc   3540
gccatcgcac gcgccctcgt cagacagcct cacattttac ttctggacga agcaacatca   3600
gctctggata cagaaagtga aaaggttgtc caggaagcgc tggacaaagc cagggaaggc   3660
cgcacctgca ttgtgatcgc tcaccgcctg tccaccatcc agaacgcgga cttgatcgtg   3720
gtgattcaga acggcaaggt caaggagcac ggcacccacc agcagctgct ggcgcagaag   3780
ggcatctact tctcaatggt cagtgtgcag gctggagcaa agcgctcatg aactgtgacc   3840
atgtaagatg ttaagtattt ttattgtttg tattcatata tggtgtttaa tccaagtcaa   3900
aaggaaaaca cttactaaaa tagccagtta tctattttct gccacagtgg aaagcattta   3960
gtttggttta gagtcttcag aggctttgta attaaaaaaa caaaaataga tacagcatca   4020
aatggagatt aatgctttaa aatgcactat aaaatttata aaagggttaa aagtgaatgt   4080
ttgataatat atactttat  ttatactttc tcatttgtaa ctataactga tttctgctta   4140
acaaattatg tatgtatcaa aaattactga aatgtttgta taaagtatat atagtgaaac   4200
tgagcattca tattttgag  ttattttgct caaatgcatg cgaaattata tattgtccca   4260
actgggatat tgtacataat tttagccttt aaaaaacagt ccattactgg ggggagggggg   4320
catcactcta tgggcaaagt gttactcaga catgggcacc tgagttcaga tccctaccac   4380
ctaagtaagc agacaaggtg tggtgttttt gtaatgccag tgctagaggc agaaaagaca   4440
gatcctgcag gctcagtggc tggccaaaca gcctagccaa catagcgcgt tccaggttca   4500
gtgagaaaac ttgtctcaaa aatcagaggg aaaagcaaat gaggtgtcag ccatgtgcac   4560
tcatgcaaat gccatacatg cagaagtatg tgcacacaca cgcacacatt aaccaacgac   4620
tagcaaggaa aatgaaggtg gataagaggg gtgggactgg acaaaggag  ggtacctgga   4680
tgaatatgac tgaaggacgt tatgtacaca tatgaaaacg tcgtactgaa actcactaca   4740
atgtatactt aatatattgc taataaaata ttttttaaaag aaaaaaat             4788
```

<210> SEQ ID NO 8
<211> LENGTH: 1276
<212> TYPE: PRT
<213> ORGANISM: Mus musculus
<400> SEQUENCE: 8

```
Met Glu Leu Glu Glu Asp Leu Lys Gly Arg Ala Asp Lys Asn Phe Ser
1               5                   10                  15

Lys Met Gly Lys Lys Ser Lys Lys Glu Lys Lys Glu Lys Lys Pro Ala
            20                  25                  30

Val Ser Val Leu Thr Met Phe Arg Tyr Ala Gly Trp Leu Asp Arg Leu
        35                  40                  45

Tyr Met Leu Val Gly Thr Leu Ala Ala Ile Ile His Gly Val Ala Leu
    50                  55                  60

Pro Leu Met Met Leu Ile Phe Gly Asp Met Thr Asp Ser Phe Ala Ser
65                  70                  75                  80

Val Gly Asn Val Ser Lys Asn Ser Thr Asn Met Ser Glu Ala Asp Lys
```

-continued

```
                85                  90                  95
Arg Ala Met Phe Ala Lys Leu Glu Glu Met Thr Thr Tyr Ala Tyr
            100                 105                 110
Tyr Tyr Thr Gly Ile Gly Ala Gly Val Leu Ile Val Ala Tyr Ile Gln
            115                 120                 125
Val Ser Phe Trp Cys Leu Ala Ala Gly Arg Gln Ile His Lys Ile Arg
            130                 135                 140
Gln Lys Phe Phe His Ala Ile Met Asn Gln Glu Ile Gly Trp Phe Asp
145                 150                 155                 160
Val His Asp Val Gly Glu Leu Asn Thr Arg Leu Thr Asp Asp Val Ser
            165                 170                 175
Lys Ile Asn Glu Gly Ile Gly Asp Lys Ile Gly Met Phe Phe Gln Ala
            180                 185                 190
Met Ala Thr Phe Phe Gly Gly Phe Ile Ile Gly Phe Thr Arg Gly Trp
            195                 200                 205
Lys Leu Thr Leu Val Ile Leu Ala Ile Ser Pro Val Leu Gly Leu Ser
            210                 215                 220
Ala Gly Ile Trp Ala Lys Ile Leu Ser Ser Phe Thr Asp Lys Glu Leu
225                 230                 235                 240
His Ala Tyr Ala Lys Ala Gly Ala Val Ala Glu Glu Val Leu Ala Ala
            245                 250                 255
Ile Arg Thr Val Ile Ala Phe Gly Gly Gln Lys Lys Glu Leu Glu Arg
            260                 265                 270
Tyr Asn Asn Asn Leu Glu Glu Ala Lys Arg Leu Gly Ile Lys Lys Ala
            275                 280                 285
Ile Thr Ala Asn Ile Ser Met Gly Ala Ala Phe Leu Leu Ile Tyr Ala
            290                 295                 300
Ser Tyr Ala Leu Ala Phe Trp Tyr Gly Thr Ser Leu Val Ile Ser Lys
305                 310                 315                 320
Glu Tyr Ser Ile Gly Gln Val Leu Thr Val Phe Phe Ser Val Leu Ile
            325                 330                 335
Gly Ala Phe Ser Val Gly Gln Ala Ser Pro Asn Ile Glu Ala Phe Ala
            340                 345                 350
Asn Ala Arg Gly Ala Ala Tyr Glu Val Phe Lys Ile Ile Asp Asn Lys
            355                 360                 365
Pro Ser Ile Asp Ser Phe Ser Lys Ser Gly His Lys Pro Asp Asn Ile
            370                 375                 380
Gln Gly Asn Leu Glu Phe Lys Asn Ile His Phe Ser Tyr Pro Ser Arg
385                 390                 395                 400
Lys Glu Val Gln Ile Leu Lys Gly Leu Asn Leu Lys Val Lys Ser Gly
            405                 410                 415
Gln Thr Val Ala Leu Val Gly Asn Ser Gly Cys Gly Lys Ser Thr Thr
            420                 425                 430
Val Gln Leu Met Gln Arg Leu Tyr Asp Pro Leu Asp Gly Met Val Ser
            435                 440                 445
Ile Asp Gly Gln Asp Ile Arg Thr Ile Asn Val Arg Tyr Leu Arg Glu
            450                 455                 460
Ile Ile Gly Val Val Ser Gln Glu Pro Val Leu Phe Ala Thr Thr Ile
465                 470                 475                 480
Ala Glu Asn Ile Arg Tyr Gly Arg Glu Asp Val Thr Met Asp Glu Ile
            485                 490                 495
Glu Lys Ala Val Lys Glu Ala Asn Ala Tyr Asp Phe Ile Met Lys Leu
            500                 505                 510
```

-continued

```
Pro His Gln Phe Asp Thr Leu Val Gly Glu Arg Gly Ala His Val Ser
        515                 520                 525
Gly Gly Gln Lys Gln Arg Ile Ala Ile Ala Arg Ala Leu Val Arg Asn
    530                 535                 540
Pro Lys Ile Leu Leu Leu Asp Glu Ala Thr Ser Ala Leu Asp Thr Glu
545                 550                 555                 560
Ser Glu Ala Val Val Gln Ala Ala Leu Asp Lys Ala Arg Glu Gly Arg
                565                 570                 575
Thr Thr Ile Val Ile Ala His Arg Leu Ser Thr Val Arg Asn Ala Asp
                580                 585                 590
Val Ile Ala Gly Phe Asp Gly Gly Val Ile Val Glu Gln Gly Asn His
            595                 600                 605
Asp Glu Leu Met Arg Glu Lys Gly Ile Tyr Phe Lys Leu Val Met Thr
        610                 615                 620
Gln Thr Ala Gly Asn Glu Ile Glu Leu Gly Asn Glu Ala Cys Lys Ser
625                 630                 635                 640
Lys Asp Glu Ile Asp Asn Leu Asp Met Ser Ser Lys Asp Ser Gly Ser
                645                 650                 655
Ser Leu Ile Arg Arg Ser Thr Arg Lys Ser Ile Cys Gly Pro His
                660                 665                 670
Asp Gln Asp Arg Lys Leu Ser Thr Lys Glu Ala Leu Asp Glu Asp Val
            675                 680                 685
Pro Pro Ala Ser Phe Trp Arg Ile Leu Lys Leu Asn Ser Thr Glu Trp
        690                 695                 700
Pro Tyr Phe Val Val Gly Ile Phe Cys Ala Ile Ile Asn Gly Gly Leu
705                 710                 715                 720
Gln Pro Ala Phe Ser Val Ile Phe Ser Lys Val Val Gly Val Phe Thr
                725                 730                 735
Asn Gly Gly Pro Pro Glu Thr Gln Arg Gln Asn Ser Asn Leu Phe Ser
            740                 745                 750
Leu Leu Phe Leu Ile Leu Gly Ile Ile Ser Phe Ile Thr Phe Phe Leu
        755                 760                 765
Gln Gly Phe Thr Phe Gly Lys Ala Gly Glu Ile Leu Thr Lys Arg Leu
    770                 775                 780
Arg Tyr Met Val Phe Lys Ser Met Leu Arg Gln Asp Val Ser Trp Phe
785                 790                 795                 800
Asp Asp Pro Lys Asn Thr Thr Gly Ala Leu Thr Thr Arg Leu Ala Asn
                805                 810                 815
Asp Ala Ala Gln Val Lys Gly Ala Thr Gly Ser Arg Leu Ala Val Ile
            820                 825                 830
Phe Gln Asn Ile Ala Asn Leu Gly Thr Gly Ile Ile Ile Ser Leu Ile
        835                 840                 845
Tyr Gly Trp Gln Leu Thr Leu Leu Leu Ala Ile Val Pro Ile Ile
    850                 855                 860
Ala Ile Ala Gly Val Val Glu Met Lys Met Leu Ser Gly Gln Ala Leu
865                 870                 875                 880
Lys Asp Lys Lys Glu Leu Glu Gly Ser Gly Lys Ile Ala Thr Glu Ala
                885                 890                 895
Ile Glu Asn Phe Arg Thr Val Val Ser Leu Thr Arg Glu Gln Lys Phe
            900                 905                 910
Glu Thr Met Tyr Ala Gln Ser Leu Gln Ile Pro Tyr Arg Asn Ala Met
        915                 920                 925
```

```
Lys Lys Ala His Val Phe Gly Ile Thr Phe Ser Phe Thr Gln Ala Met
        930                 935                 940

Met Tyr Phe Ser Tyr Ala Ala Cys Phe Arg Phe Gly Ala Tyr Leu Val
945                 950                 955                 960

Thr Gln Gln Leu Met Thr Phe Glu Asn Val Leu Leu Val Phe Ser Ala
                965                 970                 975

Ile Val Phe Gly Ala Met Ala Val Gly Gln Val Ser Ser Phe Ala Pro
            980                 985                 990

Asp Tyr Ala Lys Ala Thr Val Ser Ala Ser His Ile Ile Arg Ile Ile
        995                 1000                1005

Glu Lys Thr Pro Glu Ile Asp Ser Tyr Ser Thr Gln Gly Leu Lys
    1010                1015                1020

Pro Asn Met Leu Glu Gly Asn Val Gln Phe Ser Gly Val Val Phe
    1025                1030                1035

Asn Tyr Pro Thr Arg Pro Ser Ile Pro Val Leu Gln Gly Leu Ser
    1040                1045                1050

Leu Glu Val Lys Lys Gly Gln Thr Leu Ala Leu Val Gly Ser Ser
    1055                1060                1065

Gly Cys Gly Lys Ser Thr Val Val Gln Leu Leu Glu Arg Phe Tyr
    1070                1075                1080

Asp Pro Met Ala Gly Ser Val Phe Leu Asp Gly Lys Glu Ile Lys
    1085                1090                1095

Gln Leu Asn Val Gln Trp Leu Arg Ala Gln Leu Gly Ile Val Ser
    1100                1105                1110

Gln Glu Pro Ile Leu Phe Asp Cys Ser Ile Ala Glu Asn Ile Ala
    1115                1120                1125

Tyr Gly Asp Asn Ser Arg Val Val Ser Tyr Glu Glu Ile Val Arg
    1130                1135                1140

Ala Ala Lys Glu Ala Asn Ile His Gln Phe Ile Asp Ser Leu Pro
    1145                1150                1155

Asp Lys Tyr Asn Thr Arg Val Gly Asp Lys Gly Thr Gln Leu Ser
    1160                1165                1170

Gly Gly Gln Lys Gln Arg Ile Ala Ile Ala Arg Ala Leu Val Arg
    1175                1180                1185

Gln Pro His Ile Leu Leu Leu Asp Glu Ala Thr Ser Ala Leu Asp
    1190                1195                1200

Thr Glu Ser Glu Lys Val Val Gln Glu Ala Leu Asp Lys Ala Arg
    1205                1210                1215

Glu Gly Arg Thr Cys Ile Val Ile Ala His Arg Leu Ser Thr Ile
    1220                1225                1230

Gln Asn Ala Asp Leu Ile Val Val Ile Gln Asn Gly Lys Val Lys
    1235                1240                1245

Glu His Gly Thr His Gln Gln Leu Leu Ala Gln Lys Gly Ile Tyr
    1250                1255                1260

Phe Ser Met Val Ser Val Gln Ala Gly Ala Lys Arg Ser
    1265                1270                1275

<210> SEQ ID NO 9
<211> LENGTH: 2719
<212> TYPE: DNA
<213> ORGANISM: Homo sapiens

<400> SEQUENCE: 9
tttaggaacg caccgtgcac atgcttggtg gtcttgttaa gtggaaactg ctgctttaga    60
```

-continued

```
gtttgtttgg aaggtccggg tgactcatcc caacatttac atccttaatt gttaaagcgc    120
tgcctccgag cgcacgcatc ctgagatcct gagcctttgg ttaagaccga gctctattaa    180
gctgaaaaga taaaaactct ccagatgtct tccagtaatg tcgaagtttt tatcccagtg    240
tcacaaggaa acaccaatgg cttccccgcg acagtttcca atgacctgaa ggcatttact    300
gaaggagctg tgttaagttt tcataacatc tgctatcgag taaaactgaa gagtggcttt    360
ctaccttgtc gaaaaccagt tgagaaagaa atattatcga atatcaatgg gatcatgaaa    420
cctggtctca acgccatcct gggacccaca ggtggaggca aatcttcgtt attagatgtc    480
ttagctgcaa ggaaagatcc aagtggatta tctggagatg ttctgataaa tggagcaccg    540
cgacctgcca atttcaaatg taattcaggt tacgtggtac aagatgatgt tgtgatgggc    600
actctgacgg tgagagaaaa cttacagttc tcagcagctc ttcggcttgc aacaactatg    660
acgaatcatg aaaaaaacga acggattaac agggtcattg aagagttagg tctggataaa    720
gtggcagact ccaaggttgg aactcagttt atccgtggtg tgtctggagg agaaagaaaa    780
aggactagta taggaatgga gcttatcact gatccttcca tcttgtcctt ggatgagcct    840
acaactggct tagactcaag cacagcaaat gctgtccttt tgctcctgaa aaggatgtct    900
aagcagggac gaacaatcat cttctccatt catcagcctc gatattccat cttcaagttg    960
tttgatagcc tcaccttatt ggcctcagga agacttatgt tccacgggcc tgctcaggag    1020
gccttgggat actttgaatc agctggttat cactgtgagg cctataataa ccctgcagac    1080
ttcttcttgg acatcattaa tggagattcc actgctgtgg cattaaacag agaagaagac    1140
tttaaagcca cagagatcat agagccttcc aagcaggata agccactcat agaaaaatta    1200
gcggagattt atgtcaactc ctccttctac aaagagacaa aagctgaatt acatcaactt    1260
tccgggggtg agaagaagaa gaagatcaca gtcttcaagg agatcagcta caccacctcc    1320
ttctgtcatc aactcagatg ggtttccaag cgttcattca aaaacttgct gggtaatccc    1380
caggcctcta tagctcagat cattgtcaca gtcgtactgg gactggttat aggtgccatt    1440
tactttgggc taaaaaatga ttctactgga atccagaaca gagctggggt tctcttcttc    1500
ctgacgacca accagtgttt cagcagtgtt tcagccgtgg aactctttgt ggtagagaag    1560
aagctcttca tacatgaata catcagcgga tactacagag tgtcatctta tttccttgga    1620
aaactgttat ctgatttatt acccatgagg atgttaccaa gtattatatt tacctgtata    1680
gtgtacttca tgttaggatt gaagccaaag gcagatgcct tcttcgttat gatgtttacc    1740
cttatgatgg tggcttattc agccagttcc atggcactgg ccatagcagc aggtcagagt    1800
gtggtttctg tagcaacact tctcatgacc atctgttttg tgtttatgat gatttttttca    1860 ggtctgttgg tcaatctcac aaccattgca tcttggctgt catggcttca gtacttcagc    1920
attccacgat atggatttac ggctttgcag cataatgaat ttttgggaca aaacttctgc    1980
ccaggactca atgcaacagg aaacaatcct tgtaactatg caacatgtac tggcgaagaa    2040
tatttggtaa agcagggcat cgatctctca ccctggggct tgtggaagaa tcacgtggcc    2100
ttggcttgta tgattgttat tttcctcaca attgcctacc tgaaattgtt atttcttaaa    2160
aaatattctt aaatttcccc ttaattcagt atgatttatc ctcacataaa aagaagcac    2220 tttgattgaa gtattcaatc aagttttttt gttgttttct gttcccttgc catcacactg    2280
ttgcacagca gcaattgttt taaagagata cattttttaga aatcacaaca aactgaatta    2340
aacatgaaag aacccaagac atcatgtatc gcatatagt taatctcctc agacagtaac    2400
catggggaag aaatctggtc taatttatta atctaaaaaa ggagaattga attctggaaa    2460
```

-continued

```
ctcctgacaa gttattactg tctctggcat ttgtttcctc atctttaaaa tgaataggta   2520
ggttagtagc ccttcagtct taatacttta tgatgctatg gtttgccatt atttaatata   2580
tgacaaatgt attaatgcta tactggaaat gtaaaattga aaatatgttg gaaaaaagat   2640
tctgtcttat agggtaaaaa aagccaccgg tgatagaaaa aaaatctttt tgataagcac   2700
attaaagtta atagaactt                                                2719
```

<210> SEQ ID NO 10
<211> LENGTH: 655
<212> TYPE: PRT
<213> ORGANISM: Homo sapien

<400> SEQUENCE: 10

```
Met Ser Ser Ser Asn Val Glu Val Phe Ile Pro Val Ser Gln Gly Asn
1               5                   10                  15

Thr Asn Gly Phe Pro Ala Thr Val Ser Asn Asp Leu Lys Ala Phe Thr
            20                  25                  30

Glu Gly Ala Val Leu Ser Phe His Asn Ile Cys Tyr Arg Val Lys Leu
        35                  40                  45

Lys Ser Gly Phe Leu Pro Cys Arg Lys Pro Val Glu Lys Glu Ile Leu
    50                  55                  60

Ser Asn Ile Asn Gly Ile Met Lys Pro Gly Leu Asn Ala Ile Leu Gly
65                  70                  75                  80

Pro Thr Gly Gly Gly Lys Ser Ser Leu Leu Asp Val Leu Ala Ala Arg
                85                  90                  95

Lys Asp Pro Ser Gly Leu Ser Gly Asp Val Leu Ile Asn Gly Ala Pro
            100                 105                 110

Arg Pro Ala Asn Phe Lys Cys Asn Ser Gly Tyr Val Val Gln Asp Asp
        115                 120                 125

Val Val Met Gly Thr Leu Thr Val Arg Glu Asn Leu Gln Phe Ser Ala
    130                 135                 140

Ala Leu Arg Leu Ala Thr Thr Met Thr Asn His Glu Lys Asn Glu Arg
145                 150                 155                 160

Ile Asn Arg Val Ile Glu Glu Leu Gly Leu Asp Lys Val Ala Asp Ser
                165                 170                 175

Lys Val Gly Thr Gln Phe Ile Arg Gly Val Ser Gly Gly Glu Arg Lys
            180                 185                 190

Arg Thr Ser Ile Gly Met Glu Leu Ile Thr Asp Pro Ser Ile Leu Ser
        195                 200                 205

Leu Asp Glu Pro Thr Thr Gly Leu Asp Ser Ser Thr Ala Asn Ala Val
    210                 215                 220

Leu Leu Leu Leu Lys Arg Met Ser Lys Gln Gly Arg Thr Ile Ile Phe
225                 230                 235                 240

Ser Ile His Gln Pro Arg Tyr Ser Ile Phe Lys Leu Phe Asp Ser Leu
                245                 250                 255

Thr Leu Leu Ala Ser Gly Arg Leu Met Phe His Gly Pro Ala Gln Glu
            260                 265                 270

Ala Leu Gly Tyr Phe Glu Ser Ala Gly Tyr His Cys Glu Ala Tyr Asn
        275                 280                 285

Asn Pro Ala Asp Phe Phe Leu Asp Ile Ile Asn Gly Asp Ser Thr Ala
    290                 295                 300

Val Ala Leu Asn Arg Glu Glu Asp Phe Lys Ala Thr Glu Ile Ile Glu
305                 310                 315                 320
```

```
Pro Ser Lys Gln Asp Lys Pro Leu Ile Glu Lys Leu Ala Glu Ile Tyr
            325                 330                 335
Val Asn Ser Ser Phe Tyr Lys Glu Thr Lys Ala Glu Leu His Gln Leu
            340                 345                 350
Ser Gly Gly Glu Lys Lys Lys Ile Thr Val Phe Lys Glu Ile Ser
            355                 360                 365
Tyr Thr Thr Ser Phe Cys His Gln Leu Arg Trp Val Ser Lys Arg Ser
    370                 375                 380
Phe Lys Asn Leu Leu Gly Asn Pro Gln Ala Ser Ile Ala Gln Ile Ile
385                 390                 395                 400
Val Thr Val Val Leu Gly Leu Val Ile Gly Ala Ile Tyr Phe Gly Leu
            405                 410                 415
Lys Asn Asp Ser Thr Gly Ile Gln Asn Arg Ala Gly Val Leu Phe Phe
            420                 425                 430
Leu Thr Thr Asn Gln Cys Phe Ser Ser Val Ser Ala Val Glu Leu Phe
            435                 440                 445
Val Val Glu Lys Lys Leu Phe Ile His Glu Tyr Ile Ser Gly Tyr Tyr
    450                 455                 460
Arg Val Ser Ser Tyr Phe Leu Gly Lys Leu Leu Ser Asp Leu Leu Pro
465                 470                 475                 480
Met Arg Met Leu Pro Ser Ile Ile Phe Thr Cys Ile Val Tyr Phe Met
            485                 490                 495
Leu Gly Leu Lys Pro Lys Ala Asp Ala Phe Phe Val Met Met Phe Thr
            500                 505                 510
Leu Met Met Val Ala Tyr Ser Ala Ser Ser Met Ala Leu Ala Ile Ala
            515                 520                 525
Ala Gly Gln Ser Val Val Ser Val Ala Thr Leu Leu Met Thr Ile Cys
    530                 535                 540
Phe Val Phe Met Met Ile Phe Ser Gly Leu Leu Val Asn Leu Thr Thr
545                 550                 555                 560
Ile Ala Ser Trp Leu Ser Trp Leu Gln Tyr Phe Ser Ile Pro Arg Tyr
            565                 570                 575
Gly Phe Thr Ala Leu Gln His Asn Glu Phe Leu Gly Gln Asn Phe Cys
            580                 585                 590
Pro Gly Leu Asn Ala Thr Gly Asn Asn Pro Cys Asn Tyr Ala Thr Cys
            595                 600                 605
Thr Gly Glu Glu Tyr Leu Val Lys Gln Gly Ile Asp Leu Ser Pro Trp
    610                 615                 620
Gly Leu Trp Lys Asn His Val Ala Leu Ala Cys Met Ile Val Ile Phe
625                 630                 635                 640
Leu Thr Ile Ala Tyr Leu Lys Leu Leu Phe Leu Lys Lys Tyr Ser
            645                 650                 655

<210> SEQ ID NO 11
<211> LENGTH: 502
<212> TYPE: DNA
<213> ORGANISM: Mus musculus

<400> SEQUENCE: 11
ttcggcctag gggccgaggc ttatacggcc agttccatgg cactggccat agccacaggc      60
caaagtgtgg tgtctgtagc aacactactc atgacaatcg cttttgtatt tatgatgctc     120
ttttctggcc tcttggtgaa tctcagaacc attgggcctt ggctgtcctg gcttcagtac     180
tttagcattc ctcgatatgg cttcacagct ttgcagtata atgaattctt gggacaagag     240
```

```
ttttgtccag gattcaatgt aacggacaac agcacttgtg ttaacagcta tgcaatatgt      300
actggtaacg agtacttgat aaatcagggc atcgaactgt caccttgggg actgtggaag      360
aatcatgtgg ccctggcttg tatgattatt atcttcctca caattgccta cctgaaattg      420
ttgtttctta aaaagtattc ttaatttccc ctttaacgga ctattaattg tactccaatt      480
aaatatgggc actttgatta cc                                              502
```

```
<210> SEQ ID NO 12
<211> LENGTH: 147
<212> TYPE: PRT
<213> ORGANISM: Mus musculus

<400> SEQUENCE: 12

Phe Gly Leu Gly Ala Glu Ala Tyr Thr Ala Ser Ser Met Ala Leu Ala
1               5                   10                  15

Ile Ala Thr Gly Gln Ser Val Val Ser Val Ala Thr Leu Leu Met Thr
            20                  25                  30

Ile Ala Phe Val Phe Met Met Leu Phe Ser Gly Leu Leu Val Asn Leu
        35                  40                  45

Arg Thr Ile Gly Pro Trp Leu Ser Trp Leu Gln Tyr Phe Ser Ile Pro
    50                  55                  60

Arg Tyr Gly Phe Thr Ala Leu Gln Tyr Asn Glu Phe Leu Gly Gln Glu
65                  70                  75                  80

Phe Cys Pro Gly Phe Asn Val Thr Asp Asn Ser Thr Cys Val Asn Ser
                85                  90                  95

Tyr Ala Ile Cys Thr Gly Asn Glu Tyr Leu Ile Asn Gln Gly Ile Glu
            100                 105                 110

Leu Ser Pro Trp Gly Leu Trp Lys Asn His Val Ala Leu Ala Cys Met
        115                 120                 125

Ile Ile Ile Phe Leu Thr Ile Ala Tyr Leu Lys Leu Leu Phe Leu Lys
    130                 135                 140

Lys Tyr Ser
145
```

```
<210> SEQ ID NO 13
<211> LENGTH: 2025
<212> TYPE: DNA
<213> ORGANISM: Mus musculus

<400> SEQUENCE: 13
aaaggcataa atcctaaaga tgtcttccag taatgaccac gtgttagtac caatgtcgca       60
gagaaacaac aacggccttc ctaggatgaa ctccagagcc gttaggacgc tcgcagaagg      120
agatgtgttg agttttcatc acatcaccta tcgagtgaaa gtaaagagtg ggtttctagt      180
ccggaaaaca gttgagaaag aaatactatc agatatcaat gggatcatga acctggcct       240 taatgctatt ctgggaccca caggcggagg caagtcttcg ttgctagatg tcttagcagc      300
aaggaaagat ccaaagggat tatctggaga tgtttgata aatggagcac tcaacctgc        360 ccatttcaaa tgctgttcag gttatgtggt tcaagatgac gttgtgatgg caccctgac        420 agtgagagaa aacttacagt tctcagcagc tcttcgactt ccaacaacta tgaagaatca      480
tgaaaaaaat gaacggatta acacaatcat taaagagtta ggtctggaaa agtagcaga      540 ttctaaggtc ggaactcagt ttatccgtgg catctctgga ggagaaagaa aaggacaag       600 cataggatg gagctgatca ctgacccttc catcctcttc ctggatgagc ccacgactgg       660
tttggactca agcacagcga atgctgtcct tttgctcctg aaaaggatgt ctaaacaggg      720
```

-continued

```
tcgaacaatc atcttctcca ttcatcagcc tcggtattcc atctttaagt tgtttgacag      780 cctcaccttga ctggcttccg ggaaactcgt gttccatggg ccagcacaga aggccttgga     840
gtactttgca tcagcaggtt accactgtga gccctacaac aaccctgcgg attttttcct     900
tgatgtcatc aatggagatt cttctgctgt gatgttaaat agagaggaac aagacaatga     960
agcaaacaag actgaagagc cttccaaggg agagaagcca gtaatagaaa atttatctga    1020
gttttatatc aactctgcca tctatggaga aacaaaagct gaattagatc aacttccagg    1080
agctcaggaa aagaaaggaa catcggcctt caaagagcca gtctatgtta cctctttctg    1140
tcaccagctc cgatggattg ccaggcgctc atttaaaaac ttgctcggga accctcaagc    1200
ttctgttgct cagttaattg ttacagtcat actggggctt attattggtg ccatttactt    1260
tgatctgaaa tatgatgccg ctggaatgca aaatagagct ggagttttgt ttttcctgac    1320
taccaaccag tgttttttcca gtgtgtcagc tgtggagctg ttcgtagtgg agaagaaact    1380
cttcatacat gagtacatca gtggatatta cagagtgtct tcttacttct ttggaaaggt    1440
gatgtctgat ttactcccca tgaggttctt gccaagtgtt atattcactt gtatattata    1500
cttcatgtta ggactgaaga agacggtgga tgcttttttc atcatgatgt ttacccttat    1560
aatggtggct tatacggcca gttccatggc actggccata gccacaggcc aaagtgtggt    1620
gtctgtagca acacttctca tgacaatcgc ttttgtattt atgatgctct tttctggcct    1680
cttggtgaat ctcagaacca ttgggccttg gctgtcctgg cttcagtact ttagcattcc    1740
tcgatatggc ttcacagctt tgcagtataa tgaattcttg gacaagagt tttgtccagg    1800 attcaatgta acggacaaca gcacttgtgt taacagctat gcaatatgta ctggtaacga    1860
gtacttgata aatcagggca tcgaactgtc accttgggga ctgtggaaga tcatgtggc    1920 cctggcttgt atgattatta tcttcctcac aattgcctac ctgaaattgt gtttcttaa    1980 aaagtattct taatttcccc tttaacggac tattaattgt actcc                    2025
```

<210> SEQ ID NO 14
<211> LENGTH: 657
<212> TYPE: PRT
<213> ORGANISM: Mus musculus

<400> SEQUENCE: 14

```
Met Ser Ser Ser Asn Asp His Val Leu Val Pro Met Ser Gln Arg Asn
1               5                   10                  15

Asn Asn Gly Leu Pro Arg Met Asn Ser Arg Ala Val Arg Thr Leu Ala
            20                  25                  30

Glu Gly Asp Val Leu Ser Phe His His Ile Thr Tyr Arg Val Lys Val
        35                  40                  45

Lys Ser Gly Phe Leu Val Arg Lys Thr Val Glu Lys Glu Ile Leu Ser
    50                  55                  60

Asp Ile Asn Gly Ile Met Lys Pro Gly Leu Asn Ala Ile Leu Gly Pro
65                  70                  75                  80

Thr Gly Gly Gly Lys Ser Ser Leu Leu Asp Val Leu Ala Ala Arg Lys
                85                  90                  95

Asp Pro Lys Gly Leu Ser Gly Asp Val Leu Ile Asn Gly Ala Pro Gln
            100                 105                 110

Pro Ala His Phe Lys Cys Cys Ser Gly Tyr Val Val Gln Asp Asp Val
        115                 120                 125

Val Met Gly Thr Leu Thr Val Arg Glu Asn Leu Gln Phe Ser Ala Ala
    130                 135                 140
```

```
Leu Arg Leu Pro Thr Thr Met Lys Asn His Glu Lys Asn Glu Arg Ile
145                 150                 155                 160

Asn Thr Ile Ile Lys Glu Leu Gly Leu Glu Lys Val Ala Asp Ser Lys
            165                 170                 175

Val Gly Thr Gln Phe Ile Arg Gly Ile Ser Gly Glu Arg Lys Arg
        180                 185                 190

Thr Ser Ile Gly Met Glu Leu Ile Thr Asp Pro Ser Ile Leu Phe Leu
    195                 200                 205

Asp Glu Pro Thr Thr Gly Leu Asp Ser Ser Thr Ala Asn Ala Val Leu
210                 215                 220

Leu Leu Leu Lys Arg Met Ser Lys Gln Gly Arg Thr Ile Ile Phe Ser
225                 230                 235                 240

Ile His Gln Pro Arg Tyr Ser Ile Phe Lys Leu Phe Asp Ser Leu Thr
            245                 250                 255

Leu Leu Ala Ser Gly Lys Leu Val Phe His Gly Pro Ala Gln Lys Ala
        260                 265                 270

Leu Glu Tyr Phe Ala Ser Ala Gly Tyr His Cys Glu Pro Tyr Asn Asn
    275                 280                 285

Pro Ala Asp Phe Phe Leu Asp Val Ile Asn Gly Asp Ser Ser Ala Val
290                 295                 300

Met Leu Asn Arg Glu Glu Gln Asp Asn Glu Ala Asn Lys Thr Glu Glu
305                 310                 315                 320

Pro Ser Lys Gly Glu Lys Pro Val Ile Glu Asn Leu Ser Glu Phe Tyr
            325                 330                 335

Ile Asn Ser Ala Ile Tyr Gly Glu Thr Lys Ala Glu Leu Asp Gln Leu
        340                 345                 350

Pro Gly Ala Gln Glu Lys Lys Gly Thr Ser Ala Phe Lys Glu Pro Val
    355                 360                 365

Tyr Val Thr Ser Phe Cys His Gln Leu Arg Trp Ile Ala Arg Arg Ser
370                 375                 380

Phe Lys Asn Leu Leu Gly Asn Pro Gln Ala Ser Val Ala Gln Leu Ile
385                 390                 395                 400

Val Thr Val Ile Leu Gly Leu Ile Ile Gly Ala Ile Tyr Phe Asp Leu
            405                 410                 415

Lys Tyr Asp Ala Ala Gly Met Gln Asn Arg Ala Gly Val Leu Phe Phe
        420                 425                 430

Leu Thr Thr Asn Gln Cys Phe Ser Ser Val Ser Ala Val Glu Leu Phe
    435                 440                 445

Val Val Glu Lys Lys Leu Phe Ile His Glu Tyr Ile Ser Gly Tyr Tyr
450                 455                 460

Arg Val Ser Ser Tyr Phe Gly Lys Val Met Ser Asp Leu Leu Pro
465                 470                 475                 480

Met Arg Phe Leu Pro Ser Val Ile Phe Thr Cys Ile Leu Tyr Phe Met
            485                 490                 495

Leu Gly Leu Lys Lys Thr Val Asp Ala Phe Phe Ile Met Met Phe Thr
        500                 505                 510

Leu Ile Met Val Ala Tyr Thr Ala Ser Ser Met Ala Leu Ala Ile Ala
    515                 520                 525

Thr Gly Gln Ser Val Val Ser Val Ala Thr Leu Leu Met Thr Ile Ala
530                 535                 540

Phe Val Phe Met Met Leu Phe Ser Gly Leu Leu Val Asn Leu Arg Thr
545                 550                 555                 560
```

-continued

```
Ile Gly Pro Trp Leu Ser Trp Leu Gln Tyr Phe Ser Ile Pro Arg Tyr
            565                 570                 575

Gly Phe Thr Ala Leu Gln Tyr Asn Glu Phe Leu Gly Gln Glu Phe Cys
        580                 585                 590

Pro Gly Phe Asn Val Thr Asp Asn Ser Thr Cys Val Asn Ser Tyr Ala
    595                 600                 605

Ile Cys Thr Gly Asn Glu Tyr Leu Ile Asn Gln Gly Ile Glu Leu Ser
            610                 615                 620

Pro Trp Gly Leu Trp Lys Asn His Val Ala Leu Ala Cys Met Ile Ile
625                 630                 635                 640

Ile Phe Leu Thr Ile Ala Tyr Leu Lys Leu Leu Phe Leu Lys Lys Tyr
                645                 650                 655

Ser

<210> SEQ ID NO 15
<211> LENGTH: 20
<212> TYPE: DNA
<213> ORGANISM: Artificial Sequence
<220> FEATURE:
<223> OTHER INFORMATION: primer

<400> SEQUENCE: 15
ccacgtcagc cttggacaca                                              20

<210> SEQ ID NO 16
<211> LENGTH: 20
<212> TYPE: DNA
<213> ORGANISM: Artificial Sequence
<220> FEATURE:
<223> OTHER INFORMATION: primer

<400> SEQUENCE: 16
gccgcttggt gaggatctct                                              20

<210> SEQ ID NO 17
<211> LENGTH: 20
<212> TYPE: DNA
<213> ORGANISM: Artificial Sequence
<220> FEATURE:
<223> OTHER INFORMATION: primer

<400> SEQUENCE: 17
ccatagccac aggccaaagt                                              20

<210> SEQ ID NO 18
<211> LENGTH: 20
<212> TYPE: DNA
<213> ORGANISM: Artificial Sequence
<220> FEATURE:
<223> OTHER INFORMATION: primer

<400> SEQUENCE: 18
gggccacatg attcttccac                                              20

<210> SEQ ID NO 19
<211> LENGTH: 20
<212> TYPE: DNA
<213> ORGANISM: Artificial Sequence
<220> FEATURE:
<223> OTHER INFORMATION: primer

<400> SEQUENCE: 19
ggcctcagga agacttatgt                                              20
```

<210> SEQ ID NO 20
<211> LENGTH: 20
<212> TYPE: DNA
<213> ORGANISM: Artificial Sequence
<220> FEATURE:
<223> OTHER INFORMATION: primer

<400> SEQUENCE: 20
aaggaggtgg tgtagctgat                                                 20

<210> SEQ ID NO 21
<211> LENGTH: 19
<212> TYPE: DNA
<213> ORGANISM: Artificial Sequence
<220> FEATURE:
<223> OTHER INFORMATION: primer

<400> SEQUENCE: 21
agctggagag atcctcacc                                                  19

<210> SEQ ID NO 22
<211> LENGTH: 19
<212> TYPE: DNA
<213> ORGANISM: Artificial Sequence
<220> FEATURE:
<223> OTHER INFORMATION: primer

<400> SEQUENCE: 22
agccggagag atcctcacc                                                  19

<210> SEQ ID NO 23
<211> LENGTH: 20
<212> TYPE: DNA
<213> ORGANISM: Artificial Sequence
<220> FEATURE:
<223> OTHER INFORMATION: primer

<400> SEQUENCE: 23
ctgtagctgt caatctcggg                                                 20

<210> SEQ ID NO 24
<211> LENGTH: 20
<212> TYPE: DNA
<213> ORGANISM: Artificial Sequence
<220> FEATURE:
<223> OTHER INFORMATION: primer

<400> SEQUENCE: 24
ctgtagctgt caatctcagg                                                 20

<210> SEQ ID NO 25
<211> LENGTH: 20
<212> TYPE: DNA
<213> ORGANISM: Artificial Sequence
<220> FEATURE:
<223> OTHER INFORMATION: primer

<400> SEQUENCE: 25
ctgtagctgt caatcagagg                                                 20

<210> SEQ ID NO 26
<211> LENGTH: 2247
<212> TYPE: DNA
<213> ORGANISM: Homo sapiens

<400> SEQUENCE: 26

```
accgtgcaca tgcttggtgg tcttgttaag tggaaactgc tgctttagag tttgtttgga      60
aggtccgggt gactcatccc aacatttaca tccttaattg ttaaagcgct gcctccgagc     120
gcacgcatcc tgagatcctg agcctttggt taagaccgag ctctattaag ctgaaaagat     180
aaaaactctc cagatgtctt ccagtaatgt cgaagttttt atcccagtgt cacaaggaaa     240
caccaatggc ttccccgcga cagcttccaa tgacctgaag cattactg aaggagctgt      300
gttaagtttt cataacatct gctatcgagt aaaactgaag agtggctttc taccttgtcg     360
aaaaccagtt gagaagaaa tattatcgaa tatcaatggg atcatgaaac ctggtctcaa      420
cgccatcctg ggacccacag gtggaggcaa atcttcgtta ttagatgtct tagctgcaag     480
gaaagatcca agtggattat ctggagatgt tctgataaat ggagcaccgc gacctgccaa     540
tttcaaatgt aattcaggtt acgtggtaca agatgatgtt gtgatgggca ctctgacggt     600
gagagaaaac ttacagttct cagcagctct tcggcttgca acaactatga cgaatcatga     660
aaaaaacgaa cggattaaca gggtcattca agagttaggt ctggataaag tggcagactc     720
caaggttgga actcagttta tccgtggtgt gtctggagga gaaagaaaaa ggactagtat     780
aggaatggag cttatcactg atccttccat cttgttcttg gatgagccta caactggctt     840
agactcaagc acagcaaatg ctgtcctttt gctcctgaaa aggatgtcta agcagggacg     900
aacaatcatc ttctccattc atcagcctcg atattccatc ttcaagttgt tgatagcct      960
caccttattg gcctcaggaa gacttatgtt ccacgggcct gctcaggagg ccttgggata    1020
ctttgaatca gctggttatc actgtgaggc ctataataac cctgcagact tcttcttgga    1080
catcattaat ggagattcca ctgctgtggc attaaacaga gaagaagact ttaaagccac    1140
agagatcata gagccttcca agcaggataa gccactcata gaaaaattag cggagattta    1200
tgtcaactcc tccttctaca aagagacaaa agctgaatta catcaacttt ccggggtga     1260
gaagaagaag aagatcacag tcttcaagga gatcagctac accacctcct tctgtcatca    1320
actcagatgg gtttccaagc gttcattcaa aaacttgctg ggtaatcccc aggcctctat    1380
agctcagatc attgtcacag tcgtactggg actggttata ggtgccattt actttgggct    1440
aaaaaatgat tctactggaa tccagaacag agctgggggtt ctcttcttcc tgacgaccaa    1500
ccagtgtttc agcagtgttt cagccgtgga actctttgtg gtagagaaga agctcttcat    1560
acatgaatac atcagcggat actacagagt gtcatcttat ttccttggaa aactgttatc    1620
tgatttatta cccatgagga tgttaccaag tattatattt acctgtatag tgtacttcat    1680
gttaggattg aaggcaaagg cagatgcctt cttcgttatg atgtttaccc ttatgatggt    1740
ggcttattca gccagttcca tggcactggc catagcagca ggtcagagtg tggtttctgt    1800
agcaacactt ctcatgacca tctgtttttgt gtttatgatg atttttttcag gtctgttggt    1860
caatctcaca accattgcat cttggctgtc atggcttcag tacttcagca ttccacgata    1920
tggatttacg gctttgcagc ataatgaatt tttgggacaa aacttctgcc caggactcaa    1980
tgcaacagga aacaatcctt gtaactatgc aacatgtact ggcgaagaat atttggtaaa    2040
gcagggcatc gatctctcac cctggggctt gtggaagaat cacgtggcct tggcttgtat    2100
gattgttatt ttcctcacaa ttgcctacct gaaattgtta tttcttaaaa atattcttaa    2160
aatttcccct taattcagta tgatttatcc tcacataaaa agaagcact ttgattgaag      2220
tattcaaaaa aaaaaaaaaa aaaaaaa                                          2247
```

<210> SEQ ID NO 27
<211> LENGTH: 655
<212> TYPE: PRT
<213> ORGANISM: Homo sapien

<400> SEQUENCE: 27

```
Met Ser Ser Asn Val Glu Val Phe Ile Pro Val Ser Gln Gly Asn
1               5                   10                  15

Thr Asn Gly Phe Pro Ala Thr Ala Ser Asn Asp Leu Lys Ala Phe Thr
            20                  25                  30

Glu Gly Ala Val Leu Ser Phe His Asn Ile Cys Tyr Arg Val Lys Leu
        35                  40                  45

Lys Ser Gly Phe Leu Pro Cys Arg Lys Pro Val Glu Lys Glu Ile Leu
    50                  55                  60

Ser Asn Ile Asn Gly Ile Met Lys Pro Gly Leu Asn Ala Ile Leu Gly
65                  70                  75                  80

Pro Thr Gly Gly Gly Lys Ser Ser Leu Leu Asp Val Leu Ala Ala Arg
                85                  90                  95

Lys Asp Pro Ser Gly Leu Ser Gly Asp Val Leu Ile Asn Gly Ala Pro
            100                 105                 110

Arg Pro Ala Asn Phe Lys Cys Asn Ser Gly Tyr Val Gln Asp Asp
        115                 120                 125

Val Val Met Gly Thr Leu Thr Val Arg Glu Asn Leu Gln Phe Ser Ala
    130                 135                 140

Ala Leu Arg Leu Ala Thr Thr Met Thr Asn His Glu Lys Asn Glu Arg
145                 150                 155                 160

Ile Asn Arg Val Ile Gln Glu Leu Gly Leu Asp Lys Val Ala Asp Ser
                165                 170                 175

Lys Val Gly Thr Gln Phe Ile Arg Gly Val Ser Gly Gly Glu Arg Lys
            180                 185                 190

Arg Thr Ser Ile Gly Met Glu Leu Ile Thr Asp Pro Ser Ile Leu Phe
        195                 200                 205

Leu Asp Glu Pro Thr Thr Gly Leu Asp Ser Ser Thr Ala Asn Ala Val
    210                 215                 220

Leu Leu Leu Leu Lys Arg Met Ser Lys Gln Gly Arg Thr Ile Ile Phe
225                 230                 235                 240

Ser Ile His Gln Pro Arg Tyr Ser Ile Phe Lys Leu Phe Asp Ser Leu
                245                 250                 255

Thr Leu Leu Ala Ser Gly Arg Leu Met Phe His Gly Pro Ala Gln Glu
            260                 265                 270

Ala Leu Gly Tyr Phe Glu Ser Ala Gly Tyr His Cys Glu Ala Tyr Asn
        275                 280                 285

Asn Pro Ala Asp Phe Phe Leu Asp Ile Ile Asn Gly Asp Ser Thr Ala
    290                 295                 300

Val Ala Leu Asn Arg Glu Glu Asp Phe Lys Ala Thr Glu Ile Ile Glu
305                 310                 315                 320

Pro Ser Lys Gln Asp Lys Pro Leu Ile Glu Lys Leu Ala Glu Ile Tyr
                325                 330                 335

Val Asn Ser Ser Phe Tyr Lys Glu Thr Lys Ala Glu Leu His Gln Leu
            340                 345                 350

Ser Gly Gly Glu Lys Lys Lys Ile Thr Val Phe Lys Glu Ile Ser
        355                 360                 365

Tyr Thr Thr Ser Phe Cys His Gln Leu Arg Trp Val Ser Lys Arg Ser
    370                 375                 380
```

-continued

```
Phe Lys Asn Leu Leu Gly Asn Pro Gln Ala Ser Ile Ala Gln Ile Ile
385                 390                 395                 400

Val Thr Val Val Leu Gly Leu Val Ile Gly Ala Ile Tyr Phe Gly Leu
                405                 410                 415

Lys Asn Asp Ser Thr Gly Ile Gln Asn Arg Ala Gly Val Leu Phe Phe
            420                 425                 430

Leu Thr Thr Asn Gln Cys Phe Ser Ser Val Ser Ala Val Glu Leu Phe
            435                 440                 445

Val Val Glu Lys Lys Leu Phe Ile His Glu Tyr Ile Ser Gly Tyr Tyr
        450                 455                 460

Arg Val Ser Ser Tyr Phe Leu Gly Lys Leu Leu Ser Asp Leu Leu Pro
465                 470                 475                 480

Met Arg Met Leu Pro Ser Ile Ile Phe Thr Cys Ile Val Tyr Phe Met
                485                 490                 495

Leu Gly Leu Lys Ala Lys Ala Asp Ala Phe Phe Val Met Met Phe Thr
                500                 505                 510

Leu Met Met Val Ala Tyr Ser Ala Ser Ser Met Ala Leu Ala Ile Ala
            515                 520                 525

Ala Gly Gln Ser Val Val Ser Val Ala Thr Leu Leu Met Thr Ile Cys
        530                 535                 540

Phe Val Phe Met Met Ile Phe Ser Gly Leu Leu Val Asn Leu Thr Thr
545                 550                 555                 560

Ile Ala Ser Trp Leu Ser Trp Leu Gln Tyr Phe Ser Ile Pro Arg Tyr
                565                 570                 575

Gly Phe Thr Ala Leu Gln His Asn Glu Phe Leu Gly Gln Asn Phe Cys
            580                 585                 590

Pro Gly Leu Asn Ala Thr Gly Asn Asn Pro Cys Asn Tyr Ala Thr Cys
            595                 600                 605

Thr Gly Glu Glu Tyr Leu Val Lys Gln Gly Ile Asp Leu Ser Pro Trp
    610                 615                 620

Gly Leu Trp Lys Asn His Val Ala Leu Ala Cys Met Ile Val Ile Phe
625                 630                 635                 640

Leu Thr Ile Ala Tyr Leu Lys Leu Leu Phe Leu Lys Lys Tyr Ser
                645                 650                 655
```

ANTIBODIES HAVING BINDING SPECIFICITY FOR THE EXTRACELLULAR DOMAIN OF A BREAST CANCER RESISTANCE PROTEIN (BCRP)

CROSS-REFERENCE TO RELATED APPLICATIONS

The present Application is a Continuation-In-Part of U.S. Ser. No. 09/584,586 filed May 31, 2000 now U.S. Pat. No. 6,933,150 which is a Continuation-In-Part of co-pending International Application PCT/US99/11825 filed May 27, 1999, which claims the priority of provisional U.S. Ser. No. 60/086,988 filed May 28, 1998, the disclosures of which are hereby incorporated by reference in their entireties. Applicants claim the benefits of these Applications under 35 U.S.C. § § 120 and 119(e).

RESEARCH SUPPORT

The research leading to the present invention was supported in part by the National Institutes of Health Grant No: PO HL 53749-04 and the Cancer Center Support Grant P30 CA21765. The government may have certain rights in the present invention. Support for this invention was also provided by the AMERICAN LEBANESE SYRIAN ASSOCIATED CHARITIES and the ASSISI FOUNDATION OF MEMPHIS INC.

FIELD OF THE INVENTION

The present invention provides a method of identifying and/or isolating stem cells. The present invention also provides methods of using cell populations enriched for stem cells. In addition, the present invention provides methods for diagnosing and/or prognosing human acute myelogenous leukemia (AML).

BACKGROUND OF THE INVENTION

All of the cells and cell types of an individual adult mammal are derived from a single cell, the zygote. However, as cells mature and differentiate they lose their ability to be converted into a different cell type. Thus, most adult cells are fully differentiated and normally cannot be converted into another cell type. One particular exception is the adult stem cell. Adult stem cells retain the ability to differentiate into other cell types, though this differentiation is generally limited to forming cells of a single tissue type. For example, hematopoietic stem cells (HSCs) are capable of differentiating into any cell type of the blood and immune system, whereas brain stem cells can differentiate into the different cell types of the brain. In recent years, therapies for treating degenerative diseases and/or cancer (such as leukemia) have been designed which employ stem cells. However, heretofore, isolating stem cells from the human donors has proved to be extremely difficult since stem cells are relatively rare.

Hematopoietic stem cells are functionally defined based on their capacity for self-renewal divisions, which leads to the continuous generation of new HSCs over the lifetime of an animal, and by their potential for pluripotent hematopoietic differentiation. There are three possible general outcomes for the resulting daughter cells when a hematopoietic stem cell divides: (i) differentiation, (ii) self-renewal, or (iii) apoptosis. Despite the extensive study of HSCs, due to its relevance to bone marrow transplantation, gene therapy, and basic hematopoiesis, the mechanisms controlling these three tightly regulated outcomes are poorly understood.

Purification strategies for HSCs have been developed for both mouse [Spangrude et al., Science 241:58-62 (1988): (published erratum appears in Science 244(4908):1030 (1989)); Uchida et al., J.Exp.Med. 175:175-184 (1992)] and humans HSCs [Zanjani et al., J. Clin.Invest. 93:1051-1055 (1994), see comments; Larochelle et al., Nat.Med. 2:1329-1337 (1996); Civin et al., Blood 88:4102-4109 (1996)]. Most of these strategies use antibodies directed against various cell surface antigens and multiparameter cell sorting to isolate phenotypically defined cell populations. This approach has allowed isolation of murine stem cell populations of sufficiently high purity to allow reconstitution of irradiated recipients with less than 10 cells [Morrison et al., Proc.Natl.Acad. .Sci. USA 92:10302-10306 (1995); Osawa et al., Science 273: 242-245 (1996)], while considerably greater numbers of sorted human cells have been required to reconstitute xenogeneic recipients [Larochelle et al., Nat.Med. 2:1329-1337 (1996); Zanjani et al., Exp.Hematol. 26:353-360 (1998), see comments.]

The human MDR1 gene and its murine homologs were originally identified based on the ability of their expressed products, collectively referred to as P-glycoproteins (P-gps), to extrude a wide variety of cytotoxic drugs from the cell interior [Gros et al., Cell, 47:371-380 (1986) and Chen et al., Cell, 47:381-389 (1986)]. It is now known that the MDR1 gene belongs to a superfamily of transport proteins that contain a conserved ATP-binding cassette (ABC) which is necessary for pump function [Allikmets et al., Hum. Mol. Genet. 5:1649-1655 (1996)]. Numerous studies have clearly shown that P-gp expression plays an important role in the resistance of human tumor cells to cancer chemotherapy [Pastan and Gottesman, Annu. Rev. Med., 42:277-286 (1991)]. Considering that P-gps are also expressed in a wide variety of normal tissues, more recent studies have examined the normal physiologic functions of MDR1-like genes. Murine gene disruption experiments have demonstrated that expression of various P-gps is necessary for biliary excretion [Smit et al., Cell, 75:451-462 (1993)], maintenance of the blood-brain barrier [Schinkel et al., Cell, 77:491-502 (1994)], and elimination of drugs [Schinkel et al., Proc.Natl.Acad.Sci. USA, 94:4028-4033 (1997)]. P-gps can also mediate more general cellular functions including the translocation of lipids across the cell membrane [van Helvoort et al., Cell, 87:507-517 (1996)] and modulation of specific apoptosis pathways [Johnstone et al., Blood, 93:1075-1085 (1999) and Smyth et al., Proc.Natl.Acad.Sci. USA, 95:7024-7029 (1998)].

P-gp is expressed in a variety of hematopoietic cell types [Drach et al., Blood, 80:2729-2734 (1992)], including human CD34+ stem cells [Chaudhary and Roninson, Cell, 66:85-94 (1991)] and murine c-kit+ stem cells [Sorrentino et al., Blood, 86:491-501 (1995)]. Several lines of evidence suggest that P-gp expression is functionally conserved in hematopoietic stem cells.

Another ATP transport protein that contains a conserved ATP-binding cassette is the gene product of the Bcrp1/Mxr/Abcp/ABCG2 gene (referred to herein as BCRP when obtained from any mammalian source, but as mBCRP and huBCRP when the specific mouse or human gene or gene product(s) are being particularly referenced). The huBCRP cDNA was originally cloned from several different human tumor cell lines that were resistant to multiple drugs including doxorubicin, topotecan, and mitoxantrone [Doyle et al., Proc. .Natl.Acad.Sci. USA 95:15665-15670 (1998):(published erratum appears in Proc Natl Acad Sci U S A; 96(5):2569 (1999)); Maliepaard et al., Cancer Res. 59:4559-4563

(1999); Miyake et al., *Cancer Res.* 59:8-13 (1999)]. A highly related mouse homologue (mBcrp1) was cloned from fibroblasts selected for multidrug resistance [Allen et al., *Cancer Res.* 59:4237-4241 (1999)]. In contrast to the structure of the MDR1 gene, which consists of two duplicated halves, the predicted structure of BCRP is that of a "half transporter", with a single ATP binding cassette and transmembrane region. The expression pattern of human BCRP (huBCRP) is highly restricted in normal human tissues, with the highest levels of mRNA detected in the placenta, and much lower levels detected in adult organs [Doyle et al., *Proc.Natl.Acad..Sci. USA* 95:15665-15670 (1998):(published erratum appears in *Proc.Natl.Acad.SciU S A.* 96(5):2569 (1999)); Allikmets et al., *CancerRes.* 58:5337-5339 (1998)].

Hematopoietic stem cells can be identified based on their ability to efflux fluorescent dyes that are substrates for P-gp, such as Rhodamine (Rho) 123 [Spangrude and Johnson, *Proc.Natl.Acad.Sci. SA,* 87:7433-7437 (1990); Fleming et al., *J. Cell Biol.,* 122:897-902 (1993); Orlic et al., *Blood,* 82:762-770 (1993); and Zijlmans et al., *Proc.Natl.Acad.Sci. USA,* 92:8901-8905 (1995)] and Hoechst 33342 [McAlister et al., *Blood,* 75:1240-1246 (1990); Wolf et al., *Exp. Hematol.,* 21:614-622 (1993); and Leemhuis et al., *Exp. Hematol.,* 24:1215-1224 (1996)]. One particular approach for purifying stem cells is based on Hoechst dye-staining of bone marrow cells to identify a minor fraction of side population (SP) cells that are highly enriched for repopulating activity [Goodell et al., *J. Exp. Med.,* 183:1797-1806 (1996)]. This SP phenotype identifies a primitive subset of stem cells present in multiple mammalian species [Goodell et al., *Nat. Med.,* 3:1337-1345 (1997)], and based on verapamil inhibition studies, may be due to expression of P-gp or another ABC transporter [Goodell et al., *J. Exp. Med.,* 183:1797-1806 (1996)].

Despite a recent report demonstrating that sorting for expression of the vascular endothelial growth factor receptor can enrich human stem cells to near purity [Ziegler et al., *Science* 285:1553-1558 (1999)], there still remains a general need for better and more specific markers of human HSCs. In addition, there is a great need for new methodologies of isolating stem cells.

The citation of any reference herein should not be deemed as an admission that such reference is available as prior art to the instant invention.

SUMMARY OF THE INVENTION

The present invention provides methods of identifying and/or purifying stem cells by detecting and/or selecting for cells that express a specific transmembrane efflux pump. More particularly the present invention discloses that BCRP expression is a more specific marker for stem cells than all currently available markers. Such stem cells include hematopoietic stem cells, and side population (SP) stem cells from other organs. The present invention therefore provides methods for isolating primitive stem cells based on the detection of BCRP expression, which as disclosed herein, is a functional determinant for stem cells from a variety of tissues.

The present invention further provides methods of identifying cells that express BCRP. One such embodiment comprises obtaining a cell sample which contains (or is suspected to contain) stem cells and detecting the expression of BCRP by a cell in the cell sample. A cell is identified as a stem cell if BCRP is expressed by the cell.

The detection of the expression of BCRP can be performed via its specific pumping activity, i.e., it can remove Hoechst 33342 dye but not Rhodamine 123 dye (see Example 1 below). Preferably detection of the expression of BCRP is performed with an anti-BCRP antibody which binds to BCRP (more preferably the extracellular portion of BCRP). Stem cells can then be identified due to their binding to the anti-BCRP antibody. In one such embodiment the antibody is a polyclonal antibody. In another embodiment the antibody is a monoclonal antibody. Alternatively, the detection of the expression of BCRP is performed via PCR employing a PCR probe derived for a nucleic acid sequence that expresses BCRP (see Example 1 below).

In an alternative embodiment, the present invention provides a method for identifying a stem cell that further comprises detecting the expression of one or more additional stem cell markers, i.e., a protein that is expressed by stem cells. A cell that expresses BCRP and expresses one or more of such stem cell markers is then confirmed as a stem cell. In one such embodiment the stem cell marker is EM10. In another embodiment the stem cell marker is CD34. In a preferred embodiment of this type the stem cell is also CD38⁻ (i.e., does not express CD38). In still another embodiment the stem cell marker is Thy-1. In yet another embodiment the stem cell marker is P-gp. In still another embodiment the stem cell marker is c-kit. In yet another embodiment the stem cell marker is Ac133.

The present invention also provides methods of further enriching the stem cell population in a mixture of cells that have previously been enriched by selecting for an alternative stem cell marker. In a particular embodiment of this type, the cells have been previously selected for the expression of the CD34 marker. Such an enriched stem cell population can then be further enriched by selecting for cells that also express BCRP. Any of the methods taught by the present invention for identifying/selecting cells that express BCRP can be used.

Alternatively, or in conjunction with detecting the expression of BCRP, the methods for identifying a stem cell of the present invention can further comprise detecting the expression of one or more lineage specific markers. A cell that expresses BCRP (and preferably one or more additional stem cell markers) but does not express the lineage specific marker(s) is then identified as a stem cell.

In a particular embodiment the stem cell is a hematopoietic stem cell. In one such embodiment the lineage specific marker whose absence is used to confirm stem cell identification is CD14. In another embodiment the lineage specific marker is CD15. In yet another embodiment the lineage specific marker is CD38. In still another embodiment the lineage specific marker is HLA-DR. In yet another embodiment the lineage specific marker is CD71. In still another embodiment the lineage specific marker is CD33. In yet another embodiment the lineage specific marker is CD2. In still another embodiment the lineage specific marker is CD16. In yet another embodiment the lineage specific marker is CD19. In still another embodiment the lineage specific marker is CD20. In yet another embodiment the lineage specific marker is glycophorin A. In still another embodiment the lineage specific marker is CD3. In yet another embodiment the lineage specific marker is CD4. In still another embodiment the lineage specific marker is CD8. In yet another embodiment the lineage specific marker is CD56.

The present invention therefore also provides methods of isolating stem cells. One such embodiment comprises a method of isolating a cell that expresses BCRP that comprises obtaining a cell sample which contains (or is suspected to contain) a cell that expresses BCRP and detecting the expression of BCRP by a cell in the cell sample. After being detected the cell that expresses BCRP is isolated. As indicated above, the absence and/or presence of lineage specific markers and stem cell markers respectively, can also be employed in the detection of the stem cells.

Cell samples can be obtained from any animal, but preferably a mammal and more preferably a human. Preferably, these samples already have a cell population that has been previously enriched in stem cells.

One particular embodiment comprises obtaining a cell sample which contains (or is suspected to contain) stem cells and contacting them with an antibody that binds to BCRP (preferably an extracellular portion BCRP). Cells that bind to the antibody are then isolated. These isolated cells are identified as isolated stem cells due to their binding to the anti-BCRP antibody. In a preferred embodiment of the present invention the isolation of the stem cells is performed by flow cytometry. In one particular embodiment, the antibody has a fluorescent label and the isolation of the stem cells is performed by fluorescent-activated cell sorting (FACS).

In another embodiment, the anti-BCRP antibody is placed on a solid support. The solid support can then be contacted/incubated with a sample of cells, such that the cells can associate with the solid support by binding to the anti-BCRP antibody. The solid support is then washed to remove cells that bind non-specifically. The remaining cells are eluted from the solid support (by an excess of free antibody, for example). Based on their ability to bind anti-BCRP antibody with specificity, the eluted cells are identified as isolated stem cells.

In a particular embodiment, the solid support is an immunomagnetic bead (e.g., MILTENYI MINIMACS™, DYNABEADS™). The anti-BCRP antibody is placed on the immunomagnetic beads which are then contacted/incubated with a sample of cells, as indicated above, such that the cells can associate with the beads by binding to the anti-BCRP antibody. Preferably after an appropriate incubation period, the immunomagnetic beads can then be separated from the sample of cells with a magnet. The immunomagnetic beads are then washed to remove cells that bind non-specifically. The remaining cells are eluted from the immunomagnetic beads as indicated above. Again, based on their ability to bind anti-BCRP antibody, the isolated cells are identified as stem cells.

In one embodiment the BCRP is a huBCRP gene product which is encoded by the nucleotide sequence of SEQ ID NO:9 and has the amino acid sequence of SEQ ID NO:10. In another embodiment the BCRP is a huBCRP gene product which is encoded by the nucleotide sequence of SEQ ID NO:26 and has the amino acid sequence of SEQ ID NO:27. In yet another embodiment the BCRP is a murine BCRP (mBCRP) which is encoded by the nucleotide sequence of SEQ ID NO:13 and has the amino acid sequence of SEQ ID NO:14. In still another embodiment the BCRP is a mBCRP which is encoded by a nucleotide sequence comprising SEQ ID NO:11 and has an amino acid sequence comprising SEQ ID NO:12.

Furthermore, any step in any method for isolating and/or identifying stem cells can be repeated to enhance the isolation/identification process. In addition, individual methods can also be combined in order to enhance the isolation/identification processes.

The purified/isolated stem cells obtained from the methodology of the present invention are also part of the present invention. In addition, cell populations enriched for stem cells obtained by a method of the present invention are also provided. One such enriched population is obtained from a mixed population of cells that comprises both stem cells and cells that are not stem cells. The cells of the mixed population of cells are then separated into two individual groups of cells based on whether or not they express BCRP. The group of cells selected for expressing BCRP are a cell population enriched for stem cells. As indicated above, the selection process can be repeated one or more times to further enrich the population of cells for stem cells.

The identification and isolation of stem cells via the methods of the present invention extend beyond hematopoietic stem cells and comprises all stem cells, including but not limited to muscle stem cells, liver stem cells, gastrointestinal stem cells, brain stem cells, and embryonic stem cells. The present invention also provides methods of using these isolated stem cells including the use of muscle stem cells in the treatment of diseases such as muscular dystrophy, degenerative liver disorder, myocardial infarction, Parkinson's disease, degenerative disorders of the brain, and for tissue regeneration/replacement. In addition, the hematopoietic stem cells can be used in bone marrow transplants (e.g., for treatment of leukemia) as well as for ex vivo gene therapy for treatment of blood diseases such as sickle cell anemia and thalassemia.

The present invention also provides the antibodies and portions thereof that recognize an extracellular portion of a BCRP in its natural conformation. In a preferred embodiment an antibody of the present invention recognizes BCRP on the surface of a viable stem cell. In a particular embodiment the antibody is a polyclonal antibody. In another embodiment the antibody is a monoclonal antibody. In another embodiment the antibody is a chimeric antibody. In a preferred embodiment of this type the chimeric antibody is a humanized antibody.

The present invention also provides a method of prognosing human leukemia, particularly acute myelogenous leukemia (AML), through determination of BCRP expression in leukemic cells, e.g., blast cells from individuals having or suspected of having AML. The effectiveness of chemotherapeutic agents which can be effluxed from the cell by BCRP is predictably decreased by the presence of BCRP on leukemic cells. Determination of the presence and level of BCRP expression in the leukemic cells of an individual can therefore help the medical practitioner develop a therapeutic regimen which takes into account the predicted efficacy of such agents and allows proper consideration of alternative therapies or agents which are not susceptible to the counter-effects of BCRP where BCRP expression is present.

Accordingly, it is a principal object of the present invention to provide a method of obtaining purified stem cells.

It is a further object of the present invention to provide the purified stem cells.

It is a further object of the present invention to provide methods of using the purified stem cells in the treatment of diseases in which one or more specific cell types are being adversely depleted and/or become dysfunctional.

It is a further object of the present invention to provide methods of using the purified stem cells for gene therapy.

It is a further object of the present invention to provide methods of identifying stem cells in vitro, in situ, and in vivo among mixed populations of cells and/or tissues.

It is a further object of the present invention to use BCRP as a marker for prognosing the progression of AML.

These and other aspects of the present invention will be better appreciated by reference to the following drawings and Detailed Description.

DETAILED DESCRIPTION OF THE INVENTION

Figure 1:
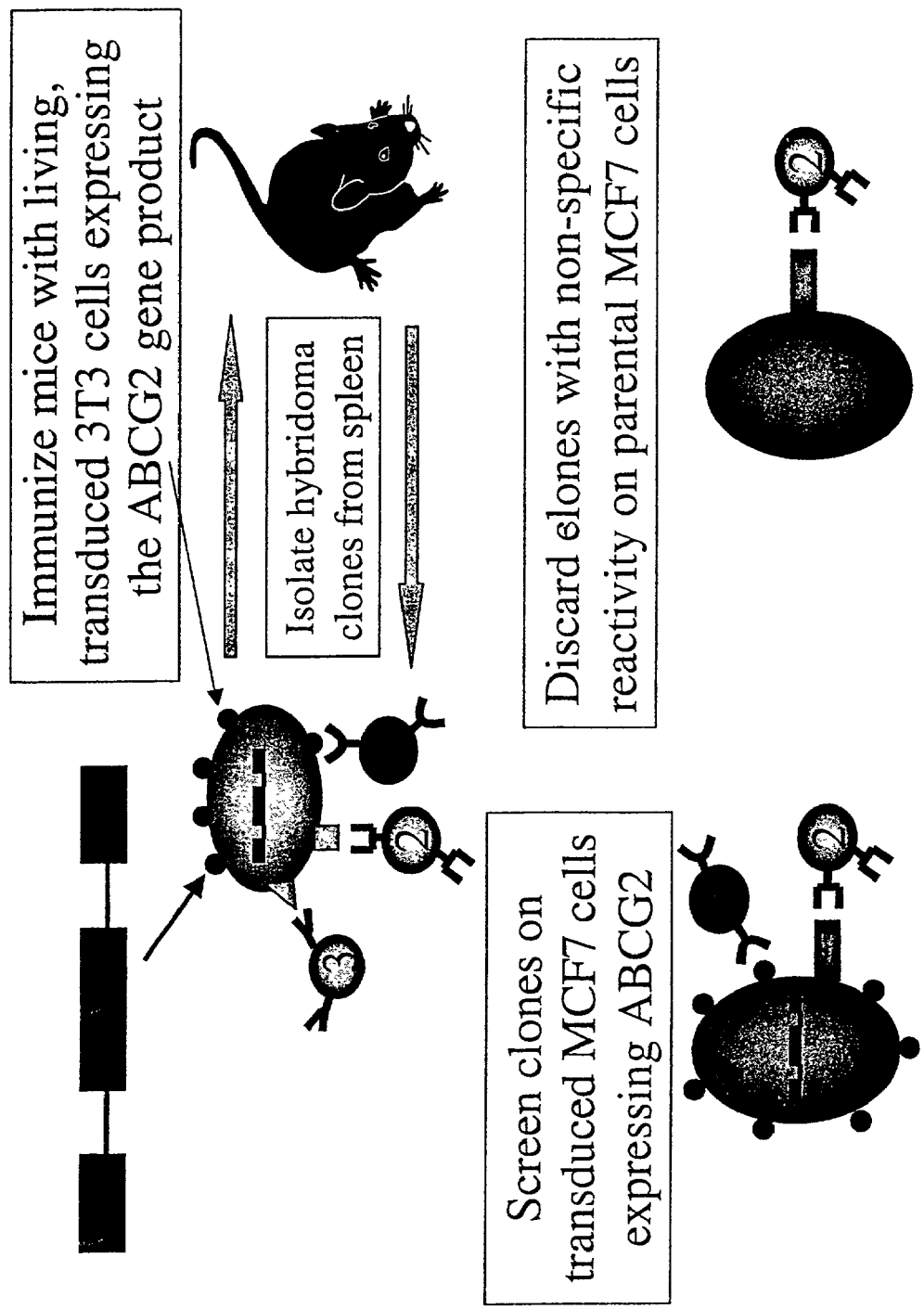
FIG. 1 is a schematic representation of a method of producing anti-BCRP monoclonal antibodies that can be used to isolate living stem cells by cell sorting.

The present invention provides the use of a specific ATP transporter, BCRP to identify and/or isolate a mammalian stem cell. Indeed, as shown herein, the BCRP gene is expressed at relatively high levels both in primitive CD34- murine HSCs and in SP cells from the bone marrow. In contrast, the expression of other known ABC transporters in the highly enriched CD34-stem cell population is low to absent. A retroviral vector expressing the huBCRP cDNA has been constructed as described below to study the functional properties of huBCRP. Fibroblasts expressing this vector gain the capacity to efflux Hoechst dye, a prerequisite property for establishment of the SP phenotype. Furthermore, when primary bone marrow cells are transduced with the BCRP vector, there is a large expansion of SP cells over time in culture. SP cells from the muscle also express BCRP at high levels. Indeed, BCRP mRNA expression is highly restricted in normal tissues. Furthermore, as disclosed herein, BCRP expression is relatively restricted to the hematopoietic stem cell compartment in mice. In accordance with these data BCRP expression is contemplated to be a universal marker for stem cells from various organs, and may well be the critical molecule for conferring the dye efflux phenotype to stem cells. Therefore, the present invention provides a method of identifying stem cells by their expression of BCRP. Such identification can then be used to isolate the stem cells.

Given the capacity of BCRP to confer resistance to anthracyline drugs [Miyake et al., Cancer Res. 59:8-13 (1999)], BCRP expression may directly confer resistance to AML induction chemotherapy. Indeed, BCRP expression in AML blasts appears to be associated with a drug resistant phenotype and thereby predict a poor prognosis. Therefore, the present invention also provides a method of prognosticating pediatric patients with AML, e.g., by examining/monitoring blast cells from such pediatric patients.

As demonstrated in the Examples below, stem cells from the bone marrow, skeletal muscle, and other tissues can be identified by the "side population" (SP) phenotype. While heretofore it had been assumed that the expression of ABC transporters is responsible for this phenotype, the specific molecules involved had not been defined. Herein, it is demonstrated that expression of the Bcrp1 (mBCRP)/ABCG2 (huBCRP) gene is a conserved feature of stem cells from diverse tissue sources. Indeed, mBCRP mRNA is expressed at high levels in primitive murine hematopoietic stem cells, and is sharply downregulated with stem cell differentiation. Enforced expression of the huBCRP cDNA directly conferred the SP phenotype to bone marrow cells, and causes a block in differentiation using both in vitro and transplantation-based assays. These results identify BCRP gene expression as a novel stem cell marker, and that its observed expression reflects a functional role in inhibiting stem cell differentiation. Therefore, the present invention provides methods of identifying stem cells through assays that can detect the expression of the BCRP.

Thus the studies disclosed herein demonstrate that expression of the BCRP transporter is highly conserved in primitive stem cells from a variety of sources. Expression was noted in SP cells from murine bone marrow, skeletal muscle, cultured ES cells, and in Rhesus monkey bone marrow. Within the lineage negative compartment of murine bone marrow cells, BCRP expression was relatively restricted to primitive CD34- stem cells, and expression was sharply downregulated with differentiation. The link between BCRP expression and SP cells was further strengthened by the observation that enforced expression in bone marrow cells caused a significant expansion of cells bearing the SP phenotype, both in vitro and in vivo. Altogether, these findings support the idea that BCRP expression is a widely conserved and specific marker for stem cells, and indicate that this transporter plays a role in stem cell function and/or maintenance of stem cell phenotype. Cell sorting for BCRP expression using appropriate antibodies provides a new strategy for stem cell purification applicable to cells from different organ sources. BCRP expression is further contemplated as a marker for the recently described trans-differentiating stem cells found in murine bone marrow [Lagasse, E. et al., Nat. Med. 6:1229-1234 (2000)] and skeletal muscle [Jackson, K. A et al., Proc. Natl. Acad. Sci. U.S.A 96:14482-14486 (1999); Gussoni, E. et al., Nature 401: 390-394 (1999)].

Therefore, if appearing herein, the following terms shall have the definitions set out below.

A "hematopoietic stem cell" is a pluripotent cell that is able to either replicate itself with self-renewal divisions or to differentiate along a number of pathways and thereby generate erythrocytes, granulocytes, monocytes, mast cells, lymphocytes, and megakaryocytes. These stem cells occur with a frequency of about 1 stem cell per 104 bone marrow cells.

A "heterologous gene" as used herein is a gene that is introduced into a stem cell (e.g., a hematopoietic stem cell) through a molecular biological manipulation. As defined herein, this molecular biological manipulation is made such that the heterologous gene is inserted into the stem cell. The heterologous gene need not be expressed in the stem cell as long as it is expressed in the progeny of the stem cell. The coding sequence of the heterologous gene is operatively linked to an expression control sequence. Generally a heterologous gene is first placed into a vector. The heterologous gene is not necessarily naturally contained by the vector, though a heterologous gene can encode a protein that is native to the stem cell. For example, the heterologous gene can encode a functional protein and be used in ex vivo gene therapy to replace the corresponding defective gene in a stem cell, e.g., an hematopoietic stem cell. The heterologous gene will usually be flanked by DNA that does not flank the genomic DNA in the genome of the source organism. Alternatively, the heterologous gene may not be naturally found in the stem cell, such as the gene for human MDR1 introduced into a murine hematopoietic stem cell.

A cell has been "transduced" by a heterologous gene such as the MDR1 gene (i.e., a nucleic acid encoding MDR1), when the gene has been introduced inside the cell and the coding sequence of the gene is operatively linked to an expression control sequence. The transducing gene is carried by a vector and the gene may or may not be integrated (covalently linked) into chromosomal DNA making up the genome of the cell. A stably transduced cell is one in which the transducing gene has become integrated into a chromosome so that it is inherited by daughter cells through chromosome replication. This stability is demonstrated by the ability of the cell to establish cell lines or clones comprised of a population of daughter cells containing the transducing gene.

A "clone" is a population of cells derived from a single cell or common ancestor by mitosis. A "cell line" is a clone of a primary cell that is capable of stable growth in vitro for many generations.

As used herein a "gene-modified hematopoietic stem cell" is a hematopoietic stem cell that has been transduced by a heterologous gene.

As used herein the "expansion" of an hematopoietic stem cell indicates that there is an increase in the absolute number of hematopoietic stem cells, i.e., during the culturing of the cells. Analogously, an hematopoietic cell that has undergone such expansion has been "expanded".

As used herein "engrafting" a stem cell, preferably an expanded hematopoietic stem cell, means placing the stem cell into an animal, e.g., by injection, wherein the stem cell persists in vivo. This can be readily measured by the ability of the hematopoietic stem cell, for example, to contribute to the ongoing blood formation.

As used herein an "ABC transporter" is used in the conventional sense and is used to describe a protein that is a transport ATPase. ABC transporters are members of a large family of transport proteins that are ATP-dependent. The name is derived from a highly conserved ATP-binding cassette contained by all of the members. [See, Alberts et al., *Molecular Biology of the Cell,* 3rd edition, Garland Publishing Inc. (New York) Pages 519-522 (1994)]. MDR1 and BCRP are two transmembrane efflux pumps that are part of the family of ABC transporters.

The Breast Cancer Resistance Protein is an ATP transporter protein that contains a conserved ATP-binding cassette which has been isolated from a number of different cell lines and mammalian tissues. Names in the literature of genes encoding this protein include Bcrp1, Mxr, Abcp and ABCG2 gene. Whereas, the murine gene is generally termed as the Bcrp1 gene and the corresponding human gene has been termed the ABCG2 gene, as used herein, "BCRP" is meant to include all of such ATP transport proteins obtained from any mammalian source. The murine protein is also referred to herein as mBCRP, whereas the human protein is termed herein, "huBCRP" when the specific mouse or human gene or gene product(s) are being particularly referenced. One huBCRP gene product which is encoded by the nucleotide sequence of SEQ ID NO:9 and has the amino acid sequence of SEQ ID NO:10, whereas another variant is encoded by the nucleotide sequence of SEQ ID NO:26 and has the amino acid sequence of SEQ ID NO:27. One mBCRP is encoded by the nucleotide sequence of SEQ ID NO:13 and has the amino acid sequence of SEQ ID NO:14 and another mBCRP is encoded by a nucleotide sequence comprising SEQ ID NO:11 and has an amino acid sequence comprising SEQ ID NO:12.

A "replicon" is any genetic element (e.g., plasmid, chromosome, virus) that functions as an autonomous unit of DNA replication in vivo; i.e., capable of replication under its own control.

A "vector" is a replicon, such as plasmid, phage or cosmid, to which another DNA segment may be attached so as to bring about the replication of the attached segment. The term "vector" can also refer to a recombinant virus or defective virus containing a replicon to which another DNA segment may be attached.

A "DNA molecule" refers to the polymeric form of deoxyribonucleotides (adenine, guanine, thymine, or cytosine) in its either single stranded form, or a double-stranded helix. This term refers only to the primary and secondary structure of the molecule, and does not limit it to any particular tertiary forms. Thus, this term includes double-stranded DNA found, inter alia, in linear DNA molecules (e.g., restriction fragments), viruses, plasmids, and chromosomes. In discussing the structure of particular double-stranded DNA molecules, sequences may be described herein according to the normal convention of giving only the sequence in the 5' to 3' direction along the nontranscribed strand of DNA (i.e., the strand having a sequence homologous to the mRNA).

A "coding sequence" is a nucleic acid sequence which can be reverse transcribed (i.e., when part of a retroviral vector) and/or transcribed and then translated into a polypeptide in vitro and/or in vivo when placed under the control of appropriate regulatory sequences. The boundaries of the coding sequence are determined by a start codon at the 5' (amino) terminus and a translation stop codon at the 3' (carboxyl) terminus. A coding sequence can include, but is not limited to, prokaryotic sequences, cDNA from eukaryotic mRNA, genomic DNA sequences from eukaryotic (e.g., mammalian) DNA, and even synthetic DNA sequences. A polyadenylation signal and transcription termination sequence will usually be located 3' to the coding sequence.

A nucleic acid sequence is "operatively linked" to an expression control sequence when the expression control sequence controls and regulates the transcription and/or translation of that nucleic acid sequence. The term "operatively linked" includes having an appropriate start signal (e.g., ATG) in front of the nucleic acid sequence to be expressed and maintaining the correct reading frame to permit expression of the nucleic acid sequence under the control of the expression control sequence and production of the desired product encoded by the nucleic acid sequence. If a gene that one desires to insert into a recombinant DNA molecule does not contain an appropriate start signal for example, such a start signal can be inserted in front of the gene.

Transcriptional and translational control sequences are DNA regulatory sequences, such as promoters, enhancers, polyadenylation signals, terminators, and the like, that provide for the expression of a coding sequence in a host cell.

A "promoter sequence" is a DNA regulatory region capable of binding RNA polymerase in a cell and initiating transcription of a downstream (3' direction) coding sequence. For purposes of defining the present invention, the promoter sequence is bounded at its 3' terminus by the transcription initiation site and extends upstream (5' direction) to include the minimum number of bases or elements necessary to initiate transcription at levels detectable above background. Within the promoter sequence will be found a transcription initiation site (conveniently defined for example, by mapping with nuclease S1), as well as protein binding domains (consensus sequences) responsible for the binding of RNA polymerase. Eukaryotic promoters will often, but not always, contain "TATA" boxes and "CAT" boxes.

A coding sequence is "under the control" of transcriptional and translational control sequences in a cell when RNA polymerase transcribes the coding sequence into mRNA, which is then translated into the protein encoded by the coding sequence.

Any of a wide variety of expression control sequences—sequences that control the expression of a DNA sequence operatively linked to it—may be used in these vectors to express the DNA sequences of this invention. Such useful expression control sequences include, for example, the early or late promoters of SV40, CMV, vaccinia, polyoma, adenovirus, herpes virus and other sequences known to control the expression of genes of mammalian cells, and various combinations thereof.

In selecting an expression control sequence, a variety of factors will normally be considered. These include, for example, the relative strength of the system, its controllability, and its compatibility with the particular DNA sequence or gene to be expressed, particularly as regards potential secondary structures. Considering these and other factors a person skilled in the art will be able to construct a variety of vector/expression control sequence combinations that will express the heterologous genes used in the present invention.

The phrase "pharmaceutically acceptable" refers to molecular entities and compositions that are physiologically tolerable and do not typically produce an allergic or similar untoward reaction, such as gastric upset, dizziness and the like, when administered to a human. Preferably, as used herein, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant, excipient, or vehicle with which the compound is administered. Such pharmaceutical carriers can be sterile liquids, such as water and oils, including those of petroleum, animal, vegetable or synthetic origin, such as peanut oil, soybean oil, mineral oil, sesame oil and the like. Water or aqueous solution saline solutions and aqueous dextrose and glycerol solutions are preferably employed as carriers, particularly for injectable solutions.

The phrase "therapeutically effective amount" is used herein to mean an amount sufficient to reduce by at least about 15 percent, preferably by at least 50 percent, more preferably by at least 90 percent, and most preferably prevent and/or treat, a clinically significant deficit in the activity, function and response of the host. Alternatively, a therapeutically effective amount is sufficient to cause an improvement in a clinically significant condition in the host.

Nucleic Acid Probes

A nucleic acid molecule is "hybridizable" to another nucleic acid molecule, such as a cDNA, genomic DNA, or RNA, when a single stranded form of the nucleic acid molecule can anneal to the other nucleic acid molecule under the appropriate conditions of temperature and solution ionic strength [see Sambrook, Fritsch & Maniatis, *Molecular Cloning: A Laboratory Manual*, Second Edition (1989) Cold Spring Harbor Laboratory Press, Cold Spring Harbor, N.Y. (herein "Sambrook et al., 1989" and Sambrook and Russell, *Molecular Cloning: A Laboratory Manual*, Third Edition (2001) Cold Spring Harbor Laboratory Press, Cold Spring Harbor, N.Y.]. The conditions of temperature and ionic strength determine the "stringency" of the hybridization. Specific hybridization conditions, corresponding to a $T_m$ of 55□, can be used, e.g., 5× SSC, 0.1% SDS, 0.25% milk, and no formamide; or 30% formamide, 5× SSC, 0.5% SDS. Moderate stringency hybridization conditions correspond to a higher $T_m$, e.g., 40% formamide, with 5× or 6× SSC. High stringency hybridization conditions correspond to the highest $T_m$, e.g., 50% formamide, 5× or 6× SSC. These conditions can be used for both annealing and wash steps. Hybridization requires that the two nucleic acids contain complementary sequences, although depending on the stringency of the hybridization, mismatches between bases are possible. The appropriate stringency for hybridizing nucleic acids depends on the length of the nucleic acids and the degree of complementation, variables well known in the art. The greater the degree of similarity or homology between two nucleotide sequences, the greater the value of $T_m$ for hybrids of nucleic acids having those sequences. The relative stability (corresponding to higher $T_m$) of nucleic acid hybridizations decreases in the following order: RNA:RNA, DNA:RNA, DNA:DNA. For hybrids of greater than 100 nucleotides in length, equations for calculating $T_m$ have been derived [see Sambrook et al., supra, 9.50-10.51]. For hybridization with shorter nucleic acids, i.e., oligonucleotides, the position of mismatches becomes more important, and the length of the oligonucleotide determines its specificity [see Sambrook et al., supra, 11.7-11.8]. Preferably a minimum length for a hybridizable nucleic acid (probe and/or primer) is at least about 12 nucleotides; preferably at least about 18 nucleotides; and more preferably the length is at least about 27 nucleotides; and most preferably at least about 36 nucleotides. Particular primers for BCRP, and mdr1a, mdr1b, and mdr2 are provided in Example 1 below.

Such nucleotide probes and primers can be labeled or used to label complementary DNA (where appropriate) by any number of ways well known in the art including using a radioactive label, such as $^3H$, $^{14}C$, $^{32}P$, or $^{35}S$, a fluorescent label, a boron label [U.S. Pat. No. 5,595,878, Issued Jan. 21, 1997 and U.S. Pat. No. 5,876,938, Issued Mar. 2, 1999 which are incorporated by reference in their entireties], and enzymatic tags such as urease, alkaline phosphatase or peroxidase. In the case of enzyme tags, calorimetric indicator substrates are known which can be employed to provide a means visible to the human eye or spectrophotometrically, to identify specific hybridization with complementary nucleic acid-containing samples.

Antibodies to the ABC Transporters of the Present Invention

According to the present invention, ABC transporters as produced by a recombinant source, or through chemical synthesis, or an ABC transporter isolated from a natural source; and derivatives or analogs thereof, including fusion proteins, may be used as an immunogen to generate antibodies that recognize an ABC transporter such as BCRP. Such antibodies include but are not limited to polyclonal, monoclonal, chimeric including humanized chimeric, single chain, Fab fragments, and a Fab expression library.

In a particular embodiment an antibody is raised to an external epitope of BCRP. In a particular embodiment the epitope is derived from the extracellular portion of BCRP. Such an antibody can be used to sort living cells on a flow cytometer. These antibodies can be used, for example, to sort hematopoietic cells based on BCRP (bcrp) expression. Such antibodies also may be used to detect BCRP as a marker for repopulating activity.

The anti-BCRP antibodies of the invention may be cross reactive, that is, they may recognize a BCRP derived from a different source, e.g., an anti-human BCRP antibody may recognize both human and mouse BCRP. Polyclonal antibodies have greater likelihood of cross reactivity. Alternatively, an antibody of the invention may be specific for a single form of a BCRP, such as the huBCRP having the amino acid sequence of SEQ ID NO:10.

Various procedures known in the art may be used for the production of polyclonal antibodies to BCRP, for example, or derivative or analog thereof. For the production of antibody, various host animals can be immunized by injection with the BCRP, or a derivative (e.g., or fusion protein) thereof, including but not limited to rabbits, mice, rats, sheep, goats, etc. In one embodiment, the BCRP can be conjugated to an immunogenic carrier, e.g., bovine serum albumin (BSA) or keyhole limpet hemocyanin (KLH). Various adjuvants may be used to increase the immunological response, depending on the host species, including but not limited to Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (bacille Calmette-Guerin) and Corynebacterium parvum.

For preparation of monoclonal antibodies directed toward the BCRP, or analog, or derivative thereof, any technique that provides for the production of antibody molecules by continuous cell lines in culture may be used. These include but are not limited to the hybridoma technique originally developed by Kohler and Milstein [Nature, 256:495-497 (1975)], as well as the trioma technique, the human B-cell hybridoma technique [Kozbor et al., Immunology Today, 4:72 (1983); Cote et al., Proc. Natl. Acad. Sci. USA, 80:2026-2030 (1983)], and the EBV-hybridoma technique to produce human monoclonal antibodies [Cole et al., in Monoclonal Antibodies and Cancer Therapy, Alan R. Liss, Inc., pp. 77-96 (1985)]. In an additional embodiment of the invention, monoclonal antibodies can be produced in germ-free animals utilizing recent technology [PCT/US90/02545]. In fact, according to the invention, techniques developed for the production of "chimeric antibodies" [Morrison et al., J. Bacteriol., 159: 870 (1984); Neuberger et al., Nature, 312:604-608 (1984); Takeda et al., Nature, 314:452-454 (1985)] by splicing the genes from a mouse antibody molecule specific for a BCRP together with genes from a human antibody molecule of appropriate biological activity can be used; such antibodies are within the scope of this invention. Such human or humanized chimeric antibodies are preferred for use in therapy of human diseases or disorders (described infra), since the human or humanized antibodies are much less likely than xenogeneic antibodies to induce an immune response, in particular an allergic response, themselves. In a particular embodiment, the BCRP-expressing cells of the present invention are used to raise monoclonal antibodies to external cell surface epitopes. Antibody producer clones can be screened for differential staining of producer cells versus their parental packaging cells (see FIG. 1).

According to the invention, techniques described for the production of single chain antibodies [U.S. Pat. Nos. 5,476, 786 and 5,132,405 to Huston; U.S. Pat. No. 4,946,778] can be adapted to produce for example, BCRP-specific single chain antibodies. An additional embodiment of the invention utilizes the techniques described for the construction of Fab expression libraries [Huse et al., Science, 246:1275-1281 (1989)] to allow rapid and easy identification of monoclonal Fab fragments with the desired specificity for a BCRP, or its derivatives, or analogs.

Antibody fragments which contain the idiotype of the antibody molecule can be generated by known techniques. For example, such fragments include but are not limited to: the F(ab')$_2$ fragment which can be produced by pepsin digestion of the antibody molecule; the Fab' fragments which can be generated by reducing the disulfide bridges of the F(ab')$_2$ fragment, and the Fab fragments which can be generated by treating the antibody molecule with papain and a reducing agent.

In the production of antibodies, screening for the desired antibody can be accomplished by techniques known in the art, e.g., radioimmunoassay, ELISA (enzyme-linked immunosorbant assay), "sandwich" immunoassays, immunoradiometric assays, gel diffusion precipitin reactions, immunodiffusion assays, in situ immunoassays (using colloidal gold, enzyme or radioisotope labels, for example), Western blots, precipitation reactions, agglutination assays (e.g., gel agglutination assays, hemagglutination assays), complement fixation assays, immunofluorescence assays, protein A assays, flow cytometry, and immunoelectrophoresis assays, etc. In one embodiment, antibody binding is detected by detecting a label on the primary antibody. In another embodiment, the primary antibody is detected by detecting binding of a secondary antibody or reagent to the primary antibody. In a further embodiment, the secondary antibody is labeled. Many means are known in the art for detecting binding in an immunoassay and are within the scope of the present invention. For example, to select antibodies which recognize a specific epitope of BCRP, one may assay generated hybridomas for a product which binds to the BCRP fragment containing such epitope and choose those which do not cross-react with BCRP. For selection of an antibody specific to a BCRP from a particular source, one can select on the basis of positive binding with BCRP expressed by or isolated from that specific source.

The present invention also provides methods for producing BCRP monoclonal antibodies that can be used to isolate living stem cells (see FIG. 1). In a preferred embodiment of this type the living stem cells are isolated by a cell sorting technique. One initial step can be to obtain a cDNA sequence encoding a BCRP and then inserting it into a vector construct (preferably a retroviral vector). This construct can then be introduced into packaging cells (e.g., retroviral packaging cells) to produce transducing vector particles. When GPE86 packaging cells are used, ecotropic ABCG2 (i.e., huBCRP) vector is produced in the supernatant, and can be used to transduce murine 3T3 cells. After applying the supernatant to logarithmically growing cells, transduced 3T3 cells that express the huBCRP can be isolated by flow cytometry based on their capacity to efflux the fluorescent dye Hoechst 33342. The 3T3 cells which express huBCRP (oval cell, see FIG. 1), can then be injected into the intraperitoneal space in mice. The strategy of using living cells transduced with the vector increases the probability that the immune system will detect external huBCRP epitopes in their native configuration, rather than epitopes that are internally located in the cells, or epitopes only present in denatured protein.

After several rounds of immunization, mice that show anti-huBCRP activity in the peripheral serum can be killed. Their spleens are then isolated and about 500 hybridoma clones are obtained by fusion with myeloma cells using standard techniques. Supernatants from these growing fusion clones are then screened for the presence of anti-huBCRP antibodies. This screening process involves transducing human MCF7 breast cancer cells with the huBCRP vector.

As depicted in FIG. 1, the reason that human breast cancer cells are preferred is that unwanted monoclonal antibodies (small cell #3) that react to native 3T3 cell proteins (squares and triangles) are not likely to bind to the human proteins present on MCF7 cells. Supernatants are then incubated with the transduced MCF7 cells which express huBCRP. These cells are then stained with a phycoerythrin (PE) conjugated secondary antibody that recognize mouse immunoglobulins. Flow cytometry is then used to detect cell samples that have PE-fluorescence, i.e., cells that bind the murine antibodies from the hybridoma supernatants. These supernatants are likely to contain anti-huBCRP antibodies from their respective monoclonal hybridomas (cell #1). However, it is also possible that the reactivity observed is not due to anti-huBCRP activity, but rather to a murine antibody that cross-reacts with a surface protein found on the MCF7 cell (hybridoma clone 2). To identify and eliminate such clones, all positive supernatants can be back-screened with the parental (non-tranduced) MCF7 cells. These cells do not express huBCRP, but do express all of the native surface proteins present on the transduced MCF7 cells. Therefore, all clones found to react with the parental (non-tranduced) MCF7 cells are discarded.

Hybridoma clones that pass this screening process are then expanded, resubcloned, and reanalzyed. Subclones that pass a second round of screening are then used to make monoclonal antibody containing supernatant in an ex vivo roller-bottle production system. The antibody can then be purified on an affinity column, the isotype can be determined, and the concentration of the antibody measured. This preparation can then be used to identify native stem cells that express the huBCRP gene product on their surface, and to isolate such cells by methods including but not limited to flow cytometry, immunoaffinity columns, or magnetic bead procedures.

The foregoing antibodies can be used in methods known in the art relating to the localization and activity of the BCRP, e.g., for Western blotting, imaging BCRP in situ, measuring levels thereof in appropriate physiological samples, etc. using any of the detection techniques mentioned herein or known in the art. In a specific embodiment, antibodies that agonize or antagonize the activity of BCRP can be generated. Such antibodies can be tested using the assays that measure the drug pumping ability of BCRP, for example.

The antibodies to the ABC transporters can be labeled. Suitable labels include enzymes, fluorophores (e.g., fluorescein isothiocyanate (FITC), phycoerythrin (PE), Texas red (TR), rhodamine, free or chelated lanthanide series salts, especially $Eu^{3+}$, to name a few fluorophores), chromophores, radioisotopes, chelating agents, dyes, colloidal gold, latex particles, ligands (e.g., biotin), and chemiluminescent agents. In the instance where a radioactive label, such as the isotopes $^3H$, $^{14}C$, $^{32}P$, $^{35}S$, $^{125}I$, and $^{131}I$, are used, known currently available counting procedures may be utilized. In the instance where the label is an enzyme, detection may be accomplished by any of the presently utilized calorimetric, spectrophotometric, fluorospectrophotometric, amperometric or gasometric techniques known in the art.

Direct labels are one example of labels which can be used according to the present invention. A direct label has been defined as an entity, which in its natural state, is readily visible, either to the naked eye, or with the aid of an optical filter and/or applied stimulation, e.g. ultraviolet light to promote fluorescence. Among examples of colored labels, which can be used according to the present invention, include metallic sol particles, for example, gold sol particles such as those described by Leuvering (U.S. Pat. No. 4,313,734); dye sole particles such as described by Gribnau et al. (U.S. Pat. No. 4,373,932) and May et al. (WO 88/08534); dyed latex such as described by May, supra, Snyder (EP-A 0 280 559 and 0 281 327); or dyes encapsulated in liposomes as described by Campbell et al. (U.S. Pat. No. 4,703,017). Other direct labels include a radionucleotide, a fluorescent moiety or a luminescent moiety. In addition to these direct labeling devices, indirect labels comprising enzymes can also be used according to the present invention. Various types of enzyme linked immunoassays are well known in the art, for example, alkaline phosphatase and horseradish peroxidase, lysozyme, glucose-6-phosphate dehydrogenase, lactate dehydrogenase, urease, these and others have been discussed in detail by Eva Engvall in Enzyme Immunoassay ELISA and EMIT in *Methods in Enzymology,* 70:419-439 (1980) and in U.S. Pat. No. 4,857, 453.

Suitable enzymes include, but are not limited to, alkaline phosphatase and horseradish peroxidase. In addition, an antibody can be modified to contain a marker protein such as green fluorescent protein as described in U.S. Pat. No. 5,625, 048 filed Apr. 29, 1997, WO 97/26333, published Jul. 24, 1997 and WO 99/64592 all of which are hereby incorporated by reference in their entireties. Other labels for use in the invention include magnetic beads or magnetic resonance imaging labels.

In another embodiment, a phosphorylation site can be created on an antibody of the invention for labeling with $^{32}P$, e.g., as described in European Patent No. 0372707 (application No. 89311108.8) by Sidney Pestka, or U.S. Pat. No. 5,459, 240, issued Oct. 17, 1995 to Foxwell et al.

Antibodies also can be labeled by metabolic labeling. Metabolic labeling occurs during in vitro incubation of the cells that express the protein in the presence of culture medium supplemented with a metabolic label, such as [$^{35}S$]-methionine or [$^{32}P$]-orthophosphate. In addition to metabolic (or biosynthetic) labeling with [$^{35}S$]-methionine, the invention further contemplates labeling with [$^{14}C$]-amino acids and [$^3H$]-amino acids (with the tritium substituted at non-labile positions).

Stem Cell Purification

After an appropriate antibody is identified, mouse bone marrow cells, for example, can be depleted of lineage positive cells, and the lin⁻ cells can be sorted for BCRP expression. Competitive repopulation assays can then be used to demonstrate the enrichment of stem cell activity in the BCRP-expressing fraction. BCRP sorting experiments can also be performed in lin⁻, ckit⁺, scal⁺ cells, and in CD34-cells to determine if these populations can be further enriched for stem cell activity. An analogous procedure can be performed using an alternative cell source, e.g., human cord blood cells.

Thus, BCRP sorting experiments can be performed using lin⁻, CD34-cells, as well as CD34⁺, CD38⁻ cells to determine the amount that BCRP expression enriches for repopulating activity in these stem cell populations. Sorted cells then can be injected into NOD/SCID mice in limiting dilution analyses to quantify the stem cell frequencies in these populations. This procedure can be repeated using bone marrow cells and cytokine-mobilized peripheral blood stem cells to demonstrate the utility of the procedure in various clinical stem cell sources. For example, SP cells were isolated from mouse muscle satellite cells and RT-PCR and FACS analysis was used to demonstrate that BCRP is also expressed in these cells (see Example 1 below). Reconstitution studies can also be performed using sorted BCRP-expressing muscle cells. Sorted donor cells can be identified after transplant using a GFP-transgenic mouse line for donor cells, for example, and analyzing recipients for GFP⁺ SP cells in the muscle.

Therefore, the present invention provides a functional basis for identifying SP stem cells, and furthermore, provides a new way to isolate stem cells both for research and clinical applications. For example, the present invention provides a method of isolating stem cells using an anti-BCRP antibody. These stem cells can originate from any tissue that contains stem cells including from bone marrow cells, muscle cells and even brain cells. Any method that allows the separation of cells that can be distinguished by their ability to bind a particular antibody can be employed. For example, to isolate hematopoietic stem cells, bone marrow cells can be obtained from an animal subject, (preferably a human). Single cell suspensions can then be prepared. An anti-BCRP antibody can be incubated with the cells and the cells can be isolated using standard cell sorting methodology e.g., by fluorescent cell sorting [Bhatia et al., *Nat. Med.* 4:1038-1045 (1998)]. In a related embodiment, muscle stem cells can be isolated from a muscle cell sample [Gussoni et al., Nature 401:390 (1999)]. Alternatively, stem cells can be distinguished from non-stem cells by the specificity of the drug-pumping activity of BCRP.

Bone marrow cells can be obtained from any number of sources from an animal, including a human subject. For example, the cells can be harvested from iliac bone marrow from laboratory animals. Alternatively, hematopoietic stem cells can be obtained from umbilical chord cells. Another source for hematopoietic stem cells is from circulating fetal blood cells. In addition, a human subject, for example, can be treated with a cytotoxic drug and/or a hematopoietic stem cell stimulating cytokine (e.g., G-CSF). Mononuclear cells can then be collected by leukophoresis and the hematopoietic stem cells can be isolated from the peripheral blood cells by their selective binding to an antibody raised against CD34. One source of embryonic stem cells is embryonic/fetal tissue. Sources for obtaining stem cells from a particular tissue type (such as brain or liver) include but are not limited to biopsy samples and cadavers.

BCRP enriched stem cells can be used in the same way, and for the same purposes, as the enriched stem cells that are currently available, e.g., CD34 enriched stem cells. Indeed, the embryonic stem cells provided can be used generally, whereas specific adult stem cells obtained by the methods of the present invention can be used for specific stem cell transplantation e.g., hemopoietic stem cells for bone marrow transplantation, pancreatic stem cells to treat type II diabetes, and brain stem cells to treat Parkinson's disease. The stem cells provided by the present invention can also be used as cell targets in gene therapy protocols. Importantly, cell samples that are identified/selected to be enriched for BCRP expression by the methods disclosed herein comprise a more highly purified population of stem cells than any of the other currently available sources of stem cells that have been isolated based on any alternative stem cell marker (e.g., cell samples selected for expression of CD34). Thus, the enriched stem cell preparations provided by the present invention comprise fewer deleterious anti-host reacting cells and thereby their use significantly lowers the risk of graft versus host disease, and/or transplant rejection and may broaden the number of available donors for a given patient.

Therefore, the BCRP enriched cell samples of the present invention provide a preferred source of purified stem cells for therapeutic applications. These more highly enriched stem cell samples also allow therapeutic applications of stem cells such as allogeneic transplantation, that heretofore, could not be reliably performed due to the relatively higher level of contaminating non-stem cells in prior stem cell preparations.

Furthermore, these highly enriched stem cells are preferred for gene therapy because their use leads to an increase in transduction efficiency and reduces the amount of vector needed for transduction.

BCRP Expression and Leukemia

A significant number of leukemic cells, particularly Acute Myelogenous Leukemia (AML) blasts, can efflux fluorescent dyes and certain chemotherapeutic agents such as mitoxantrone and duanomycin, despite the absence of MDR1 and MRP1 expression. A substantial proportion of these cases are contemplated to be due to the expression of BCRP. AML blasts from newly diagnosed pediatric patients can be assayed for BCRP expression using a variety of techniques as described herein in the context of stem cell identification and purification. Suitable techniques particularly include the use of flow cytometry after staining with a specific anti-BCRP antibody, immunocytochemistry, staining protein lysates with BCRP antibody in Western Blot analyses, and methods that measure BCRP mRNA levels such as PCR, real time PCR, Northern Blot analyses, and ribonuclease protection assays. In cases where significant levels of BCRP expression is found, it can be determined whether the expression of BCRP is due to mutations in the promoter, hypomethylation of promoter sequences, or due to changes in the transcription factor environment.

Determination of BCRP expression in leukemic cells, particularly AML blasts, provides useful information to the medical practitioner with regard to predicting the efficacy of administration of chemotherapeutic agents which are susceptible to efflux via BCRP. Such information may be used by the medical practitioner to determine the optimal course of treatment for a patient suffering from leukemia, particularly AML. For example, in those cases where the leukemic cells of a patient are determined to be expressing significant levels of BCRP, a course of treatment which does not rely upon agents susceptible to reduced efficacy via BCRP efflux such as bone marrow transplant or immunotherapy may be used. Furthermore, in cases where BCRP expression expression predicts poor prognosis with standard treatment, more aggressive treatment plans can be implemented at the outset including more aggressive chemotherapy, or bone marrow transplantation approaches.

The present invention may be better understood by reference to the following non-limiting Examples, which are provided as exemplary of the invention. These examples are presented in order to more fully illustrate the preferred embodiments of the invention. They should in no way be construed, however, as limiting the broad scope of the invention.

EXAMPLES

Example 1

BCRP is Expressed in a Wide Variety of Side Population Stem Cells, Blocks Differentiation of Transduced Hematopoietic Stem Cells and can be used as a Marker for Purification of Stem Cells Introduction Hematopoietic stem cells (HSCs) can be identified by staining with fluorescent dyes such as Rhodamine (Rho) 123 and purified based on efflux of such dyes [Orlic et al., *Blood* 82:762-770 (1993); Fleming et al., *J.Cell Biol.* 122:897-902 (1993); Spangrude and Johnson, *Proc.Natl.Acad.Sci. USA* 87:7433-7437 (1990); Zijlmans et al., *Proc Natl Acad Sci USA* 92:8901-8905 (1995)] and Hoechst 33342 [McAlister et al., *Blood* 75:1240-1246 (1990); Leemhuis et al., *Exp.Hematol.* 24:1215-1224 (1996); Wolf et al., *Exp.Hematol.* 21:614-622 (1993)]. The most primitive HSCs are characterized by low degrees of fluorescence after staining with these dyes, a property ascribed to both their capacity for dye efflux, and to relatively low degrees of mitochondrial staining [Kim et al., *Blood* 91:4106-4117 (1998)]. A related method for stem cell identification has been based on Hoechst dye-staining of whole bone marrow cells, followed by dual emission wavelength analysis by flow cytometry. This technique identifies a small fraction of side population (SP) cells that are highly enriched for repopulating activity [Goodell et al., *J.Exp.Med.* 183:1797-1806 (1996)].

This SP population is highly enriched for repopulating cells and is present in the bone marrow of all species examined [Goodell, M. A. et al., *Nat. Med.* 3:1337-1345 (1997)]. The SP phenotype can be blocked by drugs which inhibit cellular dye efflux mechanisms. It has been thought that the efflux activity responsible for the SP phenotype may be due to expression of P-glycoproteins (P-gps), the products of the mammalian multidrug resistance genes (MDR1 in humans and mdr1a and 1b in mice) [Sorrentino, B. P. et al., *Blood* 86: 491-501 (1995)]. This possibility is suggested by the facts that: (i) Rho123 and Hoechst 33342 are substrates for P-gp, (ii) primitive human hematopoietic cells express high levels of P-gp [Chaudhary and Roninson, *Cell* 66:85-94 (1991)], and (iii) the phenotype of SP cells can be blocked by verapamil, a competitive inhibitor of P-gp [Goodell et al., *J.Exp.Med.* 183:1797-1806 (1996)].

More recent evidence shows that the muscle contains reconstituting cells that can be identified by the SP phenotype [Gussoni et al., *Nature* 401:390-394 (1999); Jackson et al., *Proc.Natl.Acad.Sci. U.S.A* 96:14482-14486 (1999), see comments] suggesting that expression of ABC transporters may be a general stem cell property [Orkin, S. H., *Nat. Med.* 6:1212-1213 (2000)]. Indeed whatever their exact function, it appears that expression of ABC transporters has been evolutionarily conserved in stem cells. The conservation of transporter expression in a wide variety of stem cells is consistent with an important functional role in stem cells.

Although many of the genes encoding ABC transporters were first identified based on their ability to confer drug resistance in tumor cells, it has recently become apparent that they can exert more general effects on cellular function. For example, MDR1 gene expression has been shown to inhibit caspase-dependent apoptosis in a variety of cells [Smyth et al., *Proc.Natl.Acad.Sci. USA* 95:7024-7029 (1998)] including hematopoietic cells [Johnstone et al., *Blood* 93:1075-1085 (1999)]. P-gps can also function as lipid translocases by redistributing membrane phospholipids from the inner to outer leaflet of the cell membrane [van Helvoort et al., *Cell* 87:507-517 (1996)].

Direct evidence that ABC transporters can have a functional effect in HSCs comes from studies of MDR1 gene transfer in mice [Bunting et al., *Blood* 92:2269-2279 (1998); Example 1 of U.S. Ser. No. 09/584,586 filed May 31, 2000, the disclosure of which are hereby incorporated by reference in their entireties]. When murine bone marrow cells were transduced with an MDR1-expressing retroviral vector, dramatic expansion of repopulating stem cells was noted during a 12-day culture period [Bunting et al., *Blood* 92:2269-2279 (1998); Example 1 of U.S. Ser. No. 09/584,586 filed May 31, 2000, the disclosure of which are hereby incorporated by reference in their entireties]. In contrast, repopulating activity was lost over time in control cultures [Bunting et al., *Blood* 96:902-909 (2000); Example 2 of U.S. Ser. No. 09/584,586 filed May 31, 2000, the disclosure of which is hereby incorporated by reference in its entirety]. These results demonstrate that enforced expression of MDR1 results in stem cell self-renewal and expansion during extended culture periods. This expansion of repopulating cells was associated with a parallel increase in SP cells, while SP cells were lost over time in control cultures. These results directly link ABC transporter expression, or at least MDR1 expression, with the SP stem cell phenotype.

One possible mechanism for the stem cell expansion was that P-gp expression could result in the efflux of toxic media components from HSCs during the ex vivo culture period. This possibility was ruled out by the observation that MDR1-transduced stem cells had a direct proliferative advantage in vivo [Example 2 of U.S. Ser. No. 09/584,586 filed May 31, 2000, the disclosure of which is hereby incorporated by reference in its entirety]. When transduced bone marrow cells were directly transplanted in irradiated mice, without an ex vivo expansion phase, there was a progressive outgrowth of MDR1-transduced cells relative to a control graft. These results show that MDR1 expression was conferring a more general effect on stem cell division, and not simply acting through a detoxification mechanism specific to ex vivo culture. Experiments with a mutant P-gp construct demonstrated that HSC expansion required the molecular pump function of P-gp, suggesting that the mechanism of expansion involved modulation of some endogenous molecular substrate within HSCs [Example 2 of U.S. Ser. No. 09/584,586 filed May 31, 2000, the disclosure of which is hereby incorporated by reference in its entirety]. Collectively, these studies show that NMDR1 gene expression can promote HSC self-renewal and amplification.

Heretofore, it was not known if this property is unique to the MDR1 gene, or whether other ABC transporters can exert a similar function.

Results

The regulated expression of endogenous P-gps in HSCs appears to be important in facilitating the self-renewal divisions that maintain the stem cell compartment over time [see Examples 1 and 2 of U.S. Ser. No. 09/584,586 filed May 31, 2000, the disclosure of which is hereby incorporated by reference in its entirety] and indeed, one or more naturally occurring endogenous ABC transporters apparently plays a critical functional role in stem cell homeostasis. This premise is consistent with two observations: (i) HSCs universally express dye-effluxing transporters; and (ii) enforced expression of MDR1 leads to stem cell amplification and myeloproliferation [see Example 1 of U.S. Ser. No. 09/584,586 filed May 31, 2000, the disclosure of which is hereby incorporated by reference in its entirety].

As disclosed herein, an alternate ABC transporter(s) is expressed in SP stem cells derived from the mdr1a/1b knockout mouse. The analyses of mRNA from sorted SP stem cells have identified several newly cloned transporters that are expressed in SP HSCs, that may possibly have a role in the self-renewal process of HSCs. The most highly expressed is the Bcrp1/Mxr/Abcp/ABCG2 gene product, BCRP. Importantly, there is no detectable expression of BCRP in peripheral blood leukocytes, spleen, or thymus at the level of Northern blot analysis, while small but detectable amounts of BCRP mRNA were expressed in human fetal liver.

An ABC Transporter Other than P-gp is Expressed in Murine SP HSCs:

Quantitative repopulation assays were performed using commercially available mdr1a/ab--/-- mice as donors because it is well known that severe quantitative stem cell abnormalities can coexist with relatively normal peripheral blood counts such as in W/WV mice. Normal numbers of repopulating cells were found to be present in the bone marrow. Bone marrow cells were then analyzed for the content of SP cells after staining with Hoechst dye. To confirm that the knockout mice had the expected phenotype, it was verified that the capacity for Rho 123 efflux had been lost in peripheral blood leukocytes as has been previously described [Schinkel et al., *Proc Natl Acad Sci USA* 94:4028-4033 (1997)]. Despite this loss of P-gp related transporter function, SP cells were present in normal numbers in the bone marrow when compared to wild type mice of the same strain. This indicates that another ABC transporter is likely being expressed, potentially compensating for the loss of P-gp function.

To further test this possibility, biochemical studies were performed on knockout bone marrow cells using known inhibitors of ABC transporter efflux function. Cells were treated with either verapamil or 2-deoxyglucose. Verapamil is a competitive inhibitor of several known ABC transporters including MDR1, whereas 2-deoxyglucose is an inhibitor of ATP synthesis that depletes cellular ATP levels required for ABC transporter function. Treatment with either of these compounds before and during Hoechst 33342 staining eliminated phenotypically identifiable SP cells. These results conclusively demonstrate that another ABC transporter(s) is being expressed in SP cells from the bone marrow of mdr1a/1b knockout mice and is (are) responsible for the SP phenotype.

Identification of Bcrp as an Expressed ABC Transporter in Hematopoietic Stem Cells:

An RT-PCR assay was developed to detect mRNA expression of other known ABC transporters in murine bone marrow SP cells. Based on the published human sequences for MRP1 [Cole et al., Science 258:1650-1654 (1992), see comments], MRPs 2, 3, 4 [Kool et al., Cancer Res. 57:3537-3547 (1997)], and BCRP [Doyle et al., Proc.Natl.Acad.Sci. U.S.A 95:15665-15670 (1998):published erratum appears in Proc Natl Acad Sci U S A; 96(5):2569 (1999)] homologous sequences from the murine EST database were identified to design PCR primers for cDNA amplification. Multiple primer sets were tested using mouse liver cDNA as a template, and primer sets were chosen that gave specific bands of the expected size. Using FACS, bone marrow SP cells were sorted from both normal mice and the mdr1a/1b knockout mouse. Total cellular RNA was prepared from 50,000 and 100,000 purified SP cells, and then used for RT-PCR analysis. These experiments showed that the Bcrp1 (MBCRP) mRNA was the most highly expressed of all the transporters studied. Moderate expression levels were observed for mrp4 and mrp1, while mrp3 was expressed at very low levels, and no detectable expression of mrp2 was observed. The low levels of expression of mrp1 in the liver correlated with previously described low levels of expression of MRP1 in human liver [Kool et al., Cancer Res. 57:3537-3547 (1997)]. Virtually identical results were obtained using sorted SP cells from normal mice.

It is important to note that while SP cells are highly enriched for repopulating cells, at least 250 SP cells are required to achieve significant repopulation in mice [Goodell et al., J.Exp.Med. 183:1797-1806 (1996)] indicating that most SP cells are not true stem cells. In contrast, it has previously been shown that CD34$^-$, c-kit$^+$, Sca1$^+$, lineage negative (CD34-KSL) cells from the bone marrow are a relatively pure subset of repopulating cells, with repopulation in about 20% of mice that are transplanted with single sorted cells [Osawa et al., Science 273:242-245 (1996)]. Therefore, transporter expression was studied in the highly purified CD34-KSL population, as well as from a number of other different sorted populations.

Like SP cells, the CD34-KSL cells expressed relatively high levels of mBCRP mRNA, however in contrast to SP cells, there were little to no expression of the other ABC transporters. In the more differentiated CD34$^+$ KSL cell fraction, there was marked downregulation of mBCRP expression with the appearance of significant expression of mrp1, 2, and 4. The S$^+$K$^+$Lin$^-$ population is a mixture of CD34$^-$ and +cells, and gave results that were intermediate between the CD34$^+$ and − subfractions. mBCRP expression was not detectable in granulocytes, macrophages, B cells, or thymocytes. The only other cell populations with detectable MBCRP expression were erythroid progenitors (Ter119$^+$) and natural killer cells (NK1.1$^+$). These results suggest that mBCRP expression is highly specific for repopulating stem cells in the lineage negative compartment of the bone marrow, and that expression of other transporters in the sorted SP cell population were likely due to the presence of more differentiated cells with lesser degrees of repopulation potential. These data indicate that BCRP expression should be a useful marker for stem cell identification and purification. The expression data are also consistent with a necessary functional role for BCRP gene expression in repopulating hematopoietic stem cells, and perhaps in SP stem cells from muscle and other tissues.

High Levels of Expression of BCRP mRNA in Sorted SP Cells from Rhesus Monkey Bone Marrow:

To determine if primate SP cells were expressing BCRP, a bone marrow aspirate sample was obtained from a normal Rhesus Monkey. After lysis of the red blood cells, the leukocyte population was stained with Hoechst dye and analyzed by flow cytometry for SP cells. The flow pattern was very similar to that obtained with mouse bone marrow, with about 0.05% of cells falling into the SP gate (see above). Sorting was performed and resulted in isolation of 2000 SP cells, and 10,000 cells from a distinct gate outside of the SP region (non-SP cells). RNA was extracted, and a RT-PCR cycle curve using β-actin primers as an internal control showed roughly equivalent signals at 35 cycles for non-SP cells versus 60 cycles for SP cells. These PCR conditions were repeated using BCRP-specific primers in place of the β-actin primers. A strong signal was obtained with BCRP primers at 60 cycles in the SP cells sample, and a much fainter signal was detected at 50 cycles. No BCRP signal was detected at 35 cycles in the non-SP sample, which was the highest cycle number used for this sample. These results demonstrate relatively specific, high level expression of BCRP mRNA in monkey SP cells since the β-actin signal for non-SP cells at 35 cycles was actually greater than the signal for SP cells at 60 cycles. Taken together with the mouse data, (above) these results show that the expression of a BCRP transporter ortholog is conserved in SP stem cells from diverse species. In addition, these results further confirm that human stem cells can be identified and/or purified by monitoring/exploiting their unique BCRP expression.

Expression of Bcrp1 in Murine Myoblast SP Cells and Murine ES Cells:

Stem cells bearing the SP phenotype have also been identified in murine muscle, and appear to be related to the satellite cells that are located on the periphery of the muscle fiber. Consistently, these cells also appear to be associated with muscle regeneration.

SP cells were therefore isolated from the murine muscle, and assayed for mBCRP expression by RT-PCR to further correlate Bcrp1 (MBCRP) expression with the SP phenotype. Muscle tissue was dissected, minced, digested with collagenase, and a single cell suspension was stained with Hoechst dye for SP cell analysis. An SP population of cells was observed with FACS analysis that bears a striking resemblance to the profile seen with bone marrow cells. Gated myoblast SP cells were sorted, and RNA was prepared from a fraction of 20,000 cells. RT-PCR analysis showed relatively high levels of mBCRP expression. However, unlike the results with monkey bone marrow, a distinct non-SP cell fraction was not available for analysis.

These results further support the conclusion that MBCRP expression can be used to identify SP stem cells from a variety of organs.

In contrast to the results described above, the non-SP population from murine ES cells expressed mBCRP at equivalent levels to the SP fraction. This is not surprising because ES cells are clonally derived and are expected to be homogenous with regard to gene expression. These results show that mBCRP expression is conserved in all SP populations that were studied, and suggests a possible required role for mBCRP in stem cell function.

Vector-mediated Expression of ABCG2 (huBCRP) Directly Confers the SP Phenotype.

A pcDNA-based BCRP vector was used to transfect Soas2 cells, which were then analyzed for their dye efflux properties. Transfected clones readily effluxed Hoechst dye but not rho, and the efflux activity was fully inhibited by reserpine. Furthermore, an inactivating mutation in the Walker A motif abolished the Hoechst dye efflux activity, showing the requirement for transporter pump function in dye efflux. These findings are fully consistent with the Hoechst low, rho bright phenotype of bone marrow SP cells from mdr1a/1b$^{-/-}$ mice.

A retroviral producer cell line was then used based on the Harvey murine sarcoma virus backbone (HaBCRP) to transduce normal murine bone marrow cells. After culture in myeloid cytokines for 12 days, vector-transduced cells showed a large increase in the number of SP cells, with greater than 60% of the cells falling within the SP region. By comparison, only 0.05% of cells that were mock-transduced showed the SP phenotype. HaBCRP-transduced bone marrow cells were also transplanted into lethally irradiated recipients to determine if SP expansion could be directly obtained in vivo. Three mice were killed 5 weeks after transplant, and all showed increased proportions of SP cells in the bone marrow ranging between 1.4 to 11.4% SP cells. Altogether, these results show that expression of HuBCRP transporter can directly confer the SP phenotype in transduced primary bone marrow cells.

Enforced Expression of HuBCRP in Murine Bone Marrow Cells Blocks Differentiation.

To determine the functional effects of enforced HuBCRP expression, HaBCRP-transduced bone marrow cells were assayed for their ability to generate myeloid progenitor colonies. In cells that were analyzed directly after transduction, a significant decrease in CFU-C and CFU-S formation was seen in HaBCRP-transduced populations. The plating efficiency of CFU-C was decreased between 4-6 fold in 2 independent experiments. Control cells gave confluent CFU-S at a dose of $1\times10^5$ cells, while HaBCRP-transduced cells gave only a few discrete colonies. To control for non-specific effects of HuBCRP expression in the producer cells during the coculture phase of transduction, bone marrow cells were also co-cultured with HaBCRP-transduced 3T3 cells. No effects on progenitor content were seen with this control.

Lethally irradiated C57B1/6J mice were then transplanted with HaBCRP-transduced cells and the effects on hematopoietic reconstitution were studied. Despite amplification of SP cells in the bone marrow in all 3 cases, transduction with HaBCRP was associated with a significant decrease in the peripheral white blood cell count at 5 weeks, and a parallel decrease in the CFU-C content in the bone marrow. Competitive repopulation assays were next performed to more precisely quantify the effects of vector expression on myeloid maturation. Mock-transduced bone marrow cells were competed in equal ratios with either HaBCRP-transduced cells, or with cells transduced with a control MSCV-GFP vector. At 9 weeks after transplant, peripheral contributions to the erythrocyte compartment were measured using an electrophoresis assay that distinguishes between donor specific hemoglobin polymorphisms [Bunting, K. D. et al., Blood 96: 902-909 (2000); U.S. Ser. No. 09/584,586 filed May 31, 2000, the disclosures of which are hereby incorporated by reference in their entireties]. These studies showed that the HaBCRP vector caused a marked inhibition of erythroid repopulation that was not seen in mock controls. Altogether, these results show that enforced expression of HuBCRP can block hematopoietic differentiation, and suggest that endogenously expressed BCRP HuBCRP may function to maintain stem cells in a primitive, pluripotent state. Derivation of murine monoclonal antibodies against the human ABCG2 (huBCRP) gene product: A human BCRP cDNA was obtained as a full length EST from Genome Systems in St. Louis, Mo. (see Methods above). This cDNA was cloned into the Harvey murine sarcoma virus backbone to create the HaBCRP retroviral vector, as described above. This vector was next introduced into the ecotropic packaging cell line GPE86, and vector-containing supernatant was used transduce NIH 3T3 cells. A polyclonal population of cells (designated 3T3-BCRP) was isolated by flow cytometry, gating on cells that efflux the fluorescent dye Hoechst 33342. Expression of the HuBCRP gene product in these cells was confirmed by Western blot analysis using a polyclonal serum raised in rabbits to an internal peptide epitope.

The 3T3-BCRP cells were used to immunize mice. Twenty BALB-C mice were immunized with whole, living 3T3-BCRP cells by injecting 4 million cells directly into the peritoneal space. Fourteen days later, these cells were reinjected as an immunization boost. Individual mice that showed antibody reactivity in the serum were killed and hybridoma clones were isolated after cell fusion and selection with HAT media. Supernatants from each hybridoma clone were screened by flow cytometry using a human breast cancer cell line (MCF-7) that had been transduced with an amphotrophic HaBCRP vector. Any supernatant that showed reactivity in this assay was then back-screened on the parental MCF-7 line, and clones that reacted with the MCF-7 HaBCRP cells but not with the parental MCF-7 line were scored as positive and specific. These cells were then subcloned, and re-screened based on the indicator cell lines (see FIG. 1).

Independent subclones that show relatively large shifts with the MCF-7 HaBCRP cells, but not with the parental control cells are then isolated. Clones that can detect expression of the HaBCRP vector in bone marrow cells from previously transplanted mice are then expanded to produce larger quantities of supernatant ex vivo with a rollerbottle production system. The antibodies are then purified on an affinity column. These antibodies can then be tested for their ability to detect the endogenously expressed huBCRP gene product in human umbilical cord blood samples. Antibodies that detect the endogenously expressed ABCG2 gene product in human umbilical cord blood samples can then be used to identify and/or isolate stem cells.

Discussion

While Hoechst and rho dye staining have long served as methods for hematopoietic stem cell purification, the molecular basis for this phenotype has not been defined. The results provided herein show that both Bcrp1 and MDR1 homologues are expressed in a relatively restricted manner in primitive stem cells. The fact that SP cells are not diminished in mdr1a1b$^{-/-}$ mice is explained by the compensatory Hoechst efflux activity provided by Bcrp1 expression. The lack of rho dull SP cells in mdr1a1b$^{-/-}$ mice is similarly explained by the fact that Pgp can efflux rho but the BCRP pump cannot. The finding that these dye efflux activities are molecularly distinguishable has significant implications for stem cell purification strategies. For instance, murine ES cells do not efflux rho, implying that Hoechst dye efflux (mBCRP expression) is a more specific stem cell marker.

Several aspects of the data disclosed herein indicate that BCRP plays an important functional role in stem cells. The conserved expression of this transporter in SP stem cells from a wide variety of sources is consistent with a required function. Secondly, the tightly regulated expression pattern of Bcrp1 in murine hematopoiesis, where expression is markedly decreased in early stages of differentiation, is consistent with a stem cell-specific role. Further evidence is provided by overexpression studies, where enforced huBCRP expression leads to a defect in hematopoietic differentiation. In vivo, the HaBCRP vector caused an accumulation of SP cells in the bone marrow, but mature progeny from these cells were significantly decreased in the bone marrow and peripheral blood, and a direct inhibitory effect on CFU-C and CFU-S formation was observed. Altogether, these results are best explained by a model where Bcrp1 expression in stem cells confers relative resistance to commitment and differentiation and thereby contributes to maintaining a primitive, pluripotent state. This potential anti-differentiative effect would then be alleviated with the observed decrease in expression that occurs during early commitment. Along these lines, the results of enforced expression can now be explained by promiscuous expression of Bcrp1 in more mature compartments where endogenous expression does not normally occur. The block to development could occur in these compartments as the result of deregulated Bcrp1 expression.

In considering the mechanism for these effects, it is notable that the normal physiologic functions of BCRP have not yet been defined. The gene was first isolated from human tumor cell lines and shown to be involved in drug resistance [Doyle, L. A. et al., *Proc. Natl. Acad. Sci. U.S. A* 95:15665-15670 (1998); Miyake, K. et al., *Cancer Res.* 59:8-13 (1999); Maliepaard, M. et al., *Cancer Res.* 59: 4559-4563 (1999)]. The primary structure of huBCRP shares the highest homology with the Drosophila white gene product. These "half transporters" have only one ATP binding cassette, and are thought to require homo- or heterodimerization for ATP hydrolysis and function. The white gene product heterodimerizes with two other half transporters, and these interactions specifically define eye color in Drosophila [Ewart, G. D. et al., *J. Biol. Chem.* 269,10370-10377 (1994)]. BCRP may also form heterodimers in mammalian cells with other as yet undefined partners, and these interactions could affect substrate specificity.

While the mechanism for the effects of huBCRP expression on hematopoietic differentiation is not known, several general possibilities can be proposed. There is a precedent for the ability of ABC transporters to maintain stem cell primitivity in lower organisms. Dictyostelium cells express a transport activity defined by rho efflux that maintains cells in a primitive undifferentiated state [Good, J. R. & Kuspa, A., *Dev. Biol.* 220: 53-61 (2000)]. This effect is conferred by efflux of a differentiation-inducing factor, DIF-1, from the interior of prespore cells. It is possible that Bcrp1 is modulating an analogous substrate in mammalian cells. A second possibility is that the Bcrp1 pump may play a role in mediating extracellular signals that dictate stem cell interactions with the microenvironment. This type of effect on extracellular signaling has recently been demonstrated in mrp1$^{-/-}$ mice, where this transporter has been shown to be required for normal dendritic cell migration via transport of leukotrienes to the extracellular space [Robbiani, D. R. et al., *Cell* 103: 757-768 (2000)]. A third possibility is that Bcrp1 may be providing a function that is redundant with mdr1a, so that the loss of a potential anti-apoptotic signal in stem cells in the mdr1a/1b$^{-/-}$ knockout mice could be compensated by Bcrp1 expression.

Methods

Retroviral-mediated Gene Transfer into Murine Hematopoietic Stem Cells:

Bone marrow cells can be harvested from C57BL/6 or B6.Ch-1<b>/By (referred to as "HW80") congenic mouse strains (Jackson Laboratories, Bar Harbor, Me.) by standard methods. Following isolation, cells are placed into liquid suspension culture in Dulbecco's Modified Eagle's Medium (DMEM) (BioWhittaker, Walkersville, Md.) with 1% penicillin/streptomycin (Gibco/BRL, Grand Island, N.Y.), 15% fetal bovine serum (FBS; Hyclone, Logan Utah), 20 ng/ml murine interleukin (IL)-3 R & D Systems, Minneapolis, Minn.), 50 ng/ml human IL-6 (Amgen, Thousand Oaks, Calif.), and 50 ng/ml murine stem cell factor R & D Systems). The cells are initially plated at $1 \times 10^6$ cells/ml in 10 mls of medium. Following pre-stimulation for 48 hours, cells are replated onto confluent monolayers of irradiated ecotropic producer cell lines. The bone marrow cells were plated at the same density used in the pre-stimulation phase and in the same medium with 6 µg/ml polybrene added. Co-culture with producer cells is continued for 48 hours followed by harvest of bone marrow cells. A small sample of bone marrow cells are plated into methylcellulose to score drug-resistant myeloid progenitors.

Southern Blot Analysis:

DNA can be prepared as previously described [Sorrentino et al., *Science* 257:99-103 (1992)]. Typically 10 to 20 mg of genomic DNA is restriction digested with either EcoRI or NheI, and separated on a 1% agarose gel. Gels can be blotted overnight onto Hybond N$^+$ nylon membrane (Amersham), UV crosslinked, and hybridized with either MDR1 or hemoglobin-specific [$^{32}$P]-labeled probes. Blots are washed extensively at 65° C., exposed overnight, and can be analyzed on a phosphorimager (Molecular Dynamics).

Rhodamine 123 (Rho123) Staining:

Rho123 staining can be performed by trypsinizing cells, resuspending the cells in DMEM medium containing 10% FCS at a concentration of $1 \times 10^6$ cells ml, and adding Rho 123 (Sigma) at a final concentration of 1 ug/ml. The cells are then incubated at 37° C. for one hour in the dark, washed once with 10 mls of PBS, and resuspended in DMEM/10% FCS. The cells are next incubated at 37° C. for one hour to allow for efflux, spun down, and then resuspended in 1 ml of PBS for FACS analysis.

4E3 Antibody and Rhodamine 123 Staining:

Producer cells can be analyzed for an ABC transporter, e.g., P-gp expression by staining with a monoclonal mouse anti-human P-glycoprotein antibody (clone 4E3, DAKO, Carpinteria, Calif.). Adherent cells are trypsinized, and resuspended in 50 ul PBS containing 2% BSA and 0.1% NaN3. 5 ul of the 4E3 antibody are then added, incubated at room temp (RT) for 30 minutes, washed twice with phosphate buffered saline (PBS), and then resuspended in 50 ul PBS containing 2% BSA and 0.1% NaN3. After the primary antibody staining, 5 ul of PE-conjugated, rabbit anti-mouse antibody (DAKO) is added as a secondary stain. The cells are then incubated at RT for 30 minutes, washed twice with PBS, resuspended in PBS for FACS analysis.

Hoechst 33342 SP Cell Assay:

Murine bone marrow cells are collected and resuspended at $1\times10^6$ cells/ml in DMEM plus 10 mM HEPES and 2% FBS. In a water bath, the cells are allowed to equilibrate at 37° C., followed by addition of 5 µg/ml Hoechst 33342 (Fisher Scientific, Pittsburgh, Pa.) for 90 minutes as previously described [Goodell et al., *J. Exp. Med.*, 183:1797-1806 (1996)]. Cells are then centrifuged at 4° C. and resuspended in ice cold HBSS plus 10 mM HEPES and 2% FBS at $1\times10^7$ cells/ml. For flow cytometric analysis or sorting, a Becton Dickinson FACS Vantage flow cytometer (Becton Dickinson, San Jose, Calif.) can be configured for dual emission wavelength analysis as previously described [Goodell et al., *J. Exp. Med.*, 183:1797-1806 (1996)]. Cells are gated based on forward and side light scatter to exclude debris. Propidium iodide staining (2 µg/ml) can be utilized to derive a gate excluding dead cells. Cells are analyzed at approximately 5,000 cells/second until data from $1\times10^6$ cells are collected. The SP cell gate can be defined based on normal fresh bone marrow cells,(C57BL/6 for example).

Mice:

Both male and female mdr1a/1b$^{-/-}$ mice, backcrossed onto the FVB background, were purchased from Taconic Labs (Germantown, N.Y.). For transplant studies, female C57BL/6J and B6.C-H1b/ByJ mice (referred to as HW80) were purchased from Jackson Laboratories (Bar Harbor, Me.), and used between 8 and 14 weeks of age.

SP Cell Analysis.

Murine and Rhesus monkey SP cell analyses was performed exactly as previously described [Goodell, M. A. et al., *J. Exp. Med.* 183:1797-1806 (1996); Goodell, M. A. et al., *Nat. Med.* 3:1337-1345 (1997)]. For the inhibitor experiments, 2-deoxyglucose and sodium azide (Sigma, St. Louis), or reserpine (Sigma) were added to cells at a final concentration of 50 and 15 mM, or 5 µM respectively. Cells were then incubated at 37° C. for 15 minutes prior to adding Hoechst 33342 dye. In other experiments, bone marrow cells were incubated in the presence of 0.1 µg/ml rhodamine 123 (Sigma) at 37° C. for 20 minutes, then resuspended in medium containing Hoechst 33342 for SP analysis.

Cell Sorting and RNA Extraction.

Using a FACS Vantage (Becton Dickinson, San Jose, Calif.) for flow cytometric sorting, approximately 300,000 and 160,000 SP cells were isolated from the bone marrow of mdr1a/1b$^{-/-}$ and wildtype mice respectively. Rhesus monkey bone marrow cells from a 2 ml aspirate were sorted by flow cytometry, and approximately 2,000 SP and 10,000 non-SP cells were isolated. Single cell suspensions of murine skeletal muscle cells were prepared for SP analysis as previously described [Gussoni, E. et al., *Nature* 401:390-394 (1999)], and 10,000 SP and non-SP cells were sorted. The procedure for purifying murine CD34$^-$ stem cells has been previously described [Osawa, M. et al., *Science* 273:242-245 (1996)]. In all cases, total RNA from the sorted cells was isolated using RNA STAT-60 (Tel-Test, INC. Friendswood, Tex.) according to the manufacture's recommendations.

RT-PCR Assays.

The primers used for PCR amplification are as follows:

```
murine bcrp1: 5'-CCATAGCCACAGGCCAAAGT-3', SEQ ID
NO:17 and
5'-GGGCCACATGATTCTTCCAC-3', SEQ ID NO:18
for a 327bp fragment;
```

```
Rhesus BCRP: 5'-GGCCTCAGGAAGACTTTATGT-3', SEQ ID
NO:19
and
5'-AAGGAGGTGGTGTAGCTGAT-3', SEQ ID NO:20
for a 342bp fragment.
```

Multiplex PCR for MDR1 like genes utilized a forward primer for mdr1a and mdr2 5'-AGCTGGAGAGATCCTCACC-3', SEQ ID NO:21, a forward primer for mdr1b 5'-AGCCGGAGAGATCCTCACC-3', SEQ ID NO:22 and reverse primers for mdr1a, mdr1b, and mdr2 respectively:

```
5'-CTGTAGCTGTCAATCTCGGG-3',   SEQ ID NO:23,

5'-CTGTAGCTGTCAATCTCAGG-3',   SEQ ID NO:24, and

5'-CTGTAGCTGTCAATCAGAGG-3',   SEQ ID NO:25.
```

These primers amplify a 730 bp fragment for all 3 cDNAs. PCR products were digested with a mixture of BstXI, BglII, and EcoRI at 37° C. to distinguish the relative contributions from each cDNA species (mdr1a BstXI digestion: 619+111 bp, mdr1b BglII digestion: 305+425 bp, mdr2 EcoRI digestion: 452+278 bp).

RNA was treated with RQ1 RNase-free Dnase (Promega, Madison, Wis.) and reverse transcribed into cDNA by using Superscript II RT (Gibco-BRL, Gaithersburg, Md.) and a mixture of oligo dT primers and random hexamers, according to the manufacturers instructions. All cDNAs were first normalized using GAPDH as a standard. In the experiments involving murine SP populations, ABC transporter amplification were performed using 32 cycles. In CD34$^-$ experiments, GAPDH normalized cDNA aliquots were amplified with mBCRP primers for 35 cycles. In the Rhesus monkey experiments, RNA from 2000 SP cells was amplified for HuBCRP or β-actin using 60 cycles, while RNA from 10,000 non-SP cells was amplified using 35 cycles, based on the observation that these different conditions gave equivalent β-actin signals from each sample. All PCR reactions were performed using 0.2 µL P$^{32}$-labeled CTP at 800 µCi/mmol/L in the reaction mix. After amplification, 20 µL of the reaction mix was electrophoresed on a 5% nondenaturing polyacrylamide gel.

HuBCRP expression vectors, transduction, and transplants.

The human BCRP cDNA was obtained (Genome Systems, St. Louis, Mo.) as a full length EST # 52176, SEQ ID NO:26. This cDNA was cloned either into the pcDNA$_3$ expression vector (Invitrogen, Palo Alto, Calif.), or used to replace the MDR1 cDNA in the HaMDR1sc vector [Bunting, K. D. et al., *Blood* 92: 2269-2279 (1998); Bunting, K. D. et al., *Blood* 96: 902-909 (2000); U.S. Ser. No. 09/584,586 filed May 31, 2000, the disclosures of which are hereby incorporated by reference in their entireties]. Polyclonal populations of ecotropic producer cells were generated by transducing GP$^+$E86 packaging cells [Markowitz, D. et al., *J. Virol.* 62:1120-1124 (1988)] with a transient supernatant derived from transfected 293T cells, as previously described [Persons, D. A. et al., *Blood Cells Mol. Dis.* 24: 167-182 (1998)]. Vector-transduced producer cells were then isolated by cell sorting for Hoechst 33342 dim cells. The methods for transduction of bone marrow cells, in vitro expansion of cells, murine transplants, and competitive repopulation assays has been previously described [Allay, J. A. et al., *Nat. Med.* 4:1136-1143 (1998)]. CFU-C and CFU-S assays were done as previously described [Allay, J. A. et al., *Blood* 90: 3546-3554 (1997); Persons, D. A. et al., *Blood* 90:1777-1786 (1997)].

Example 2

BCRP Expression in Blasts From Pediatric Acute Myelogenous Leukemia (AML)

Clinical evidence shows an association between dysregulated ABC transporter expression and human leukemia. In chronic myelogenous leukemia, about 60% of chronic phase patients exhibit P-gp expression in leukemic cells from the bone marrow [Giles et al., *Cancer* 86:805-813 (1999)]. In patients with acute myelogenous leukemia (AML), between 35 and 70% of cases demonstrate P-gp expression in leukemic blasts at diagnosis, and P-gp expression was a strongly negative prognostic factor [Leith et al., *Blood* 94:1086-1099 (1999)]. In contrast, normal late myeloid cells in humans do not express P-gp [Drach et al., *Blood* 80:2729-2734 (1992), see comments]. In some cases, increased P-gp expression in blast cells was due to hypomethylation of sequences in the MDR1 promoter [Nakayama et al., *Blood* 92:4296-4307 (1998)]. Expression of other ABC transporters can occur in human AML, as has been documented for the multidrug resistance protein (MRP1), and the lung resistance protein (LRP) [Leith et al., *Blood* 94:1086-1099 (1999); Michieli et al., *Br. J.Haematol.* 104:328-335 (1999)]. Importantly, a significant number of AML cases showed inhibitable dye efflux activity that was not associated with MDR1, MRP1, or LRP [Michieli et al., *Br. J.Haematol.* 104:328-335 (1999); Leith et al., *Blood* 86:2329-2342 (1995)].

To determine if BCRP expression could be detected in leukemia cells from pediatric patients with AML, RT-PCR analysis was performed on RNAs derived from leukemic bone marrow from four individual cases. Two cases were strongly positive for BCRP mRNA, with BCRP-amplified fragments detected at 25 cycles of amplification. Interestingly both of these "high-expressing" cases were associated with the M1 FAB phenotype. Two other cases with an M5 phenotype did not show any detectable signal at 25 cycles, but BCRP could be detected at 30 cycles. β-actin controls demonstrated that this variation was not due to differences in mRNA loading. The low level signal seen in the M5 cases could have been due to contaminating erythroid progenitors which may be expressing BCRP, or due to low level BCRP expression in the blast cells. These data confirm that BCRP mRNA expression can be detected in at least some primary AML samples. Furthermore, these results provide further impetus for using an anti-BCRP antibody to probe blast cell samples in the diagnosis/prognosis of AML.

While the invention has been described and illustrated herein by references to the specific embodiments, various specific material, procedures and examples, it is understood that the invention is not restricted to the particular material combinations of material, and procedures selected for that purpose. Indeed, various modifications of the invention in addition to those described herein will become apparent to those skilled in the art from the foregoing description. Such modifications are intended to fall within the scope of the appended claims.

It is further to be understood that all base sizes or amino acid sizes, and all molecular weight or molecular mass values, given for nucleic acids or polypeptides are approximate, and are provided for description.

Various publications, patent applications and patents are cited herein, the disclosures of which are incorporated by reference in their entireties.

What is claimed is:

1. An isolated antibody that binds to an extracellular portion of a Breast Cancer Resistance Protein (BCRP) selected from the group consisting of human BCRP (huBCRP) or murine BCRP (mBCRP); wherein the extracellular portion of the BCRP is in its natural conformation; wherein the antibody binds to living MCF-7 or 3T3 cells expressing BCRP on their surface; wherein the antibody does not bind to living MCF-7 cells that do not express BCRP on their surface; and wherein the antibody does not bind to denatured BCRP.

2. The isolated antibody of claim 1 wherein the isolated antibody is monoclonal.

3. The isolated antibody of claim 1 wherein the isolated antibody is chimeric.

4. The isolated antibody of claim 3 wherein the antibody is humanized.

5. The isolated antibody of claim 1, operably attached to a detectable label.

6. An immunodetection kit comprising, in suitable container means, the antibody according to claim 1 and an immunodetection reagent.

7. An isolated antibody that binds to an extracellular portion of a Breast Cancer Resistance Protein (BCRP) selected from the group consisting of human BCRP (huBCRP) or murine BCRP (mBCRP) generated by (i) immunizing an animal with 3T3 cells that express huBCRP or mBCRP in its natural confromation on the cell surface;

(ii) selecting a hybridoma that secretes antibodies that bind to MCF-7 cells that express huBCRP or mBCRP in its natural conformation on the cell surface, said antibodies do not bind to MCF-7 cells that do not express huBCRP or mBCRP in its natural conformation on the cell surface, and do not bind to denatured BCRP; and (iii) isolating an antibody from the hybridoma selected in step (ii).

8. The antibody of claim 7, which is generated in a mouse and wherein the BCRP is human BCRP.

9. An isolated antibody that binds to an extracellular portion of a Breast Cancer Resistance Protein (BCRP) selected from the group consisting of human BCRP (huBCRP) or murine BCRP (mBCRP) generated by isolating an antibody from a hybridoma that secretes antibodies that bind to MCF-7 cells that express huBCRP or mBCRP in its natural conformation on the cell surface, said antibodies do not bind to MCF-7 cells that do not express huBCRP or mBCRP in its natural conformation on the cell surface, and said antibodies do not bind to denatured BCRP, and wherein the hybridoma is generated from an animal immunized with 3T3 cells that express huBCRP or mBCRP in its natural conformation on the cell surface.

10. The antibody of claim 9, wherein the animal is a mouse and the BCRP is human BCRP.

* * * * *